United States Patent
Wang et al.

(10) Patent No.: US 11,952,358 B2
(45) Date of Patent: Apr. 9, 2024

(54) FLAVAN-3-OL ANALOGS AND ANTI-INFLAMMATORY ACTIVITY

(71) Applicant: Hong Kong Baptist University, Hong Kong (CN)

(72) Inventors: Jun Wang, Hong Kong (CN); Zihao Wang, Hong Kong (CN); Qingjing Yang, Hong Kong (CN); Zhaoxiang Bian, Hong Kong (CN)

(73) Assignee: Hong Kong Baptist University, Hong Kong (CN)

( * ) Notice: Subject to any disclaimer, the term of this patent is extended or adjusted under 35 U.S.C. 154(b) by 0 days.

(21) Appl. No.: 18/055,873

(22) Filed: Nov. 16, 2022

(65) Prior Publication Data

US 2023/0159482 A1    May 25, 2023

Related U.S. Application Data

(60) Provisional application No. 63/264,371, filed on Nov. 22, 2021.

(51) Int. Cl.
| | | |
|---|---|---|
| *C07D 311/62* | (2006.01) | |
| *C07D 311/58* | (2006.01) | |
| *C07D 407/04* | (2006.01) | |

(52) U.S. Cl.
CPC .......... *C07D 311/62* (2013.01); *C07D 311/58* (2013.01); *C07D 407/04* (2013.01); *C07B 2200/05* (2013.01)

(58) Field of Classification Search
CPC .................................................. C07D 311/62
See application file for complete search history.

(56) References Cited

U.S. PATENT DOCUMENTS 8,501,970 B2 * 8/2013 Van Der Westhuizen ..................
                                                    A61P 9/10
                                                    549/399
9,840,487 B2 * 12/2017 Scheidt ................ C07D 311/62

OTHER PUBLICATIONS

Augustyn et al (1990): STN International Caplus database (Columbus, Ohio), Accession No. 1990: 611637.*
Cai et al (2019): STN International Caplus database (Columbus, Ohio), Accession No. 2019: 1644708.*
Yao et al (2016): STN International Caplus database (Columbus, Ohio), Accession No. 2016: 1408463.*
Yuanqing et al (2011): STN International Caplus database (Columbus, Ohio), Accession No. 2011: 1596539.*

* cited by examiner

*Primary Examiner* — Golam M Shameem
(74) *Attorney, Agent, or Firm* — Spruson & Ferguson (Hong Kong) Limited

(57) ABSTRACT

Provided herein are compounds useful in the treatment of inflammatory diseases, pharmaceutical compositions comprising the same, and methods of use and preparation thereof. The compounds exhibit inhibitory effects on the expression and secretion of pro-inflammatory cytokines, such as IL-1β, IL-6 and TNF-α.

13 Claims, 20 Drawing Sheets

| | Inhibition rate of IL-1β secretion(%) | |
|---|---|---|
| | 25 μM | 50 μM |
| 3a | -0.98 | -12.52 |
| 3b | 7.74 | 26.51 |
| 3c | -10.80 | 25.04 |
| 3d | 7.14 | 12.12 |
| 3e | 1.28 | 10.66 |
| 3f | 17.21 | 20.62 |
| 3g | -10.70 | 4.26 |
| 3h | 24.07 | 15.97 |
| 3i | 22.81 | 23.33 |
| 3j | -22.58 | -20.83 |
| 3k | 7.72 | -3.64 |
| 3l | 6.51 | 7.68 |
| 3m | 34.26 | 64.50 |
| 3n | -11.28 | 6.78 |
| 3o | 42.95 | 47.44 |
| 3p | 23.78 | 29.57 |
| 3q | 0.36 | 11.01 |
| 3r | -4.47 | -8.14 |
| 3s | -9.00 | -0.79 |
| 3t | 4.35 | 14.68 |
| 3u | -3.66 | 8.27 |
| 3v | 4.92 | 9.94 |
| 3w | 10.68 | 14.77 |
| 3x | -7.14 | 11.33 |
| 3y | 11.76 | 12.32 |
| 3z | 6.38 | 19.28 |
| 3aa | 4.32 | 10.92 |
| 3ab | 3.49 | 10.18 |
| 3ac | 7.90 | 11.24 |
| 3ad | -20.27 | 39.57 |
| 3ae | 33.22 | 58.53 |
| 3af | 15.15 | -11.78 |
| 3ag | 71.49 | 79.33 |
| 3ah | 12.26 | 37.53 |
| 3ai | 32.33 | -8.45 |

FIG. 4A

| Inhibition rate of IL-6 secretion(%) | | |
|---|---|---|
| | 25 μM | 50 μM |
| 3a | -18.66 | -9.20 |
| 3b | 10.15 | 6.24 |
| 3c | -12.99 | -6.16 |
| 3d | 0.51 | 4.45 |
| 3e | 2.14 | 19.94 |
| 3f | -3.24 | 9.48 |
| 3g | 0.93 | 8.74 |
| 3h | 14.75 | 17.74 |
| 3i | 8.20 | 3.12 |
| 3j | -4.23 | 2.64 |
| 3k | 5.93 | 7.60 |
| 3l | 5.74 | 7.98 |
| 3m | 33.02 | 44.65 |
| 3n | -9.03 | 0.14 |
| 3o | 37.89 | 35.21 |
| 3p | 33.54 | 44.00 |
| 3q | -0.80 | 0.25 |
| 3r | 0.31 | 1.79 |
| 3s | 9.15 | 2.98 |
| 3t | 0.30 | 4.71 |
| 3u | 7.69 | 7.23 |
| 3v | -4.56 | -3.29 |
| 3w | 0.85 | 0.03 |
| 3x | -2.04 | 15.54 |
| 3y | 7.65 | 6.36 |
| 3z | 2.36 | 1.83 |
| 3aa | 10.37 | 20.62 |
| 3ab | -1.73 | 0.23 |
| 3ac | 5.02 | 17.30 |
| 3ad | 11.62 | 13.23 |
| 3ae | 36.72 | 45.02 |
| 3af | 11.31 | -3.61 |
| 3ag | 40.19 | 30.14 |
| 3ah | 2.47 | 3.32 |
| 3ai | 8.49 | 1.96 |

FIG. 4B

| Inhibition rate of TNF-α secretion(%) | | |
|---|---|---|
| | 25 μM | 50 μM |
| 3a | -15.33 | -3.81 |
| 3b | 5.02 | 5.67 |
| 3c | -6.58 | -2.40 |
| 3d | 13.06 | 24.08 |
| 3e | 10.29 | 14.25 |
| 3f | -4.76 | -1.48 |
| 3g | -0.59 | 4.76 |
| 3h | 6.90 | 10.48 |
| 3i | 4.60 | -1.24 |
| 3j | -1.11 | 0.24 |
| 3k | -13.91 | -0.42 |
| 3l | 1.68 | 3.78 |
| 3m | 32.74 | 30.38 |
| 3n | -9.02 | -1.23 |
| 3o | 22.97 | 20.43 |
| 3p | 30.08 | 42.65 |
| 3q | -0.81 | 11.73 |
| 3r | -13.22 | -2.68 |
| 3s | 12.60 | 10.11 |
| 3t | 0.84 | 0.71 |
| 3u | 12.93 | 17.08 |
| 3v | 4.30 | 11.94 |
| 3w | -2.01 | 5.14 |
| 3x | 1.26 | 12.97 |
| 3y | 14.76 | 19.00 |
| 3z | -0.68 | 13.29 |
| 3aa | 11.25 | 18.35 |
| 3ab | 5.38 | 13.93 |
| 3ac | 14.40 | 18.66 |
| 3ad | 15.17 | 13.52 |
| 3ae | 38.68 | 32.97 |
| 3af | 17.79 | 9.65 |
| 3ag | 26.78 | 33.69 |
| 3ah | 0.20 | 0.93 |
| 3ai | 11.41 | 7.38 |

FIG. 4C

Table 1.

Table 1 (Continued).

| entry | ligand | temp. (°C) | (R)-1a[b] yield (%) | (R)-1a[c] ee (%) | 3a[b,d] yield (%) | 3a[c] ee (%) | conv.[e] (%) | s[f] |
|---|---|---|---|---|---|---|---|---|
| 1 | L1 | rt | 32 | 99 | 50 | 73 | 58 | 32 |
| 2 | L2 | rt | 22 | 88 | 37 | 46 | 66 | 7 |
| 3 | L3 | rt | trace | --- | 88 | 11 | --- | --- |
| 4 | L4 | rt | trace | --- | 58 | 7 | --- | --- |
| 5 | L5 | rt | --- | --- | trace | --- | --- | --- |
| 6 | L6 | rt | 58 | 38 | 31 | 79 | 33 | 12 |
| 7 | L7 | rt | 68 | 20 | 16 | 74 | 21 | 8 |
| 8 | L8 | rt | 45 | 62 | 36 | -86 | 42 | 25 |
| 9 | L1 | 0 | 37 | >99 | 62 | 76 | 57 | 37 |
| 10 | L1 | -30 | 43 | >99 | 48 | 93 | 52 | 145 |
| 11 | L1 | -35 | 46 | 99 | 45 | >99 | 50 | 1060 |
| 12 | L1 | -40 | 63 | 50 | 28 | 99 | 37 | 328 |

FIG. 10 (Continued)

Table 2 (Continued).

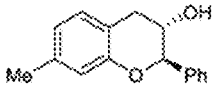

0 °C, 24 h
conv = 50%, s = 526
1s 43% yield, 99% ee
3s 43% yield, 98% ee

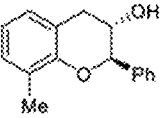

-15 °C, 24 h
conv = 50%, s > 1060
1t 41% yield, 99% ee
3t 46% yield, >99% ee

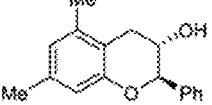

25 °C, 48 h
conv = 49%, s = 789
1u 41% yield, 96% ee
3u 43% yield, >99% ee

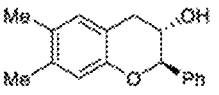

0 °C, 24 h
conv = 50%, s > 1060
1v 39% yield, >99% ee
3v 45% yield, >99% ee

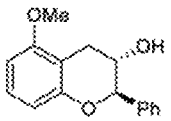

0 °C, 48 h
conv = 49%, s = 789
1w 48% yield, 96% ee
3w 41% yield, >99% ee

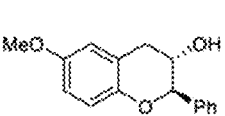

0 °C, 24 h
conv = 50%, s > 1060
1x 42% yield, 99% ee
3x 45% yield, >99% ee

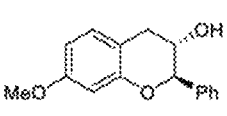

25 °C, 48 h
conv = 47%, s = 584
1y 40% yield, 88% ee
3y 39% yield, >99% ee

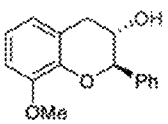

0 °C, 48 h
conv = 49%, s = 844
1z 38% yield, 97% ee
3z 42% yield, >99% ee

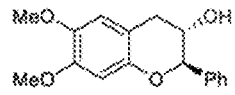

25 °C, 48 h
conv = 46%, s = 171
1aa 40% yield, 83% ee
3aa 39% yield, 97% ee

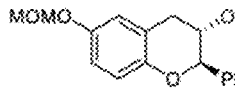

0 °C, 24 h
conv = 50%, s = 194
1ab 35% yield, 96% ee
3ab 48% yield, 96% ee

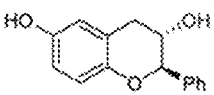

0 °C, 48 h
conv = 49%, s = 747
1ac 43% yield, 95% ee
3ac 42% yield, >99% ee

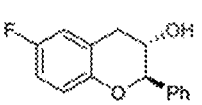

-15 °C, 24 h
conv = 51%, s = 170
1ad 44% yield, >99% ee
3ad 44% yield, 94% ee

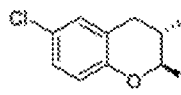

-15 °C, 24 h
conv = 48%, s = 618
1ae 43% yield, 90% ee
3ae 42% yield, 99% ee

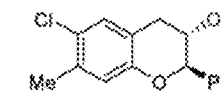

0 °C, 24 h
conv = 50%, s = 525
1af 40% yield, 99% ee
3af 41% yield, 98% ee

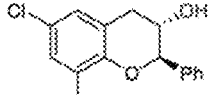

0 °C, 24 h
conv = 49%, s = 354
1ag 41% yield, 94% ee
3ag 44% yield, 98% ee

-15 °C, 24 h
conv = 50.5%, s = 348
1ah 43% yield, 99% ee
3ah 45% yield, 97% ee

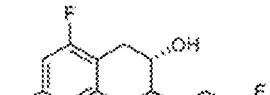

25 °C, 24 h
conv = 49%, s = 790
1ai 42% yield, 96% ee
3ai 40% yield, 99% ee b) (S,S)-Ph-BPE (L1) as the ligand

0 °C, 24 h
conv = 50, s = 922
(s)-1m' 45% yield, 98% ee
(2S,3R)-3m'
48% yield, >99% ee

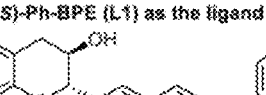

0 °C, 24 h
conv = 46, s = 556
1o' 48% yield, 86% ee
3o' 35% yield, 99% ee

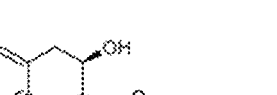

0 °C, 24 h
conv = 50, s = 1060
1p' 33% yield, >99% ee
3p' 45% yield, 99% ee

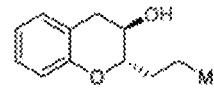

-15 °C, 24 h
conv = 49.5, s = 392
1ae' 42% yield, 96% ee
3ae' 41% yield, 98% ee

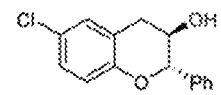

0 °C, 24 h
conv = 49, s = 371
1ag 45% yield, 95% ee
3ag 40% yield, 98% ee

FIG. 11 (Continued)

FLAVAN-3-OL ANALOGS AND ANTI-INFLAMMATORY ACTIVITY

CROSS-REFERENCE TO RELATED APPLICATIONS

This application claims priority from U.S. Provisional Patent Application No. 63/264,371, filed on Nov. 22, 2021, which is incorporated herein by reference in its entirety.

TECHNICAL FIELD

The present disclosure relates to flavan-3-ols and analogs thereof useful as anti-inflammatory agents, pharmaceutical compositions comprising the same, and methods of use and preparation thereof. The compounds exhibit inhibitory effects on the expression and secretion of pro-inflammation cytokines, such as IL-1β, IL-6 and TNF-α.

BACKGROUND

Flavonoids are prevalent structural motifs commonly found in numerous biologically active natural compounds and pharmaceuticals. There are many subgroups of the general structure of a 15-carbon skeleton. Among them, flavan-3-ols (2-phenylchroman-3-ols) and their derivatives, which feature two vicinal chiral centers at the C-2 and C-3, represent an important and special subclass of flavonoids. A number of natural flavan-3-ols including tupichinol A, (+)-catechin, (+)-gallocatechin, (−)-epicatechin-3-gallate and theaflavin have been isolated from natural plants (FIG. 1). These natural products carry various interesting biological activities such as antioxidant, anticancer, antimicrobial and antiviral. Given the interesting and extensive bioactivity of flavan-3-ols, as well as the difficulties and tediousness in isolating them in pure form from natural plants, having an effective asymmetric synthesis strategy to obtain flavan-3-ols is highly desirable. In particular, asymmetric catalysis allows easy manipulation of the stereo-configuration of a library of flavan-3-ols for biological investigations. However, only a very limited number of efficient synthetic methods for constructing chiral flavan-3-ols have been reported. The common approaches for the preparation of this important building block always involve multi-step synthesis, using Sharpless asymmetric dihydroxylation or asymmetric epoxidation (Sharpless epoxidation and Shi epoxidation) to construct the chiral center, and a subsequent cyclization to generate the C ring of the flavan-3-ol framework (FIG. 2a).

Chiral organoboron compounds are versatile intermediates in organic synthesis, chemical biology, and material sciences because the C—B bond can be easily transformed into C—O, C—C, C—N, and C-halogen bonds in a stereo-specific fashion. Transition-metal-catalyzed asymmetric hydroboration of alkenes has proven to be a direct and powerful method for the preparation of chiral alkylboronic acid derivatives. Rh, Ir, Co and Cu complexes have been successfully applied in asymmetric hydroboration of alkenes. Among reported methods, Cu-catalyzed asymmetric hydroboration has gained increasing attention, because of the low cost of the catalyst, mild reaction conditions, and high levels of selectivity. To date, a series of readily available alkenes have been studied in Cu-catalyzed asymmetric hydroboration to give chiral organoboron compounds in high yields and enantioselectivities. Kinetic resolution represents a simple and efficient way to afford both the chiral products and the enantio-enriched starting materials. So far, the scope of reaction, catalysts and substrates suitable for kinetic resolution are still limited, and achieving a high resolution efficiency is a long-standing challenge. In 2013, a kinetic resolution of racemic flavanones via Ru-catalyzed asymmetric transfer hydrogenation was reported. Later, Cu-catalyzed asymmetric hydroboration was applied to racemic 2-substituted 1,2-dihydroquinolines.

There is thus a need to develop new strategies for the construction of flavan-3-ol skeletons with excellent enantioselectivity and the use of flavan-3-ol analogs in the treatment of inflammatory diseases.

SUMMARY

The present disclosure relates to a highly efficient kinetic resolution of chromenes for the first time via Cu-catalyzed asymmetric hydroboration. This novel approach features a simple one-pot synthesis of chiral flavan-3-ols containing two vicinal stereogenic centers via a highly efficient kinetic resolution pathway (s factor up to 1060, >99% ee for most substrates and products, exclusively trans products). In addition, the anti-inflammation effects of these diversified flavan-3-ols were further studied by the in vitro experiments and RNA-sequencing (RNA-seq) analysis. The synthesized flavan-3-ols showed inhibitory effects on the expression and secretion of pro-inflammation cytokines including IL-1β, IL-6 and TNF-α, as well as inhibiting the inflammation responses through downregulating the gene transcriptions closely related to IL-17 signaling pathway, PI3K-Akt signaling pathway and TNF signaling pathway. The results suggested these newly synthesized flavan-3-ols have the potential to be potent lead compounds for developing anti-inflammatory drugs.

In a first aspect, provided herein is a compound of Formula 1:

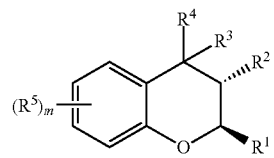

or a pharmaceutically acceptable salt thereof, wherein
m is a whole number selected from 1-3;
n is a whole number selected from 1-3;
p is a whole number selected from 1-2;
q is a whole number selected from 2-6;
$R^1$ is

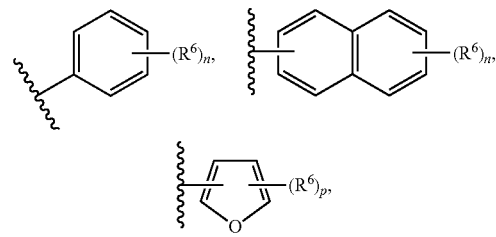

or propyl;
$R^2$ is —OR, —O(C=O)$R^7$, —O(C=O)O$R^7$, —O(C=O)N$(R^7)_2$, or —O(P=O)(OH)$_2$;
each of $R^3$ and $R^4$ is independently hydrogen, alkyl, aryl, heteroaryl, —OR, or —O(C=O)$R^7$; or
$R^3$ and $R^4$ taken together with the carbon to which they are covalently bonded form (C=O);
$R^5$ for each instance is independently selected from the group consisting of hydrogen, halide, nitrile, nitro, —OR, —SR, —NR$_2$, —(C=O)R, —(C=O)OR, —(C=O)NR$_2$, —N(R)(C=O)R, —O(C=O)R, —N(R)(C=O)OR, —O(C=O)NR$_2$, —SO$_2$R, —SO$_2$NR$_2$, haloalkyl, perhaloalkyl, alkyl, cycloalkyl, alkenyl, alkynyl, aryl, heterocycloalkyl, heteroaryl, —OCH$_2$OMe, and —(CR$_2$)$_q$R$^8$; or two instances of $R^5$ taken together form a 5-6 membered cycloalkyl, heterocycloalkyl, aryl, or heteroaryl;
$R^6$ for each instance is independently selected from the group consisting of hydrogen, halide, nitrile, nitro, —OR, —SR, —NR$_2$, —(C=O)R, —(C=O)OR, —(C=O)NR$_2$, —N(R)(C=O)R, —O(C=O)R, —N(R)(C=O)OR, —O(C=O)NR$_2$, —SO$_2$R, —SO$_2$NR$_2$, haloalkyl, perhaloalkyl, alkyl, cycloalkyl, alkenyl, alkynyl, aryl, heterocycloalkyl, heteroaryl, —OCH$_2$OMe, and —(CR$_2$)$_q$R$^8$;
$R^7$ for each instance is independently selected from the group consisting of hydrogen, alkyl, cycloalkyl, alkenyl, alkynyl, aryl, heterocycloalkyl, heteroaryl, and —(CR$_2$)$_q$R$^8$; or two instances of $R^7$ taken together form a 5-6 membered cycloalkyl, heterocycloalkyl, or heteroaryl;
$R^8$ for each instance is independently selected from the group consisting of —OR, —SR, —NR$_2$, —(C=O)R, —(C=O)OR, —(C=O)NR$_2$, —N(R)(C=O)R, —O(C=O)R, —N(R)(C=O)OR, —O(C=O)NR$_2$, —SO$_2$R, and —SO$_2$NR$_2$; and R for each instance is independently selected from the group consisting of hydrogen, alkyl, cycloalkyl, alkenyl, alkynyl, aryl, heterocycloalkyl, and heteroaryl; or two instances of R taken together form a 5-6 membered heterocycloalkyl or heteroaryl, wherein the compound of Formula 1 is enantiomerically enriched, and with the proviso that the compound of Formula 1 is not selected from the group consisting of:

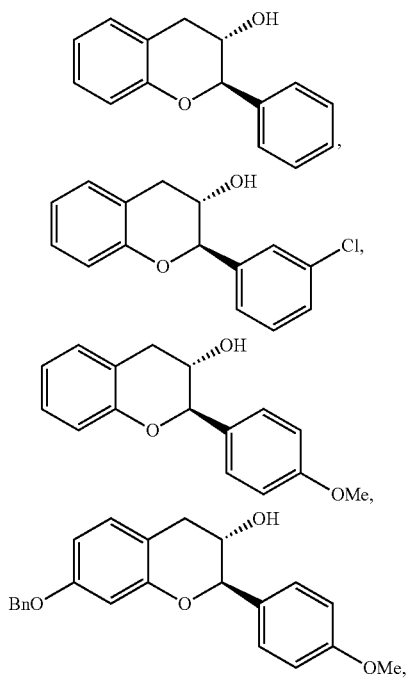

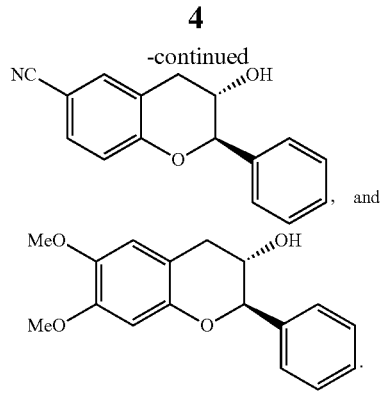

In certain embodiments, m is 1 or 2; and $R^3$ and $R^4$ are each hydrogen.
In certain embodiments, $R^2$ is —OH, —O(C=O)$R^7$, or —O(P=O)(OH)$_2$.
In certain embodiments, each of n and p is 1 and $R^6$ is hydrogen.
In certain embodiments, $R^5$ for each instance is independently selected from the group consisting of halide, methyl, chloride, fluoride, —OCH$_2$OMe, and —OH.
In certain embodiments, the compound has Formula 2:

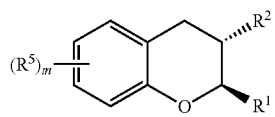

or a pharmaceutically acceptable salt thereof, wherein
m is a whole number selected from 1-2;
q is a whole number selected from 2-6;
$R^1$ is

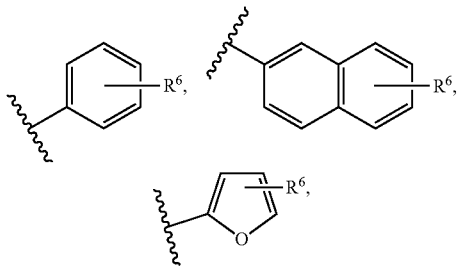

or propyl;
$R^2$ is —OR, —O(C=O)$R^7$, —O(C=O)O$R^7$, —O(C=O)N$(R^7)_2$, or —O(P=O)(OH)$_2$;
$R^5$ for each instance is independently selected from the group consisting of hydrogen, halide, nitrile, nitro, —OR, —NR$_2$, haloalkyl, perhaloalkyl, alkyl, cycloalkyl, aryl, heterocycloalkyl, heteroaryl, —OCH$_2$OMe, and —(CR$_2$)$_q$R$^8$;
$R^6$ for each instance is independently selected from the group consisting of hydrogen, halide, nitrile, nitro, —OR, —NR$_2$, haloalkyl, perhaloalkyl, alkyl, cycloalkyl, aryl, heterocycloalkyl, heteroaryl, —OCH$_2$OMe, and —(CR$_2$)$_q$R$^8$;
$R^7$ for each instance is independently selected from the group consisting of hydrogen, alkyl, cycloalkyl, alkenyl, alkynyl, aryl, heterocycloalkyl, heteroaryl, and —(CR$_2$)$_q$R$^8$; or two instances of $R^7$ taken together form a 5-6 membered cycloalkyl, heterocycloalkyl, or heteroaryl;

$R^8$ for each instance is independently selected from the group consisting of —OR, —SR, —NR$_2$, —(C═O)R, —(C═O)OR, —(C═O)NR$_2$, —N(R)(C═O)R, —O(C═O)R, —N(R)(C═O)OR, —O(C═O)NR$_2$, —SO$_2$R, and —SO$_2$NR$_2$; and R for each instance is independently selected from the group consisting of hydrogen, alkyl, cycloalkyl, alkenyl, alkynyl, aryl, heterocycloalkyl, and heteroaryl; or two instances of R taken together form a 5-6 membered heterocycloalkyl or heteroaryl.

In certain embodiments, $R^2$ is —OH and $R^6$ is hydrogen, halide, trifluoromethyl, —OCH$_2$OMe, or —OCH$_2$Ph.

In certain embodiments, $R^5$ for each instance is independently selected from the group consisting of hydrogen, methyl, —OCH$_2$OMe, halide, —OH, and —OMe.

In certain embodiments, $R^5$ for each instance is independently selected from the group consisting of hydrogen and chloride and $R^2$ is —OH.

In certain embodiments, $R^6$ is hydrogen.

In certain embodiments, the compound is selected from the group consisting of:

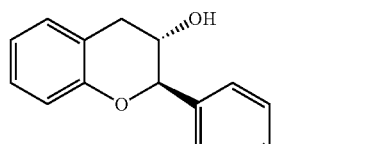

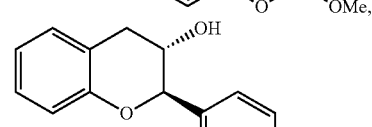

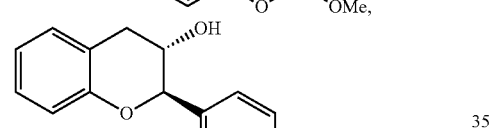

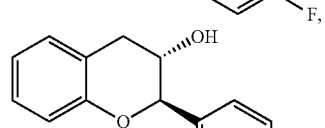

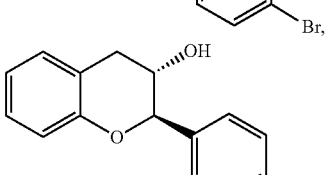

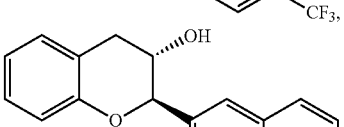

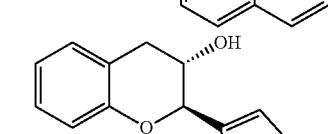

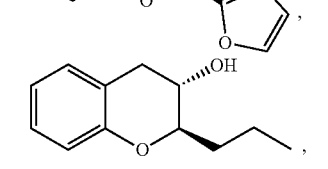

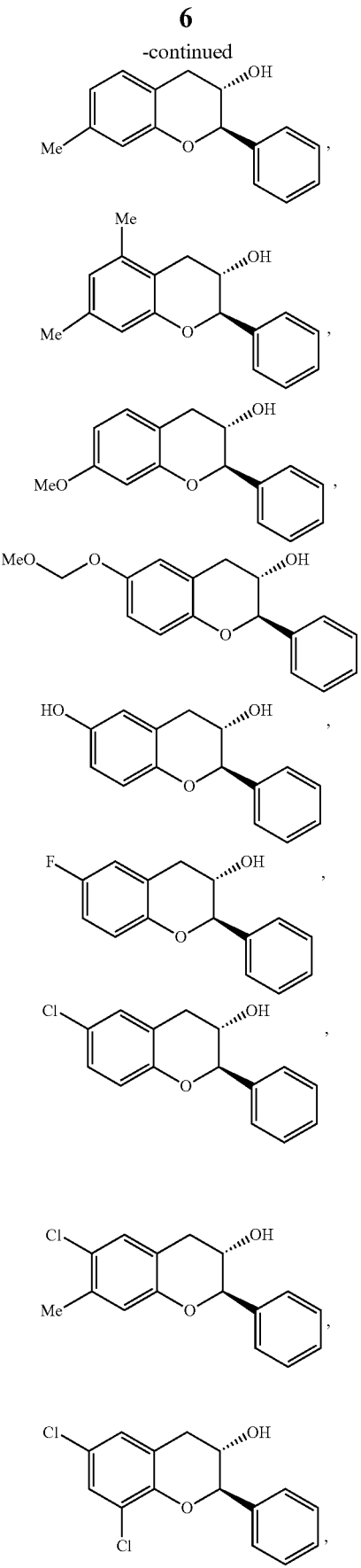

-continued

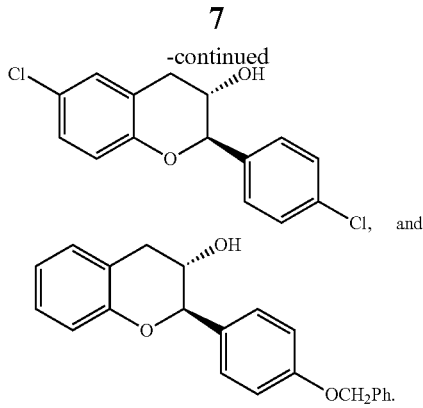

and

In certain embodiments, the compound is selected from the group consisting of:

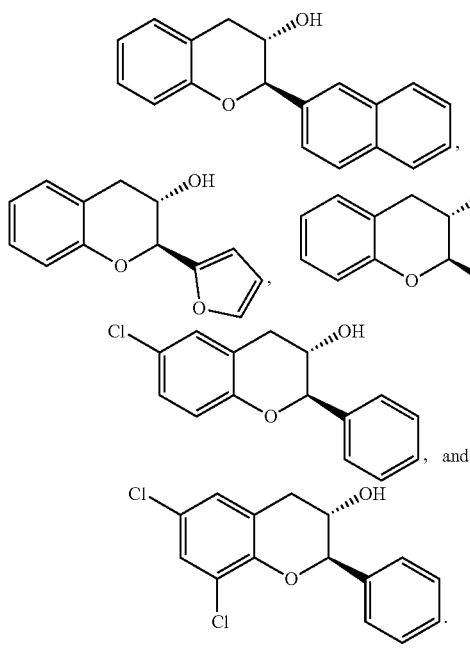

, and

In certain embodiments, the compound is:

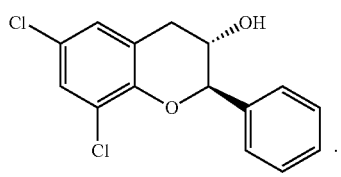 [SMILES: O[C@H]1Cc2cc(Cl)cc(Cl)c2O[C@@H]1c1ccccc1]

In a second aspect, provided herein is a pharmaceutical composition comprising the compound described herein and at least one pharmaceutically acceptable excipient or pharmaceutically acceptable carrier.

In a third aspect, provided herein is a method of treating an inflammatory disease in a subject in need thereof, the method comprising: administering a therapeutically effective amount of a compound described herein to the subject.

In certain embodiments, the compound inhibits the rate of secretion of at least one pro-inflammatory cytokine selected from the group consisting of IL-1β, IL-6, and TNF-α.

In a fourth aspect, provided herein is a method of preparing a compound described herein, the method comprising: contacting a copper complex comprising Cu(I) and a chiral bisphosphine ligand, a diborane, and a compound of Formula 5:

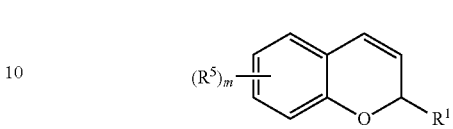

5 thereby forming a hydroborated intermediate; and contacting the hydroborated intermediate with an oxidation agent thereby forming the compound described herein, wherein the chiral bisphosphine ligand is selected from the group consisting of:

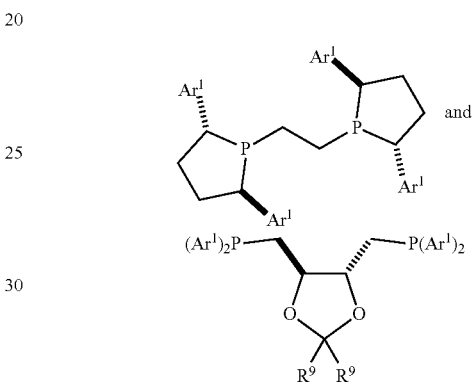

wherein $Ar^1$ is optionally substituted phenyl; and $R^9$ is alkyl; and wherein the chiral bisphosphine ligand is enantiomerically enriched.

In certain embodiments, the compound of Formula 1 has an enantiomeric excess of 97% or greater and the reaction has a conversion rate of 45-50%.

In certain embodiments, the chiral bisphosphine ligand is 1,2-bis((2R,5R)-2,5-diphenylphospholano)ethane, 1,2-bis ((2S,5S)-2,5-diphenylphospholano)ethane, (4R,5R)-(−)-4,5-bis(diphenylphosphinomethyl)-2,2-dimethyl-1,3-dioxolane, or (4S,5S)-(−)-4,5-Bis(diphenylphosphinomethyl)-2,2-dimethyl-1,3-dioxolane.

In certain embodiments, the chiral bisphosphine ligand is 1,2-bis((2R,5R)-2,5-diphenylphospholano)ethane or 1,2-bis ((2S,5S)-2,5-diphenylphospholano)ethane; the diborane is bis(pinacolato)diboron; the oxidation agent is $H_2O_2$ or $NaBO_3$; the compound of Formula 1 has an enantiomeric excess of 97% or greater; and the reaction has a conversion rate of 47-50%.

Other aspects and advantages of the present invention will be apparent to those skilled in the art from a review of the ensuing description.

BRIEF DESCRIPTION OF THE DRAWINGS

The above and other objects and features of the present invention will become apparent from the following description of the invention, when taken in conjunction with the accompanying drawings, in which:

FIG. 3A shows synthetic application of Transformation of 3a.

FIG. 4A shows the inhibition rate of each compound on the secretion of IL-1β from LPS-stimulated RAW 264.7 cells. Data from three independent experiments were expressed as means±SD. *P<0.05, **P<0.01 compared with LPS-stimulated group.

FIG. 4B shows the inhibition rate of each compound on the secretion of IL-6 from LPS-stimulated RAW 264.7 cells. Data from three independent experiments were expressed as means±SD. *P<0.05, **P<0.01 compared with LPS-stimulated group.

FIG. 4C shows the inhibition rate of each compound on the secretion of TNF-α from LPS-stimulated RAW 264.7 cells. Data from three independent experiments were expressed as means±SD. *P<0.05, **P<0.01 compared with LPS-stimulated group.

DETAILED DESCRIPTION

Definitions

Figure 1:
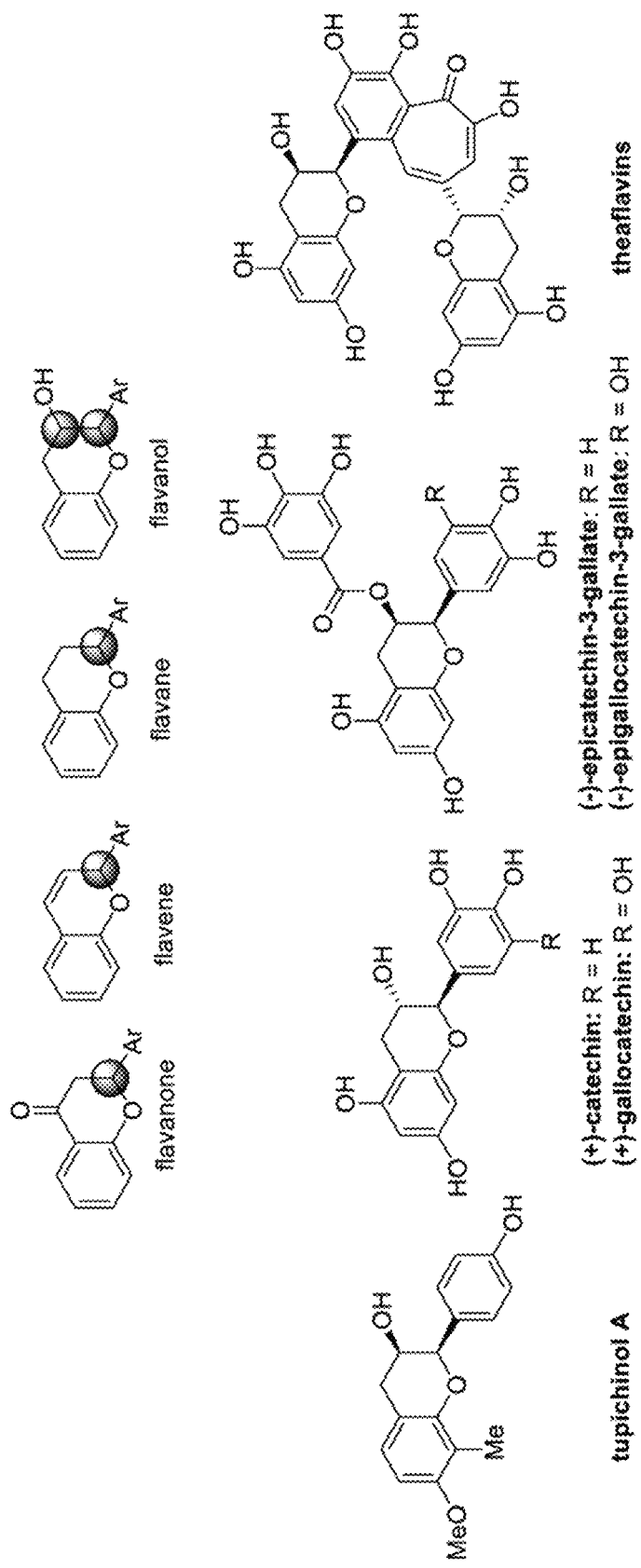
FIG. 1 shows structures of chiral flavonoid and selected examples of flavan-3-ols.
Figure 2:
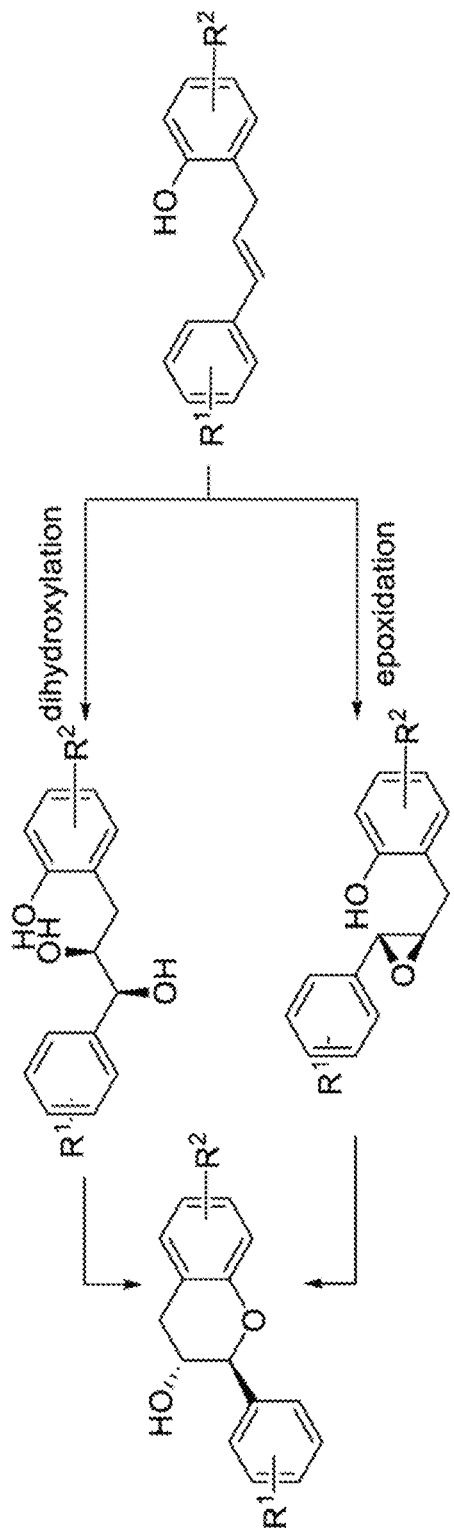
FIG. 2 shows multi-step construction of chiral flavan-3-ols (top); and highly efficient kinetic resolution of 2H-chromenes by Cu-catalyzed asymmetric hydroboration (bottom).
Figure 2:
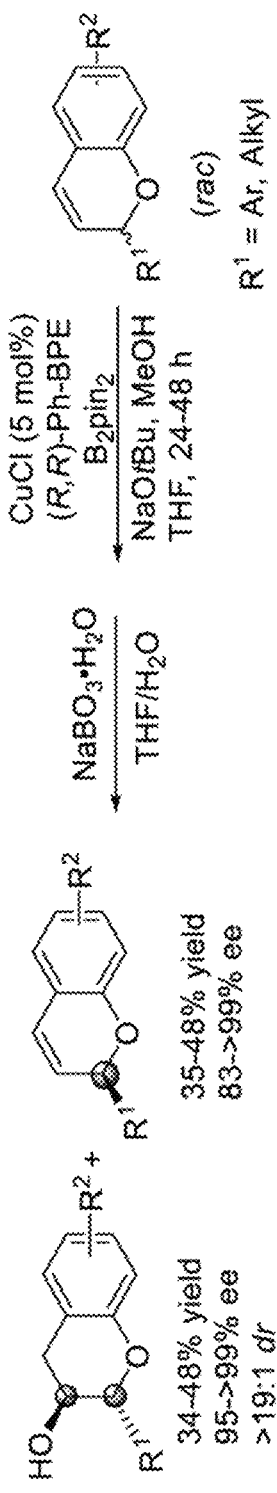
Figure 3A:
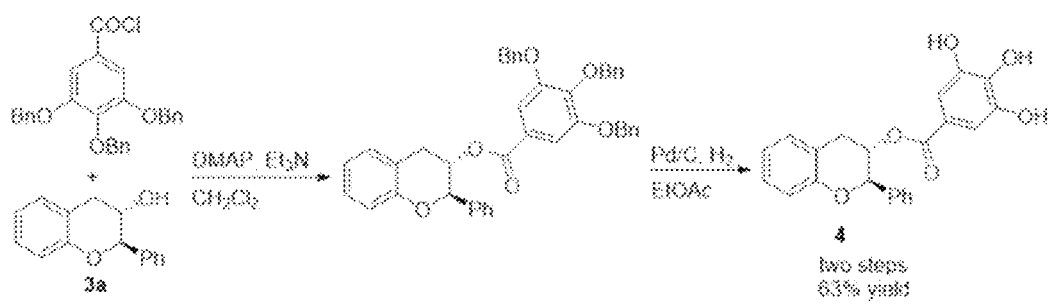
Figure 3B:
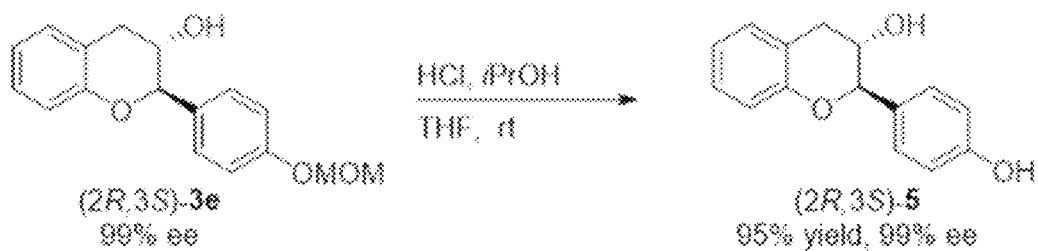
FIG. 3B shows synthetic application of Deprotection of MOM of 3e.

Throughout the present specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the present invention.

Furthermore, throughout the present specification and claims, unless the context requires otherwise, the word "include" or variations such as "includes" or "including", will be understood to imply the inclusion of a stated integer or group of integers but not the exclusion of any other integer or group of integers.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10%, ±7%, ±5%, ±3%, ±1%, or ±0% variation from the nominal value unless otherwise indicated or inferred.

As used herein, the terms "treat", "treating", "treatment", and the like refer to reducing or ameliorating a disorder/disease and/or symptoms associated therewith. It will be appreciated, although not precluded, treating a disorder or condition does not require that the disorder, condition, or symptoms associated therewith be completely eliminated. In certain embodiments, treatment includes prevention of a disorder or condition, and/or symptoms associated therewith. The term "prevention" or "prevent" as used herein refers to any action that inhibits or at least delays the development of a disorder, condition, or symptoms associated therewith. Prevention can include primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

The term "subject" as used herein, refers to an animal, typically a mammal or a human, that will be or has been the object of treatment, observation, and/or experiment. When the term is used in conjunction with administration of a compound described herein, then the subject has been the object of treatment, observation, and/or administration of the compound described herein.

The term "therapeutically effective amount" as used herein, means that amount of the compound or pharmaceutical agent that elicits a biological and/or medicinal response in a cell culture, tissue system, subject, animal, or human that is being sought by a researcher, veterinarian, clinician, or physician, which includes alleviation of the symptoms of the disease, condition, or disorder being treated.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "composition" is intended to encompass a product comprising the specified ingredients in the specified amounts, as well as any product that results, directly or indirectly, from combinations of the specified ingredients in the specified amounts.

The term "pharmaceutically acceptable carrier" refers to a medium that is used to prepare a desired dosage form of a compound. A pharmaceutically acceptable carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe ed. (American Pharmaceutical Assoc. 2000), disclose various carriers used in formulating pharmaceutical compositions and known techniques for the preparation thereof.

As used herein, unless otherwise indicated, the term "halo" or "halide" includes fluoro, chloro, bromo or iodo.

As used herein, "alkyl" refers to a straight-chain or branched saturated hydrocarbon group. Examples of alkyl groups include methyl-, ethyl-, propyl (e.g., n-propyl and isopropyl), butyl (e.g., n-butyl, iso-butyl, sec-butyl, tert-butyl), pentyl groups (e.g., 1-methylbutyl, 2-methylbutyl, iso-pentyl, tert-pentyl, 1,2-dimethylpropyl, neopentyl, and 1-ethylpropyl), hexyl groups, and the like. In various embodiments, an alkyl group can have 1 to 40 carbon atoms (i.e., $C_1$-$C_{40}$ alkyl group), for example, 1-30 carbon atoms (i.e., $C_1$-$C_{30}$ alkyl group). In certain embodiments, an alkyl group can have 1 to 6 carbon atoms, and can be referred to as a "lower alkyl group." Examples of lower alkyl groups include methyl, ethyl, propyl (e.g., n-propyl and isopropyl), and butyl groups (e.g., n-butyl, isobutyl, sec-butyl, tert-butyl). In certain embodiments, alkyl groups can be optionally substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_2$-$C_{40}$ alkenyl group), for example, 2 to 20 carbon atoms (i.e., $C_2$-$C_{20}$ alkenyl group). In certain embodiments, alkenyl groups can be substituted as described herein. An alkenyl group is generally not substituted with another alkenyl group, an alkyl group, or an alkynyl group.

As used herein, "cycloalkyl" by itself or as part of another substituent means, unless otherwise stated, a monocyclic hydrocarbon having between 3-12 carbon atoms in the ring system and includes hydrogen, straight chain, branched chain, and/or cyclic substituents. Exemplary cycloalkyls include cyclopropyl, cyclobutyl, cyclopentyl, cyclohexyl, cycloheptyl, and the like.

As used herein, a "fused ring" or a "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly p-conjugated and optionally substituted as described herein.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_6$-$C_{24}$ aryl group), which can include multiple fused rings. In certain embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In certain embodiments, aryl groups can be optionally substituted. In certain embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be optionally substituted.

The term "aralkyl" refers to an alkyl group substituted with an aryl group.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), $SiH_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In certain embodiments, heteroaryl groups can be substituted as described herein. In certain embodiments, heteroaryl groups can be optionally substituted.

The term "heterocycloalkyl" as used herein includes reference to a saturated heterocyclic moiety having 3, 4, 5, 6 or 7 ring carbon atoms and 1, 2, 3, 4 or 5 ring heteroatoms selected from nitrogen, oxygen, phosphorus and sulfur. The group may be a polycyclic ring system but more often is monocyclic. This term includes reference to groups such as azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolizidinyl and the like.

The term "optionally substituted" refers to a chemical group, such as alkyl, cycloalkyl aryl, and the like, wherein one or more hydrogen may be replaced with a substituent as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like The term "carbocycle" is art-recognized and refers to an aromatic or non-aromatic ring in which each atom of the ring is carbon.

The term "nitro" is art-recognized and refers to —$NO_2$; the term "halogen" is art-recognized and refers to —F, —Cl, —Br or —I; the term "sulfhydryl" is art-recognized and refers to —SH; the term "hydroxyl" means —OH; and the term "sulfonyl" and "sulfone" is art-recognized and refers to —$SO_2$—. "Halide" designates the corresponding anion of the halogens.

As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J. Pharmaceutical Sciences (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In certain embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Enantiomers" are a pair of stereoisomers that are non-superimposable mirror images of each other. A mixture of a pair of enantiomers in equal proportions can be known as a "racemic" mixture. The term "(+/−)" is used to designate a racemic mixture where appropriate. The absolute stereochemistry can be specified according to the Cahn-Ingold-Prelog R-S system. When a compound is an enantiomer, the stereochemistry at each chiral carbon and/or axis of chirality can be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein can contain one or more asymmetric centers and/or axis of chirality and can thus give rise to enantiomers, diastereomers, and other stereoisomeric forms that can be defined, in terms of absolute stereochemistry at each asymmetric atom or axis of chirality, as (R)- or (S)—. The present compounds and methods are meant to include all such possible isomers, including substantially enantiopure forms and intermediate mixtures. Optically active (R)- and (S)-isomers can be prepared, for example, using chiral synthons or chiral reagents, or resolved using conventional techniques.

The "enantiomeric excess" or "% enantiomeric excess" of a composition can be calculated using the equation shown below. In the example shown below, a composition contains 90% of one enantiomer, e.g., an S enantiomer, and 10% of the other enantiomer, e.g., an R enantiomer. ee=(90-10)/100=80%.

Thus, a composition containing 90% of one enantiomer and 10% of the other enantiomer is said to have an enantiomeric excess of 80%. Some compositions described herein contain an enantiomeric excess of at least about 1%, about 5%, about 10%, about 20%, about 30%, about 40%, about 50%, about 75%, about 90%, about 95%, about 99%, or greater of the S enantiomer. In other words, the compositions contain an enantiomeric excess of the S enantiomer over the R enantiomer. In other embodiments, some compositions described herein contain an enantiomeric excess of at least about 1%, about 5%, about 10%, about 20%, about 30%, about 40%, about 50%, about 75%, about 90%, about 95%, about 99%, or greater of the R enantiomer. In other words, the compositions contain an enantiomeric excess of the R enantiomer over the S enantiomer.

For instance, an enantiomer can, in some embodiments, be provided substantially free of the corresponding enantiomer, and can also be referred to as "optically enriched," "enantiomerically enriched," "enantiomerically pure", "substantially enantiopure" and "non-racemic," as used interchangeably herein. These terms refer to compositions in which the amount of one enantiomer is greater than the amount of that one enantiomer in a control mixture of the racemic composition (e.g., greater than 1:1 by weight). For example, an enantiomerically enriched preparation of the S enantiomer, means a preparation of the compound having greater than about 50% by weight of the S enantiomer relative to the total weight of the preparation (e.g., total weight of S and R isomers), such as at least about 75% by weight, further such as at least about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have at least about 70% by weight of one enantiomer relative to the total weight of the preparation, such as at as at least about 75% by weight, such as at as at least about 80% by weight, such as at as at least about 85% by weight, such as at least about 90% by weight, and such as at least about 95% by weight. In certain embodiments, the compound provided herein is made up of at least about 90% by weight of one enantiomer. In other embodiments, the compound is made up of at least about 95%, about 98%, or about 99% by weight of one enantiomer.

In some embodiments, the compound is a racemic mixture of (S)- and (R) isomers. In other embodiments, provided herein is a mixture of compounds wherein individual compounds of the mixture exist predominately in an (S)- or (R)-isomeric configuration. For example, in some embodiments, the compound mixture has an (S)-enantiomeric excess of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, greater than about 96%, greater than about 97%, greater than about 98%, or greater than about 99%. In some embodiments, the compound mixture has an (S)-enantiomeric excess of about 55%, about 60%, about 65%, about 70%, about 75%, about 80%, about 85%, about 90%, about 95%, about 96%, about 97%, about 98%, about 99%, or about 99.5%, or more. In some embodiments, the compound mixture has an (S)-enantiomeric excess of about 55% to about 99.5%, about 60% to about 99.5%, about 65% to about 99.5%, about 70% to about 99.5%, about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%.

In other embodiments, the compound mixture has an (R)-enantiomeric excess of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, greater than about 96%, greater than about 97%, greater than about 98%, or greater than about 99%. In some embodiments, the compound mixture has an (R)-enantiomeric excess of about 55%, about 60%, about 65%, about 70%, about 75%, about 80%, about 85%, about 90%, about 95%, about 96%, about 97%, about 98%, about 99%, or about 99.5%, or more. In some embodiments, the compound mixture has an (R)-enantiomeric excess of about 55% to about 99.5%, about 60% to about 99.5%, about 65% to about 99.5%, about 70% to about 99.5%, about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%.

Wedge-shaped bonds such as ╲ and ╱ in the chemical structures described herein are intended to depict absolute stereochemistry. Whereas, straight bonds such as ╱ and ╲ in the chemical structures described herein are intended to depict relative stereochemistry. Where a chemical structure does not explicitly depict relative and/or absolute stereochemistry of one more stereogenic centers present in a compound, the chemical structures encompasses all enantiomers and/or diastereomers.

The representation " ⁂ " as used herein in connection to chemical a group or moiety is intended to represent the covalent bond that the aforementioned chemical group or moiety is covalently bonded to another chemical group or moiety.

Pharmaceutically acceptable salts derived from appropriate bases include alkali metal, alkaline earth metal, ammonium and N+($C_{14}$alkyl)$_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, non-toxic ammonium, quaternary ammonium, and amine cations formed using counterions, such as halide, hydroxide, carboxylate, sulfate, phosphate, nitrate, lower alkyl sulfonate, and aryl sulfonate. Organic bases from which salts can be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In certain embodiments, the pharmaceutically acceptable base addition salt is chosen from ammonium, potassium, sodium, calcium, and magnesium salts.

Other definitions for selected terms used herein may be found within the detailed description of the present invention and apply throughout. Unless otherwise defined, all other technical terms used herein have the same meaning as commonly understood to one of ordinary skill in the art to which the invention belongs.

Provided herein are flavan-3-ols and analogs thereof that suppress the expression and secretion of pro-inflammation cytokines, such as IL-1, IL-6 and TNF-α. These compounds may inhibit inflammation responses through downregulating the gene transcriptions closely related to IL-17 signaling pathway, PI3K-Akt signaling pathway and TNF signaling pathway, which indicates that the compounds disclosed herein are potent lead compounds for treating inflammation diseases.

The flavan-3-ols and analogs thereof can be represented by a compound of Formula 1:

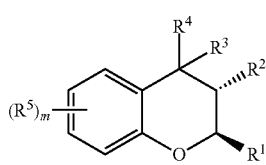

1 or a pharmaceutically acceptable salt thereof, wherein
m is a whole number selected from 1-3;
n is a whole number selected from 1-3;
p is a whole number selected from 1-2;
q is a whole number selected from 2-6;
$R^1$ is

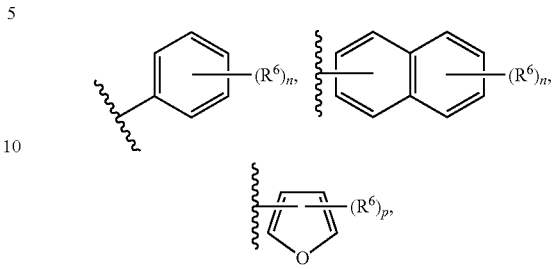

or propyl;
$R^2$ is —OR, —O(C=O)$R^7$, —O(C=O)O$R^7$, —O(C=O)N($R^7$)$_2$, or —O(P=O)(OH)$_2$;
each of $R^3$ and $R^4$ is independently hydrogen, alkyl, aryl, heteroaryl, —OR, or —O(C=O)$R^7$; or
$R^3$ and $R^4$ taken together with the carbon to which they are covalently bonded form (C=O);
$R^5$ for each instance is independently selected from the group consisting of hydrogen, halide, nitrile, nitro, —OR, —SR, —N$R_2$, —(C=O)R, —(C=O)OR, —(C=O)N$R_2$, —N(R)(C=O)R, —O(C=O)R, —N(R)(C=O)OR, —O(C=O)N$R_2$, —SO$_2$R, —SO$_2$N$R_2$, haloalkyl, perhaloalkyl, alkyl, cycloalkyl, alkenyl, alkynyl, aryl, heterocycloalkyl, heteroaryl, —OCH$_2$OMe, and —(C$R_2$)$_q$$R^8$; or two instances of $R^5$ taken together form a 5-6 membered cycloalkyl, heterocycloalkyl, aryl, or heteroaryl;
$R^6$ for each instance is independently selected from the group consisting of hydrogen, halide, nitrile, nitro, —OR, —SR, —N$R_2$, —(C=O)R, —(C=O)OR, —(C=O)N$R_2$, —N(R)(C=O)R, —O(C=O)R, —N(R)(C=O)OR, —O(C=O)N$R_2$, —SO$_2$R, —SO$_2$N$R_2$, haloalkyl, perhaloalkyl, alkyl, cycloalkyl, alkenyl, alkynyl, aryl, heterocycloalkyl, heteroaryl, and —(C$R_2$)$_q$$R^8$;
$R^7$ for each instance is independently selected from the group consisting of hydrogen, alkyl, cycloalkyl, alkenyl, alkynyl, aryl, heterocycloalkyl, heteroaryl, —OCH$_2$OMe, and —(C$R_2$)$_q$$R^8$; or two instances of $R^7$ taken together form a 5-6 membered cycloalkyl, heterocycloalkyl, or heteroaryl;
$R^8$ for each instance is independently selected from the group consisting of —OR, —SR, —N$R_2$, —(C=O)R, —(C=O)OR, —(C=O)N$R_2$, —N(R)(C=O)R, —O(C=O)R, —N(R)(C=O)OR, —O(C=O)N$R_2$, —SO$_2$R, and —SO$_2$N$R_2$; and
R for each instance is independently selected from the group consisting of hydrogen, alkyl, cycloalkyl, alkenyl, alkynyl, aryl, heterocycloalkyl, and heteroaryl; or two instances of R taken together form a 5-6 membered heterocycloalkyl or heteroaryl, wherein the compound of Formula 1 or a composition comprising the same is enantiomerically.

In certain embodiments, the compound of Formula 1 is not selected from the group consisting of:

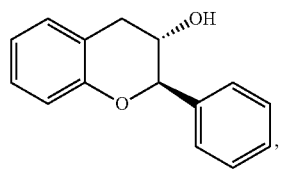

-continued

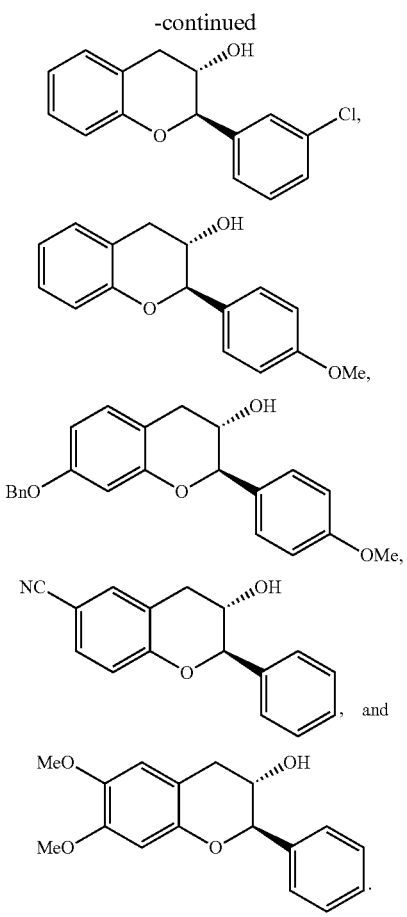

In instances in which R¹ is a naphthyl or furan moiety, the moiety can be selected from the group consisting of:

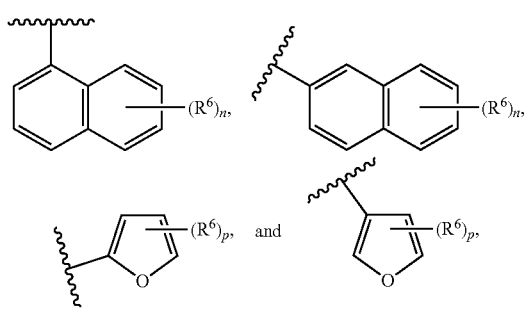

wherein R⁶ can be covalently bonded to either or both rings of the naphthyl moiety.

In certain embodiments, R¹ is selected from the group consisting of:

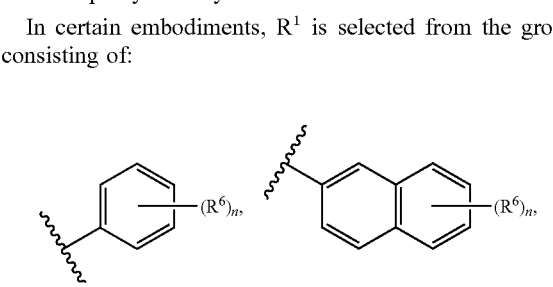

-continued

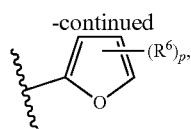

and propyl,
wherein n is 1 or 2.

$R^2$ can be selected from —OH, —OR, —O(C=O)$R^7$, and —O(C=O)N($R^7$)$_2$, wherein $R^7$ for each instance is independently selected from the group consisting of hydrogen, alkyl, aryl, heterocycloalkyl, heteroaryl, and —(CR$_2$)$_q$$R^8$; or two instances of $R^7$ taken together form a 5-6 membered heteroaryl and R is alkyl, aryl, heterocycloalkyl, or heteroaryl. In certain embodiments, $R^2$ is —OH.

In certain embodiments, each of $R^3$ and $R^4$ is hydrogen; $R^3$ is —OH and $R^4$ is hydrogen; or $R^3$ and $R^4$ taken together with the carbon to which they are covalently bonded form (C=O). In certain embodiments, each of $R^3$ and $R^4$ is hydrogen.

$R^5$ for each instance can independently be hydrogen, halide, nitrile, nitro, —OR, —NR$_2$, —(C=O)R, —(C=O)NR$_2$, —O(C=O)R, haloalkyl, such as a fluoroalkyl (e.g., —CH$_2$F or —CHF$_2$), perhaloalkyl, such as a perflouoroalkyl (—CF$_3$), alkyl, cycloalkyl, aryl, heterocycloalkyl, heteroaryl, —OCH$_2$OMe, or —(CR$_2$)$_q$$R^8$. In certain embodiments, $R^5$ for each instance is independently hydrogen, methyl, chloride, fluoride, —OMe, or —OCH$_2$OMe. In certain embodiments, $R^5$ for each instance is independently hydrogen or chloride.

$R^6$ for each instance can independently be hydrogen, halide, nitrile, nitro, —OR, —NR$_2$, —(C=O)R, —(C=O)NR$_2$, —O(C=O)R, haloalkyl, such as a fluoroalkyl (e.g., —CH$_2$F or —CHF$_2$), perhaloalkyl, such as a perflouoroalkyl (—CF$_3$), alkyl, cycloalkyl, aryl, heterocycloalkyl, heteroaryl, —OCH$_2$OMe, or —(CR$_2$)$_q$$R^8$. In certain embodiments, $R^6$ for each instance is independently hydrogen, methyl, fluoride, chloride, bromide, —CF$_3$, —OMe, —OCH$_2$Ph, or —OCH$_2$OMe. In certain embodiments, $R^6$ is hydrogen.

In certain embodiments, the compound has Formula 2:

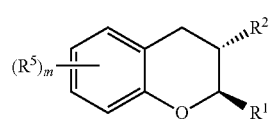

2 or a pharmaceutically acceptable salt thereof, wherein
m is a whole number selected from 1-2;
q is a whole number selected from 2-6;
R¹ is

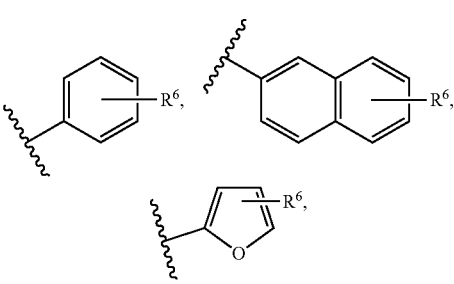

or propyl;
R² is —OR, —O(C=O)R⁷, —O(C=O)OR⁷, —O(C=O)N(R⁷)₂, or —O(P=O)(OH)₂;
R⁵ for each instance is independently selected from the group consisting of hydrogen, halide, nitrile, nitro, —OR, —NR₂, haloalkyl, perhaloalkyl, alkyl, cycloalkyl, aryl, heterocycloalkyl, heteroaryl, and —(CR₂)$_q$R⁸;
R⁶ for each instance is independently selected from the group consisting of hydrogen, halide, nitrile, nitro, —OR, —NR₂, haloalkyl, perhaloalkyl, alkyl, cycloalkyl, aryl, heterocycloalkyl, heteroaryl, and —(CR₂)$_q$R⁸;
R⁷ for each instance is independently selected from the group consisting of hydrogen, alkyl, cycloalkyl, alkenyl, alkynyl, aryl, heterocycloalkyl, heteroaryl, and —(CR₂)$_q$R⁸; or two instances of R⁷ taken together form a 5-6 membered cycloalkyl, heterocycloalkyl, or heteroaryl;
R⁸ for each instance is independently selected from the group consisting of —OR, —SR, —NR₂, —(C=O)R, —(C=O)OR, —(C=O)NR₂, —N(R)(C=O)R, —O(C=O)R, —N(R)(C=O)OR, —O(C=O)NR₂, —SO₂R, and —SO₂NR₂; and R for each instance is independently selected from the group consisting of hydrogen, alkyl, cycloalkyl, alkenyl, alkynyl, aryl, heterocycloalkyl, and heteroaryl; or two instances of R taken together form a 5-6 membered heterocycloalkyl or heteroaryl.

In certain embodiments, the compound is selected from the group consisting of:

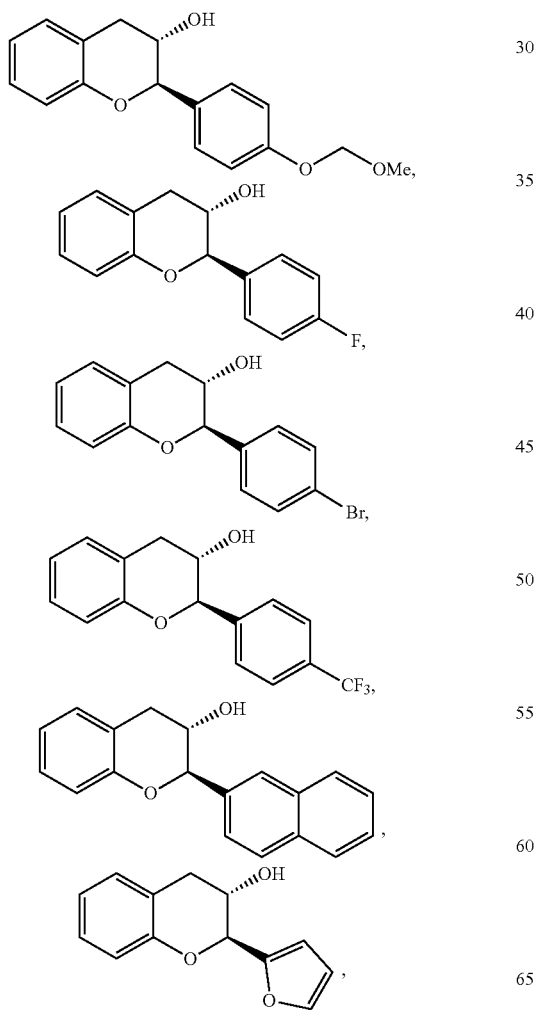

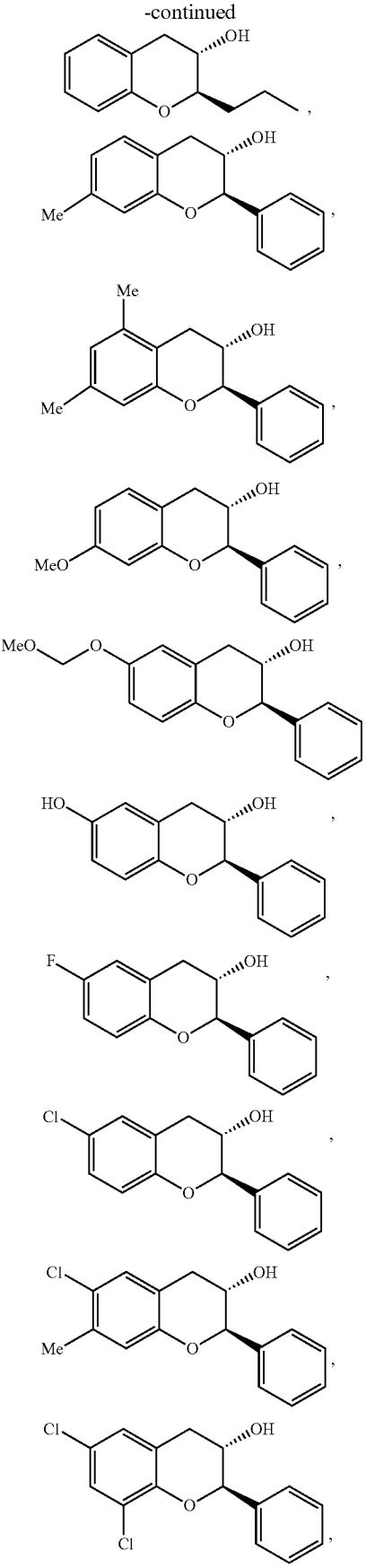

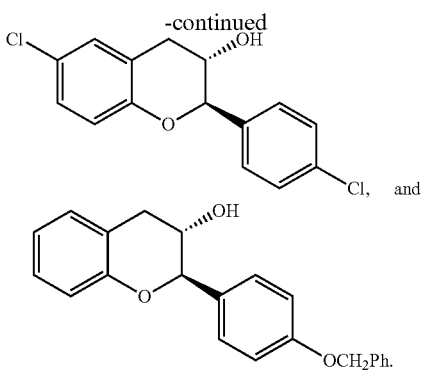

In certain embodiments, the compound is selected from the group consisting of:

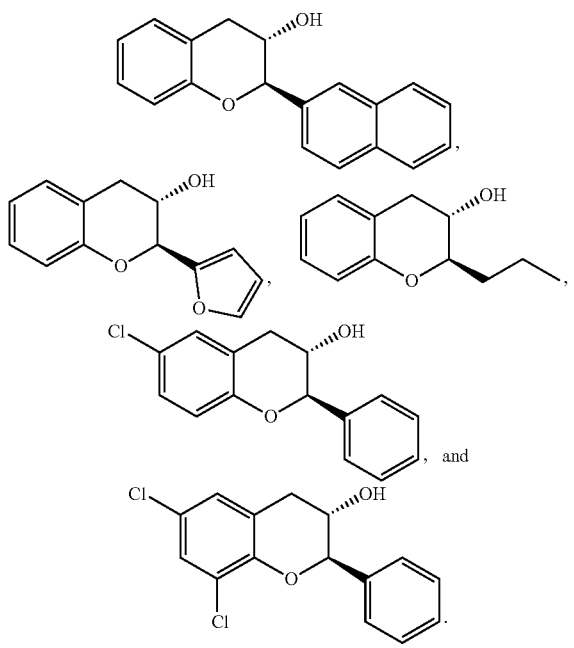

The compound may be present in a composition comprising the compound with an enantiomeric excess of at least 90%, at least 95%, at least 97%, at least 99%, at least 99.5%, or at least 99.9%. In certain embodiments, the composition comprises the compound with an enantiomeric excess is 90-99.9%, 91-99.9%, 92-99.9%, 93-99.9%, 94-99.9%, 94-99.9%, 95-99.9%, 96-99.9%, 97-99.9%, 98-99.9%, 99-99.9%, 99-99.7%, or 99-99.5% enantiomeric excess. In certain embodiments, the composition is a pharmaceutical composition.

The compound may be present in a composition comprising the compound with a diastereomeric excess of at least 90%, at least 95%, at least 97%, at least 99%, at least 99.5%, or at least 99.9%. In certain embodiments, the composition comprises the compound with an diastereomeric excess is 90-99.9%, 91-99.9%, 92-99.9%, 93-99.9%, 94-99.9%, 94-99.9%, 95-99.9%, 96-99.9%, 97-99.9%, 98-99.9%, 99-99.9%, 99-99.7%, 99-99.5%, 95-99.5%, 95-99%, 95-98%, 95-97%, or 95-96% diastereomeric excess. In certain embodiments, the composition is a pharmaceutical composition.

The present disclosure also provides a pharmaceutical composition comprising a compound described herein and at least one pharmaceutically acceptable excipient and/or pharmaceutically acceptable carrier.

The compounds described herein and their pharmaceutically acceptable salts can be administered to a subject either alone or in combination with pharmaceutically acceptable carriers or diluents in a pharmaceutical composition according to standard pharmaceutical practice. The compounds can be administered orally or parenterally. Parenteral administration includes intravenous, intramuscular, intraperitoneal, subcutaneous and topical, the preferred method being intravenous administration.

Accordingly, the present disclosure provides pharmaceutically acceptable compositions, which comprise a therapeutically-effective amount of one or more of the compounds described herein, formulated together with one or more pharmaceutically acceptable carriers (additives) and/or diluents. The pharmaceutical compositions of the present disclosure may be specially formulated for administration in solid or liquid form, including those adapted for the following: (1) parenteral administration, for example, by subcutaneous, intramuscular, intravenous or epidural injection as, for example, a sterile solution or suspension, or sustained-release formulation; and (2) oral administration, for example, drenches (aqueous or non-aqueous solutions or suspensions), tablets, e.g., those targeted for buccal, sublingual, and systemic absorption, boluses, powders, granules, pastes for application to the tongue.

As set out herein, certain embodiments of the compounds described herein may contain a basic functional group, such as amino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present disclosure. These salts can be prepared in situ in the administration vehicle or the dosage form manufacturing process, or by separately reacting a purified compound described herein in its free base form with a suitable organic or inorganic acid, and isolating the salt thus formed during subsequent purification. Representative salts include the bromide, chloride, sulfate, bisulfate, carbonate, bicarbonate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

The pharmaceutically acceptable salts of the compounds of the present disclosure include the conventional nontoxic salts or quaternary ammonium salts of the compounds, e.g., from nontoxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compound described herein may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds described herein. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives, solubilizing agents, buffers and antioxidants can also be present in the compositions.

Methods of preparing the pharmaceutical comprising the compound described herein include the step of bringing into association a compound described herein with the carrier and, optionally, one or more accessory ingredients. In general, the formulations are prepared by uniformly and intimately bringing into association a compound described herein with liquid carriers (liquid formulation), liquid carriers followed by lyophilization (powder formulation for reconstitution with sterile water or the like), or finely divided solid carriers, or both, and then, if necessary, shaping or packaging the product.

Pharmaceutical compositions of the present disclosure suitable for parenteral administration can comprise one or more compound described herein in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, chelating agents, solutes which render the formulation isotonic with the blood of the intended recipient or suspending or thickening agents. In the examples, the active ingredients are brought together with the pharmaceutically acceptable carriers in solution and then lyophilized to yield a dry powder. The dry powder is packaged in unit dosage form and then reconstituted for parental administration by adding a sterile solution, such as water or normal saline, to the powder.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms upon the compounds described herein may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The method of preparing the compounds described herein is not particularly limited. The compounds can be prepared using well-known synthetic methodologies in the art. Provided herein is a method of preparing a compound of Formula 4:

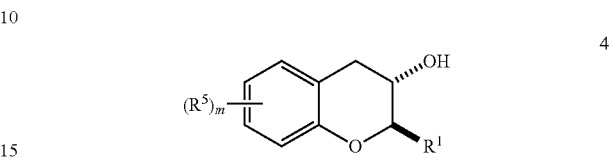

or a pharmaceutically acceptable salt thereof, wherein
m is a whole number selected from 1-3;
q is a whole number selected from 2-6;
$R^1$ is alkyl, aryl, or heteraryl;
$R^5$ for each instance is independently selected from the group consisting of hydrogen, halide, nitrile, nitro, —OR, —SR, —NR$_2$, —(C=O)R, —(C=O)OR, —(C=O)NR$_2$, —N(R)(C=O)R, —O(C=O)R, —N(R)(C=O)OR, —O(C=O)NR$_2$, —SO$_2$R, —SO$_2$NR$_2$, haloalkyl, perhaloalkyl, alkyl, cycloalkyl, alkenyl, alkynyl, aryl, heterocycloalkyl, heteroaryl, and —(CR$_2$)$_q$R$^8$; or two instances of $R^5$ taken together form a 5-6 membered cycloalkyl, heterocycloalkyl, aryl, or heteroaryl;
$R^8$ for each instance is independently selected from the group consisting of —OR, —SR, —NR$_2$, —(C=O)R, —(C=O)OR, —(C=O)NR$_2$, —N(R)(C=O)R, —O(C=O)R, —N(R)(C=O)OR, —O(C=O)NR$_2$, —SO$_2$R, and —SO$_2$NR$_2$; and R for each instance is independently selected from the group consisting of hydrogen, alkyl, cycloalkyl, alkenyl, alkynyl, aryl, heterocycloalkyl, and heteroaryl; or two instances of R taken together form a 5-6 membered heterocycloalkyl or heteroaryl, the method comprising: contacting a copper complex comprising Cu(I) and a chiral bisphosphine ligand, a diborane, and a compound of Formula 5:

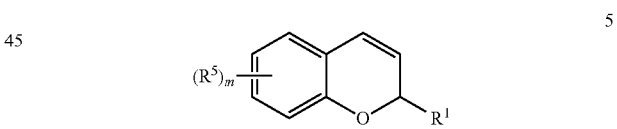

thereby forming a hydroborated intermediate; and contacting the hydroborated intermediate with an oxidation agent thereby forming the compound of Formula 4.

In certain embodiments of preparing the compound of Formula 4, $R^1$ is:

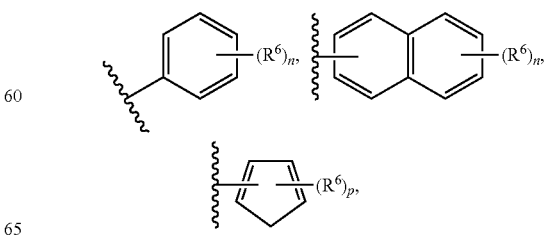

or propyl;
n is a whole number selected from 1-3; p is a whole number selected from 1-2; and $R^6$ for each instance is independently selected from the group consisting of hydrogen, halide, nitrile, nitro, —OR, —SR, —$NR_2$, —(C=O)R, —(C=O)OR, —(C=O)$NR_2$, —N(R)(C=O)R, —O(C=O)R, —N(R)(C=O)OR, —O(C=O)$NR_2$, —$SO_2$R, —$SO_2NR_2$, haloalkyl, perhaloalkyl, alkyl, cycloalkyl, alkenyl, alkynyl, aryl, heterocycloalkyl, heteroaryl, —$OCH_2OMe$, and —$(CR_2)_qR^8$.

In certain embodiments of preparing the compound of Formula 4, the compound of Formula 5 is racemic; and the compound of Formula 4 has an enantiomeric excess of 90% or greater.

In certain embodiments of preparing the compound of Formula 4, the compound of Formula 5 has an enantiomeric excess of 97% or greater.

In certain embodiments of preparing the compound of Formula 4, the reaction has a conversion rate of 45-50%.

In certain embodiments of preparing the compound of Formula 4, the step of contacting the copper complex comprising Cu(I) and the chiral bisphosphine ligand; the diborane; and the compound of Formula 5 is conducted at a temperate of −35° C. to 0° C.

In certain embodiments of preparing the compound of Formula 4, $Ar^1$ is a moiety having the Formula 6:

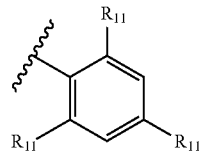

6 wherein $R^{11}$ for each instance is independently selected from the group consisting of hydrogen, halide, ether, alkyl, cycloalkyl, aryl, and trialkylsilane.

In certain embodiments of preparing the compound of Formula 4, $Ar^1$ is phenyl.

In certain embodiments of preparing the compound of Formula 4, the chiral bisphosphine ligand is 1,2-bis((2R,5R)-2,5-diphenylphospholano)ethane,1,2-bis((2S,5S)-2,5-diphenylphospholano)ethane, (4R,5R)-(−)-4,5-bis(diphenylphosphinomethyl)-2,2-dimethyl-1,3-dioxolane, or (4S,5S)-(−)-4,5-Bis(diphenylphosphinomethyl)-2,2-dimethyl-1,3-dioxolane.

In certain embodiments of preparing the compound of Formula 4, the oxidation agent is selected from the group consisting of $H_2O_2$, tBuOOH, and $NaBO_3$.

In certain embodiments of preparing the compound of Formula 4, the method further comprises the step of isolating a compound of Formula 7:

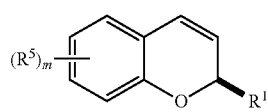

7 wherein the compound of Formula 7 is enantiomerically enriched.

In certain embodiments of preparing the compound of Formula 4, the compound of Formula 7 has an enantiomeric excess of 97% or greater.

In certain embodiments of preparing the compound of Formula 4, the chiral bisphosphine ligand is 1,2-bis((2R,5R)-2,5-diphenylphospholano)ethane or 1,2-bis((2S,5S)-2,5-diphenylphospholano)ethane; the diborane is bis(pinacolato)diboron; the oxidation agent is $H_2O_2$ or $NaBO_3$; the compound of Formula 4 has an enantiomeric excess of 97% or greater; and the reaction has a conversion rate of 47-50%.

The copper complex can be prepared in situ by combining a copper (I) salt and the chiral bisphosphine ligand.

Any copper (I) salt can be used in the methods described herein. Exemplary copper (I) salts include, but are not limited to, copper (I) chloride, copper (I) bromide, copper (I) iodide, copper (I) sulfate, and copper (I) cyanide. In certain embodiments, the copper (I) salt is copper (I) chloride.

In the alternative, any source of copper (I) can be used. For example, copper (0) can be used and oxidized in situ in the reaction with the appropriate oxidant or a copper (II) salt can be used and the copper (I) salt form therefrom by reaction with the appropriate reductant.

The selection of the chiral bisphosphine ligand is not particularly limited. A person of ordinary skill in the art can screen and select the appropriate chiral bisphosphine ligand based on the teachings described herein and common knowledge in the art. In certain embodiments, the chiral bisphosphine ligand is selected from the group consisting of:

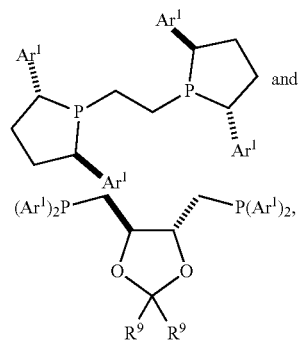

wherein $Ar^1$ is optionally substituted phenyl; and $R^9$ is alkyl; and wherein the compound of Formula 4 and the chiral bisphosphine ligand are enantiomerically enriched. In certain embodiments, $Ar^1$ is a moiety having the Formula 6:

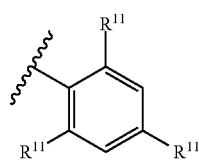

6 wherein $R^{11}$ for each instance is independently selected from the group consisting of hydrogen, halide, ether, alkyl, cycloalkyl, aryl, and trialkylsilane.

In certain embodiments, the chiral bisphosphine is 1,2-bis((2R,5R)-2,5-diphenylphospholano)ethane,1,2-bis((2S,5S)-2,5-diphenylphospholano)ethane, (4R,5R)-(−)-4,5-bis(diphenylphosphinomethyl)-2,2-dimethyl-1,3-dioxolane, or (4S,5S)-(−)-4,5-Bis(diphenylphosphinomethyl)-2,2-dimethyl-1,3-dioxolane.

Polar protic and polar aprotic solvents can be used as the solvent in the methods described herein. In certain embodiments, the solvent is selected from water, alcohols, ethers, ketones, esters, and combinations thereof. Exemplary solvents include, but are not limited to water, methanol, ethanol, 1-propanol, 2-propanol, glycerol, glycol, ethylene glycol dimethyl ether, diglyme, polyethylene glycol, polyethylene glycol dimethyl ether, diethyl ether, dimethoxyethane, tetrahydrofuran, tetrahydropyran, dioxane, tert-butyl methylether, and combinations thereof. In certain embodiments, the solvent comprises methanol and tetrahydrofuran.

The oxidation agent can be any compound that is capable of oxidizing the hydroborated intermediate to an alcohol. In certain embodiments, the oxidation agent is selected from the group consisting of $H_2O_2$, tBuOOH, and $NaBO_3$.

Depending on the structure of the compound of Formula 5, the chiral bisphosphine ligand and the desired ee/yield, the optimal temperature for conducting the method described herein can be any reaction temperature above −60° C. In certain embodiments, the reaction temperature is between −40° C. and 60° C., −40° C. and 50° C., −30° C. and 50° C., −30° C. and 40° C., −30° C. and 30° C., −30° C. and 20° C., −30° C. and 10° C., −30° C. and 0° C., −20° C. and 0° C., or −10° C. and 0° C. In certain embodiments, the reaction temperature is 22° C. or below.

The experimental results in Table 2 (FIG. 11) demonstrate the broad range of structurally diverse substitutes that are tolerated on the compound of Formula 5 and afford the compound of Formula 4 in excellent yield, enantiomeric excess, and diastereomeric excess. Depending on the enantiomer of chiral bisphosphine ligand in the copper complex, either the (R) or the (S) enantiomer of the compound of Formula 4 can be selectively obtained. The compound of Formula 4 can be prepared with an enantiomeric excess (ee) of between 10% to 99.9%. In certain embodiments, the ee of the compound of Formula 4 is 90-99.9%, 91-99.9%, 92-99.9%, 93-99.9%, 94-99.9%, 94-99.9%, 95-99.9%, 96-99.9%, 97-99.9%, 98-99.9%, 99-99.9%, 99-99.7%, or 99-99.5%. In certain embodiments, the ee of the compound of Formula 4 is greater than 40%, greater than 50%, greater than 60%, greater than 70%, greater than 80%, greater than 90%, greater than 95%, greater than 97%, greater than 99%, or greater than 99.5%. In certain embodiments, the diastereomeric excess (de) of the compound of Formula 4 is 90-99.9%, 91-99.9%, 92-99.9%, 93-99.9%, 94-99.9%, 94-99.9%, 95-99.9%, 96-99.9%, 97-99.9%, 98-99.9%, 99-99.9%, 99-99.7%, 99-99.5%, 95-99.5%, 95-99%, 95-98%, 95-97%, or 95-96%. In certain embodiments, the de of the compound of Formula 4 is greater than 40%, greater than 50%, greater than 60%, greater than 70%, greater than 80%, greater than 90%, greater than 95%, greater than 97%, greater than 99%, or greater than 99.5%.

The methods described herein can yield the compound of Formula 4 in yields of 40-50%, 41-50%, 42-50%, 43-50%, 44-50%, 45-50%, 46-50%, 47-50%, 48-50%, 49-50%, 40-49%, 41-49%, 42-49%, 43-49%, 44-49%, 45-49%, 46-49%, 47-49%, 48-49%, or 49-49%.

In certain embodiments, the method further comprises the step of isolating a compound of Formula 7:

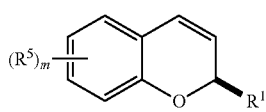

7 wherein the compound of Formula 7 is enantiomerically enriched. The ee of the compound of Formula 7 can be between 10% to 99.9%. In certain embodiments, the ee of the compound of Formula 7 is 90-99.9%, 91-99.9%, 92-99.9%, 93-99.9%, 94-99.9%, 94-99.9%, 95-99.9%, 96-99.9%, 97-99.9%, 98-99.9%, 99-99.9%, 99-99.7%, or 99-99.5%. In certain embodiments, the ee of the compound of Formula 7 is greater than 40%, greater than 50%, greater than 60%, greater than 70%, greater than 80%, greater than 90%, greater than 95%, greater than 97%, greater than 99%, or greater than 99.5%.

The compound of Formula 7 can be isolated in a yield between 40-50%, 41-50%, 42-50%, 43-50%, 44-50%, 45-50%, 46-50%, 47-50%, 48-50%, 49-50%, 40-49%, 41-49%, 42-49%, 43-49%, 44-49%, 45-49%, 46-49%, 47-49%, 48-49%, or 49-49%.

In certain embodiments, further synthetic modification to the chemical structure of the compound of Formula 4 may be necessary to prepare compounds of Formula 1. Exemplary synthetic modifications include, oxidation, reduction, halogenation, nitration, alkylation, acylation, phosphorylation, sulfonylation, carbon-carbon bond formation (e.g., using metal catalyzed reactions), electrophilic aromatic substitution, nucleophilic aromatic substitution, condensation reactions, nucleophilic substitution, protecting group attachment/removal, and the like. Such synthetic modifications are well within the skill of persons of ordinary skill in the art.

The present disclosure also provides a method of treating an inflammatory disease in a subject in need thereof, the method comprising: administering a therapeutically effective amount of a compound described herein to the subject. The inflammatory disease can be asthma, autoimmune diseases, chronic inflammation, chronic prostatitis, glomerulonephritis, hypersensitivities, inflammatory bowel disease, pelvic inflammatory disease, reperfusion injury, rheumatoid arthritis, transplant rejection, vasculitis, and the like. In certain embodiments, the compound inhibits the rate of secretion in the subject of at least one pro-inflammatory cytokine selected from the group consisting of IL-1β, IL-6 and TNF-α.

TNF-α inhibitors are known to be useful in the treatment of a variety of allergic, traumatic and other injurious disorders including, but not limited to asthma, chronic bronchitis, atopic dermatitis, urticaria, allergic rhinitis, allergic conjunctivitis, eosiniophilic granuloma, rheumatoid arthritis, septic shock, ulcerative colitis, Crohn's disease, reperfusion injury of the myocardium and brain, chronic glomerulonephritis, and adult respiratory distress syndrome.

Inhibition of IL-1β is known to be useful in the treatment of numerous inflammatory diseases including, but not limited to, meningitis, septic shock, adult respiratory distress syndrome, arthritis, cholangitis, colitis, encephalitis, endocarditis, glomerulonephritis, hepatitis, myocarditis, pancreatitis, pericarditis, reperfusion injury, vasculitis, fibrosis, and cirrhosis.

IL-6 inhibitors are known to be useful in the treatment of numerous inflammatory diseases including, but not limited to, psoriasis, Alzheimer's disease, rheumatoid arthritis, systemic onset juvenile idiopathic arthritis, hypergammaglobulinemia, Crohn's disease, ulcerative colitis, systemic lupus erythematosus, multiple sclerosis, Castleman's disease, cardiac myxoma, asthma, allergic asthma, autoimmune insulin-dependent diabetes mellitus, chronic obstructive pulmonary disease, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy, and the like.

The compounds described herein are also useful in the treatment of autoimmune diseases. Accordingly, also provided herein is a method of treating an autoimmune disorder in a subject in need thereof, the method comprising: administering a therapeutically effective amount of a compound described herein to the subject. In certain embodiments, the autoimmune disorder is Type 1 diabetes, psoriasis, multiple sclerosis, systemic lupus erythematosus, inflammatory bowel disease, Addison's disease, Graves' disease, Sjögren's syndrome, autoimmune vasculitis, or celiac disease.

Provided herein is a method of treating an inflammatory disease in a subject in need thereof, the method comprising: administering a therapeutically effective amount of a compound to the subject, wherein the compound has Formula 3:

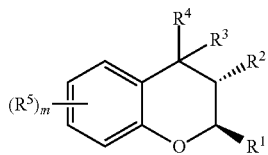

3 or a pharmaceutically acceptable salt thereof, wherein
m is a whole number selected from 1-3;
q is a whole number selected from 2-6;
$R^1$ is alkyl, aryl, or heteraryl;
$R^2$ is —OR, —O(C=O)$R^7$, —O(C=O)O$R^7$, —O(C=O)N($R^7$)$_2$, or —O(P=O)(OH)$_2$; each of $R^3$ and $R^4$ is independently hydrogen, alkyl, aryl, heteroaryl, —OR, or —O(C=O)$R^7$; or
$R^3$ and $R^4$ taken together with the carbon to which they are covalently bonded form (C=O);
$R^5$ for each instance is independently selected from the group consisting of hydrogen, halide, nitrile, nitro, —OR, —SR, —NR$_2$, —(C=O)R, —(C=O)OR, —(C=O)NR$_2$, —N(R)(C=O)R, —O(C=O)R, —N(R)(C=O)OR, —O(C=O)NR$_2$, —SO$_2$R, —SO$_2$NR$_2$, haloalkyl, perhaloalkyl, alkyl, cycloalkyl, alkenyl, alkynyl, aryl, heterocycloalkyl, heteroaryl, —OCH$_2$OMe, and —(CR$_2$)$_q$R$^8$; or two instances of $R^5$ taken together form a 5-6 membered cycloalkyl, heterocycloalkyl, aryl, or heteroaryl;
$R^7$ for each instance is independently selected from the group consisting of hydrogen, alkyl, cycloalkyl, alkenyl, alkynyl, aryl, heterocycloalkyl, heteroaryl, and —(CR$_2$)$_q$R$^8$; or two instances of $R^7$ taken together form a 5-6 membered cycloalkyl, heterocycloalkyl, or heteroaryl;
$R^8$ for each instance is independently selected from the group consisting of —OR, —SR, —NR$_2$, —(C=O)R, —(C=O)OR, —(C=O)NR$_2$, —N(R)(C=O)R, —O(C=O)R, —N(R)(C=O)OR, —O(C=O)NR$_2$, —SO$_2$R, and —SO$_2$NR$_2$; and R for each instance is independently selected from the group consisting of hydrogen, alkyl, cycloalkyl, alkenyl, alkynyl, aryl, heterocycloalkyl, and heteroaryl; or two instances of R taken together form a 5-6 membered heterocycloalkyl or heteroaryl.

In certain embodiments of the method of treatment, $R^1$ is:

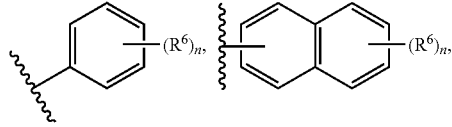

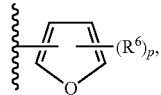

or propyl;
n is a whole number selected from 1-3;
p is a whole number selected from 1-2; and
$R^6$ for each instance is independently selected from the group consisting of hydrogen, halide, nitrile, nitro, —OR, —SR, —NR$_2$, —(C=O)R, —(C=O)OR, —(C=O)NR$_2$, —N(R)(C=O)R, —O(C=O)R, —N(R)(C=O)OR, —O(C=O)NR$_2$, —SO$_2$R, —SO$_2$NR$_2$, haloalkyl, perhaloalkyl, alkyl, cycloalkyl, alkenyl, alkynyl, aryl, heterocycloalkyl, heteroaryl, —OCH$_2$OMe, and —(CR$_2$)$_q$R$^8$.

In certain embodiments of the method of treatment, the compound has Formula 3; m is 1 or 2 and $R^3$ and $R^4$ are each hydrogen.

In certain embodiments of the method of treatment, and $R^2$ is —OH, —O(C=O)$R^7$, or —O(P=O)(OH)$_2$.

In certain embodiments of the method of treatment, the compound has Formula 3; each of n and p is 1; and $R^6$ is hydrogen.

In certain embodiments of the method of treatment, the compound has Formula 3; and $R^5$ for each instance is independently selected from the group consisting of halide and —OH.

In certain embodiments of the method of treatment, the compound has Formula 2:

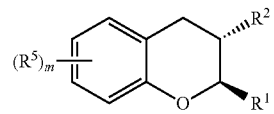

2 or a pharmaceutically acceptable salt thereof, wherein m is a whole number selected from 1-2;
q is a whole number selected from 2-6;
$R^1$ is

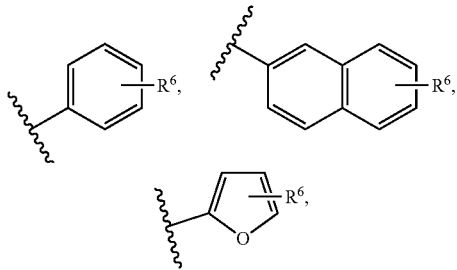

or propyl;
$R^2$ is —OR, —O(C=O)$R^7$, —O(C=O)O$R^7$, —O(C=O)N($R^7$)$_2$, or —O(P=O)(OH)$_2$;
$R^5$ for each instance is independently selected from the group consisting of hydrogen, halide, nitrile, nitro, —OR, —NR$_2$, haloalkyl, perhaloalkyl, alkyl, cycloalkyl, aryl, heterocycloalkyl, heteroaryl, —OCH$_2$OMe, and —(CR$_2$)$_q$R$^8$;
$R^6$ for each instance is independently selected from the group consisting of hydrogen, halide, nitrile, nitro, —OR, —NR$_2$, haloalkyl, perhaloalkyl, alkyl, cycloalkyl, aryl, heterocycloalkyl, heteroaryl, —OCH$_2$OMe, and —(CR$_2$)$_q$R$^8$;

R[7] for each instance is independently selected from the group consisting of hydrogen, alkyl, cycloalkyl, alkenyl, alkynyl, aryl, heterocycloalkyl, heteroaryl, and —(CR$_2$)$_q$R[8]; or two instances of R[7] taken together form a 5-6 membered cycloalkyl, heterocycloalkyl, or heteroaryl;

R[8] for each instance is independently selected from the group consisting of —OR, —SR, —NR$_2$, —(C=O)R, —(C=O)OR, —(C=O)NR$_2$, —N(R)(C=O)R, —O(C=O)R, —N(R)(C=O)OR, —O(C=O)NR$_2$, —SO$_2$R, and —SO$_2$NR$_2$; and R for each instance is independently selected from the group consisting of hydrogen, alkyl, cycloalkyl, alkenyl, alkynyl, aryl, heterocycloalkyl, and heteroaryl; or two instances of R taken together form a 5-6 membered heterocycloalkyl or heteroaryl.

In certain embodiments of the method of treatment, the compound has Formula 2; R[2] is —OH; and R[6] is hydrogen, halide, trifluoromethyl, —OCH$_2$OMe, or —OCH$_2$Ph.

In certain embodiments of the method of treatment, the compound has Formula 2; R[5] for each instance is independently selected from the group consisting of hydrogen, methyl, —OCH$_2$OMe, halide, —OH, and —OMe.

In certain embodiments of the method of treatment, the compound has Formula 2; R[5] for each instance is independently selected from the group consisting of hydrogen; and chloride and R[2] is —OH.

In certain embodiments of the method of treatment, the compound has Formula 2; R[5] for each instance is independently selected from the group consisting of hydrogen; chloride and R[2] is —OH; and R[6] is hydrogen.

In certain embodiments of the method of treatment, the compound is selected from the group consisting of:

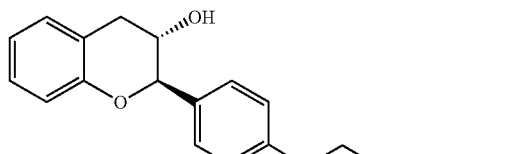

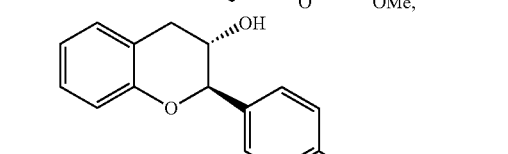

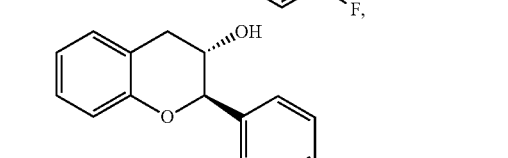

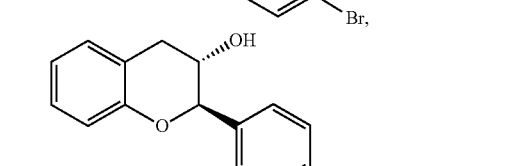

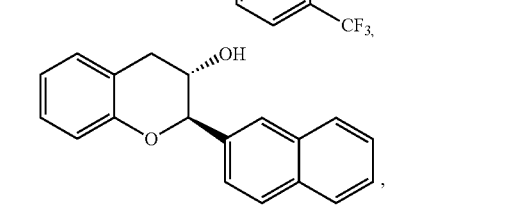

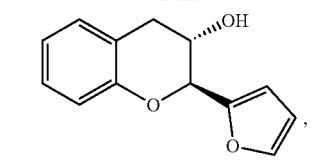

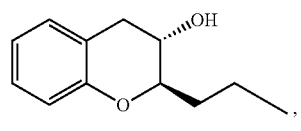

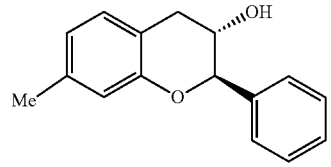

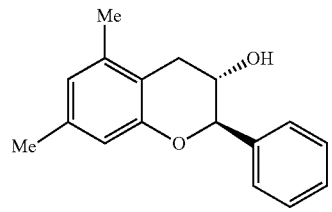

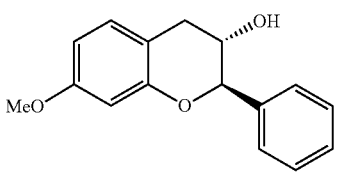

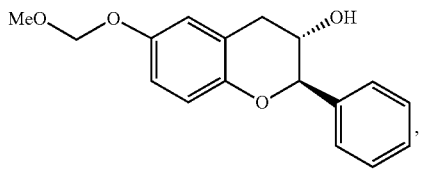

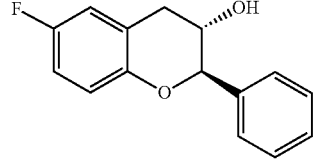

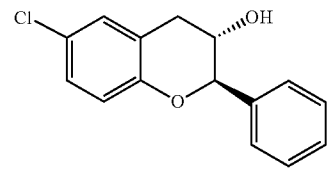

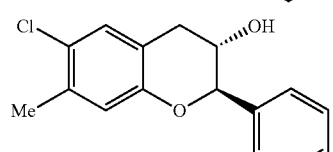

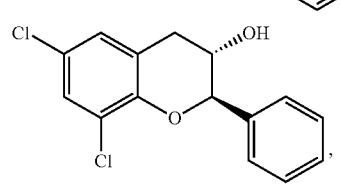, and

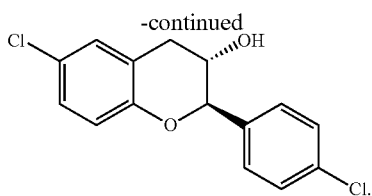

In certain embodiments of the method of treatment, the compound is selected from the group consisting of:

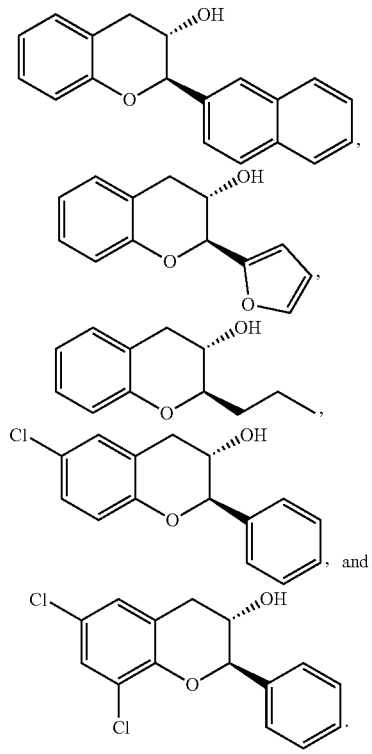

In certain embodiments of the method of treatment, the compound is:

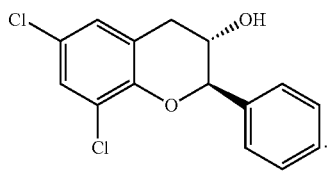 [SMILES: O[C@H]1Cc2cc(Cl)cc(Cl)c2O[C@@H]1c1ccccc1]

In certain embodiments of the method of treatment, the compound inhibits the rate of secretion of at least one pro-inflammatory cytokine selected from the group consisting of IL-1β, IL-6 and TNF-α.

The present disclosure is not to be limited in scope by any of the specific embodiments described herein. The following embodiments are presented for exemplification only.

EXAMPLES

Cell culture The RAW 264.7 cell line was purchased from the Cell Bank of Shanghai Institute of Biochemistry & Cell Biology at the Chinese Academy of Sciences (Shanghai, China) and cultured in DMEM supplemented with 10% (v/v) fetal bovine serum (FBS), 100 U/ml penicillin and 100 U/ml streptomycin, in a stable environment with 5% $CO_2$ at 37° C. Before used in the following in vitro experiments, RAW 264.7 cells were pretreated with synthesized flavan-3-ol (25, 50 μM) for 24 h followed by LPS (1 μg/mL) stimulation for another 2 h.

Cell Viability Assay The CCK8 assay was used to evaluate the effect of each flavan-3-ol on the viability of RAW264.7 cells. Cells were plated into 96-well plates at a density of $2\times10^5$ cells/well in medium and cultured overnight. For formal experiments, cells were treated with different concentrations of flavan-3-ols (25, 50, and 100 μM). After 24 h, 20 μl CCK8 solution (cat #A311-01/02, Vazyme Biotech Co., Ltd., Nanjing, China) was added into the medium and incubated for 45 min. The absorbance was measured at 450 nm.

Enzyme-Linked Immunosorbent Assay (ELISA) RAW 264.7 cells were treated with these synthesized flavan-3-ols (25, 50 μM) for 24 h followed by LPS (1 μg/mL) stimulation for another 2 h and the culture supernatant was collected. The concentrations of IL-1β, IL-6 and TNF-α in the culture supernatant of RAW 264.7 cells were determined according to the manufacturer's instructions of the Duo-set enzyme linked immune sorbent assay kits, purchased from R&D Systems Co. Ltd. (Minneapolis, MN, USA).

RNA-sequencing analysis RAW 264.7 cells were treated with each flavan-3-ol (25, 50 μM) for 24 h followed by LPS (1 μg/mL) stimulation for another 2 h. Cells were collected and then directly prepared for cDNAs amplification and RNA-Seq library construction. Total RNA was isolated with TRIzol reagent from each group. A complementary DNA library was prepared and sequencing was performed according to the Illumina standard protocol developed by Suzhou GENEWIZ Biological Technology Co., Ltd. (https://www-.genewiz.com). Raw reads from RNAseq libraries were trimmed to remove the adaptor sequence and the reads with adaptor contaminants, low-quality reads (the mass value Q-score <5 of the base number accounts for more than 50%), and reads from N (N indicates that the base information that cannot be determined) which is >10%. After filtering, reference genome and gene model annotation files were downloaded from a genome website browser (NCBI/UCSC/Ensembl). Indexes of the reference genome were built using Bowtie v2.0.6 and paired-end clean reads were aligned to the reference genome using TopHat v2.0.9. Bowtie was used for a BWT (Burrows-Wheeler Transformer) algorithm for mapping reads to the genome and Tophat can generate a database of splice junctions based on the gene model annotation file and thus achieve a better mapping result than other non-splice mapping tools. For the quantification of gene expression level, HTSeq V0.6.1 was used to count the read numbers mapped for each gene. The RPKM of each gene was calculated based on the gene read counts mapped to this gene. A differential expression analysis was performed using the DESeq R package (1.10.1). For clustering, the inventors clustered different samples to see the correlation using hierarchical clustering distance method with the function of heatmap, SOM (Self-organization mapping) and k means using silhouette coefficient to adapt the optimal classification with default parameter in R. The complete RNA-seq datasets in this manuscript captioned has been deposited at GEO database (http://www.ncbi.nlm.nih.gov/geo/) under accession ID GSE181052.

Gene ontology (GO) and KEGG enrichment analysis GO enrichment analysis of differentially expressed genes was implemented by the GOseq R Package, in which gene length bias was corrected. GO analysis was performed with the DAVID online tool (https://david.ncifcrf.gov/). Top GO categories were selected according to the P-values. Pathways of differentially expressed genes were analyzed by the KEGG database (http://www.kegg.jp/kegg/). The inventors used KOBAS software to test the statistical enrichment of differential expression genes in KEGG pathways.

Statistical Analysis The data shown in the study were obtained from at least three independent experiments, and all data in different experimental groups were expressed as the mean standard deviation (SD). Statistical analyses were performed using a one-way ANOVA, with post hoc analysis. Details of each statistical analysis are provided in the figure legends. Differences with P values <0.05 were considered statistically significant.

Figure 10:
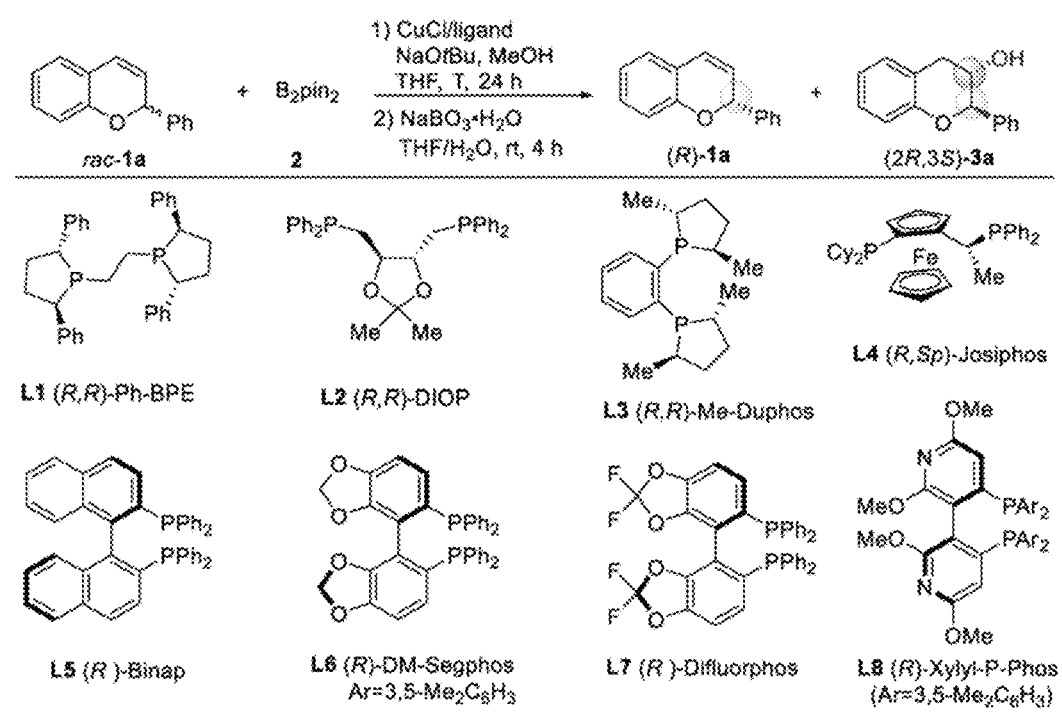
FIG. 10 shows Table 1 that tabulates the results of reaction condition optimization for Cu-catalyzed asymmetric hydroboration of flavene. [a] Reaction conditions: CuCl (5.0 mol %), ligand (5.5 mol %), 1a (0.2 mmol), 2 (0.24 mmol), NaOtBu (10.0 mol %), MeOH (0.2 mmol), THF (0.6 mL); NaBO$_3$—H$_2$O (0.5 mmol), H$_2$O (0.6 mL). [b]Isolated yield. [c]Determined by chiral HPLC. [d]Diastereomeric ratio (dr)>19:1 (determined by $^1$H NMR). [e]Calculated conversion, C=ee$_{1a}$/(ee$_{1a}$+ee$_{3a}$). [f]Selectivity factor (s)=ln[(1-C)(1-ee$_{1a}$)]/ln[(1-C)(1+ee$_{1a}$)].
Figure 11:
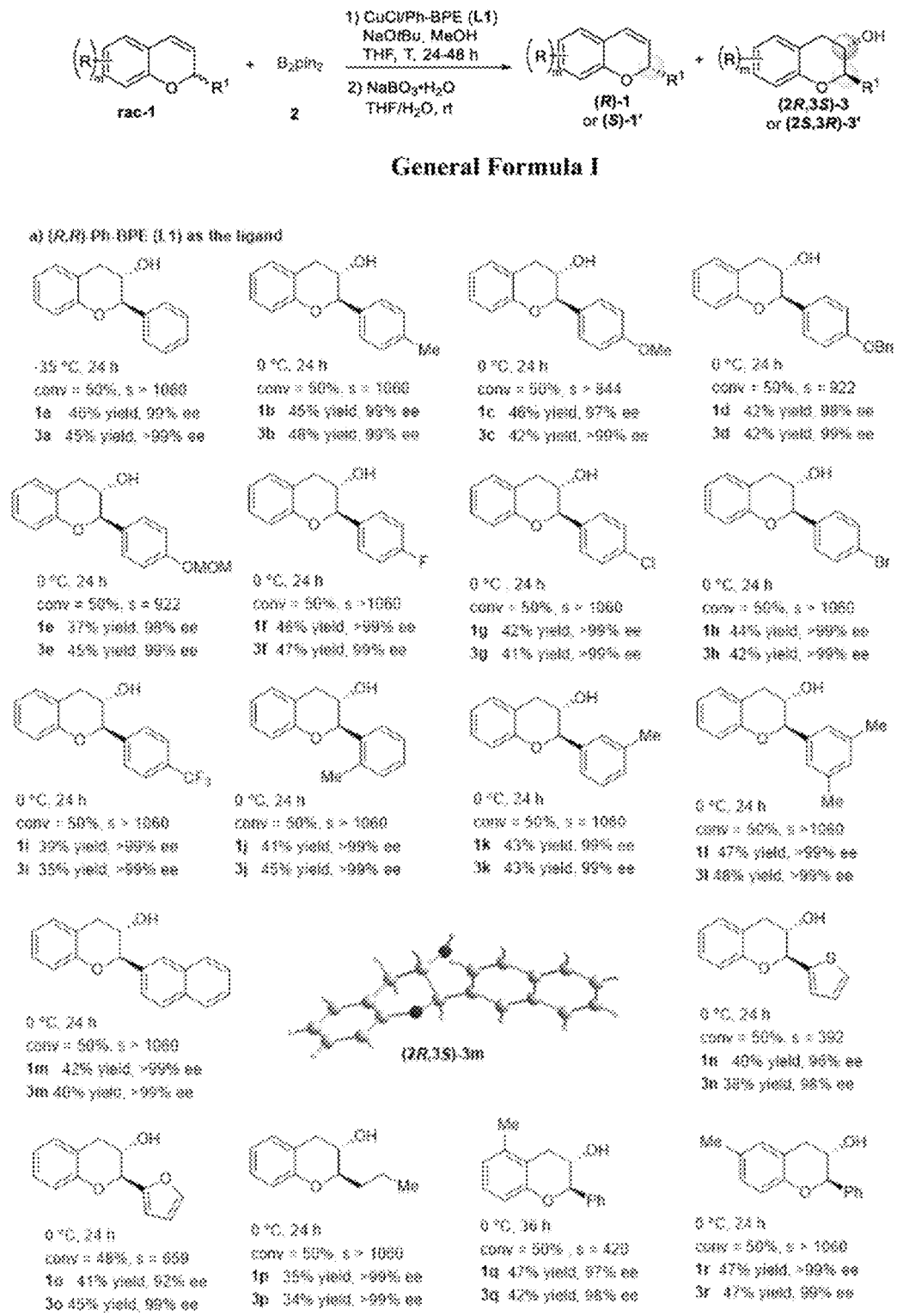
FIG. 11 shows Table 2 that tabulates the results of different chromene substrates in the methods described herein. [a] Reaction conditions: CuCl (5.0 mol %), Ph-BPE (L1) (5.5 mol %), 1 (0.2 mmol), 2 (0.24 mmol), NaOtBu (10 mol %), MeOH (0.2 mmol), THF (0.6 mL). Yields were isolated yields. Ees were determined by chiral HPLC. Diastereomeric ratio (dr)>19:1 (determined by $^1$H NMR). Calculated conversion, C=ee$_1$/(ee$_1$+ee$_3$). Selectivity factor (s)=ln[(1-C) (1-ee$_1$)]/ln[(1-C) (1+ee$_1$)].

Reaction condition optimization In Table 1 (FIG. 10), the asymmetric hydroboration/kinetic resolution of rac-flavene (2-aryl-chromene) 1a with $B_2Pin_2$ (2) in MeOH was evaluated in the presence of Cu complex, followed by oxidative workup with $NaBO_3 \cdot H_2O$. Initially, various chiral bisphosphine ligands with different backbones utilizing CuCl as the catalyst precursor were investigated. The flavan-3-ol 3a with vicinal chiral centers was obtained essentially as a single diastereomer (dr>19:1) in 50% isolated yield with 73% ee, and the recovered 1a was also obtained in 32% yield with 99% ee (s=32), catalyzed by the in-situ complex formed from 5.0 mol % CuCl and 5.5 mol % (R,R)-Ph-BPE L1 in THF at room temperature (FIG. 10, Table 1, entry 1). (R,R)-Me-Duphos L3 and (R,Sp)-Josiphos L4 could promote the full conversion of rac-flavene 1a, but the ee values of product 3a were inferior (FIG. 10, Table 1, entry 3 and 4). When (R)-Binap L5 was employed, trace amount of product was detected (FIG. 10, Table 1, entry 5). Other diphosphine ligands, such as (R)-DM-Segphos L6, (R)-Difluorphos L7 and (R)-Xylyl-P-Phos L8 afforded product 3a with high enantioselectivities (74-86%), albeit with low enantioselectivities for the recovered substrate 1a (20-68%). The effect of temperature was also investigated by using (R,R)-Ph-BPE L1 as the ligand. The kinetic resolution was highly selective when the reaction temperature was lowered to −35° C. Both the flavanol product 3a and the substrate flavene 1a were obtained in excellent yields (45% and 46%) and extremely high enantioselectivities (99%), with a selective factor of 1060 (FIG. 10, Table 1, entry 11). Substrate scope With the optimized reaction conditions in hand, the inventors next examined the scope of flavenes with various substituents, and the results were illustrated in Table 2 (FIG. 11). A very broad scope of substrates was studied, with substituents on both the C2-phenyl ring and the benzopyran moieties spanning a diverse range of sterically and electronically different groups. Generally, the reactions afforded the flavan-3-ols 3a-3ai as single diastereomers in high yields (34-48%) with excellent enantioselectivities (95→99%, >99% for most substrates), and the recovered (R)-flavenes in 35-48% yields with 83→99% enantioselectivities (s factor 170→1060). Substrates 1b-i bearing a wide range of electronically varied phenyls at the C2 position with different substituents proceeded with excellent chiral recognition. No significant steric effect was observed. The o-tolyl substituted substrate rac-1j afforded the product 3j with the highest enantioselectivity (>99%) and a selective factor of 1060. Replacing the phenyl ring with 2-naphthyl moiety led to a similar result, producing the pi-extended 2-naphthyl group product 3m with >99% ee and recovered flavene 1m with >99% ee (s factor >1060). Notably, the substrates containing heterocycles, such as 2-furyl or 2-thienyl, also worked well under the catalytic conditions and afforded the products 3n-o with 98-99% ee and the recovered substrates 1n-o with 98-99% ee. To the inventors delight, the 2-alkyl-chromene 1p was successfully resolved under these reaction conditions, giving the product 3p in 34% yield and >99% ee, and recovered starting material in 35% yield with >99% ee (s factor >1060). The hydroboration of flavenes with an electron-donating group either at the C5, C6, C7 or C8 position (1q-1aa) were found successful, and furnished the desired products in high yields (39-46%) with excellent enantioselectivities (83→99%). Besides, substrate 1ac with a hydroxyl substituent at C6 position could also be successfully converted into the corresponding product in excellent enantioselectivity (>99% ee). The racemic flavenes bearing an electron-withdrawing group at C6 or C8 position (1ad-ag) were well-tolerated. High yields and excellent enantioselectivities were obtained for both products and recovered flavenes. Remarkably, the flavenes with —F or —Cl groups on both C2-phenyl ring and benzopyran also reacted smoothly, giving the products in high yields with excellent enantioselectivities (3ah and 3ai). The configuration of the recovered 1a were assigned as R configuration by comparison with the literature data of the known compound, and the absolute configuration of product 3m was confirmed as (2R,3S) by X-ray crystal structure analysis. Notably, the opposite configuration of flavanols (2S,3R)-3' can also be accessed by using the ligand (S, S)-Ph-BPE (L1) under similar conditions (Table 2, FIG. 11, 3m', 3o', 3p', 3ae', 3ag').

Substrate rac-1 including the compounds from 1a to 1ai; (R)-1 and (S)-1' including the compounds from (R)-1a to (R)-1ai and also their enantiomers (S)-1a' to (S)-1ai'; (2R, 3S)-3 and (2S,3R)-3' including the compounds from (2R, 3S)-3a to (2R,3S)-3ai, and also their enantiomers (2S,3R)-3a' to (2S,3R)-3ai'. m can be a whole number selected from 0-4; each instance of R can independently be alkyl, aryl, halide, alkoxy, —OCH₂OMe, or hydroxyl group; each instance of R can be positioned at C5, C6, C7 or C8 position of the benzofuran; and $R^1$ can be alkyl, aryl or heterocyclic group, wherein the aryl is optionally substituted with one or more substituents selected from the group consisting of alkyl, perhaloalkyl, halide, aralkyloxy, and alkoxy, —OCH₂OMe.

Anti-inflammatory efficacy of flavan-3-ols Natural products or small molecules containing flavan skeleton have been reported to exhibit broad anti-inflammatory activity. To evaluate the anti-inflammatory effects of these newly synthesized flavan-3-ols, RAW 264.7 cells (mouse monocyte/macrophage cell) were used as the in vitro model. First, CCK-8 (Cell Counting Kit-8) assay was performed to test the effects of these newly synthesized flavan-3-ols on cell viability (FIG. 9a-d). RAW 264.7 cells were treated with the newly synthesized flavan-3-ols ranging from 25 to 100 µM for 24 h. As shown in FIG. 4a-c, treatment with each compound at 25 and 50 µM for 24 h had no effect on the cell viability of RAW 264.7 cell. Nevertheless, reduced viability was observed with some of the flavan-3-ols at 100 µM, such as compounds 3i, 3n, 3ad and 3ai. Therefore, the final concentration of each compound used in the following experiments were no more than 100 µM, and compound concentrations at 25 and 50 µM were used in the further experiments.

The increased pro-inflammatory cytokines production in RAW 264.7 cells has been reported to play an influential role in the inflammation response. To evaluate the anti-inflammatory effects of these flavan-3-ols in vitro, ELISA kits were employed to investigate their effects on the LPS (lipopolysaccharide)-induced pro-inflammatory cytokines production of RAW 264.7 cells. After treating with the flavan-3-ols (25 and 50 μM) and stimulated by LPS, the levels of three main pro-inflammation cytokines including IL-1β (interleukin-1β), IL-6 (interleukin-6), and TNF-α (tumor necrosis factor-α) in culture supernatant from RAW 264.7 cells were measured by ELISA kits, and then the inhibition rates of the flavan-3-ols on the secretion of each pro-inflammatory cytokine were calculated by the formula shown as follows.

$$\text{Inhibition Rate (\%)} = \frac{(L - Lc)}{L} \times 100\%$$

In this formula, "L" refers to "the pro-inflammatory cytokine level in cell culture supernatant of LPS-induced group (L)" and "Lc" refers to "the pro-inflammatory cytokine level in cell culture supernatant of compound-treated group (Lc)". Using this calculation, the reduced levels of pro-inflammation cytokines in the compound treated group would give higher values, which reflect higher inhibition rates.

$$\text{Inhibition Rate (\%)} = \frac{(L - Lc)}{L} \times 100\%$$

As shown in FIG. 4a-c, compared with LPS-stimulated group, most of the flavan-3-ols have inhibition effects on the secretion of IL-1β, IL-6 and TNF-α. The 5 final flavan-3-ols (3m, 3o, 3p, 3ae and 3ag) were selected that consistently showed higher inhibition rates (at least 20 to 60%) across all 3 pro-inflammatory cytokines tested, and omitted those that showed lower inhibition rates (10 to 20%). All these results suggested that these five entities of flavan-3-ols would serve as the potential inflammation inhibitors.

FIG. 4a-c show the effect of flavan-3-ols on pro-inflammatory cytokine secretion in vitro. RAW 264.7 cells were pretreated with each compound (25, 50 μM) for 24 h followed by LPS (1 μg/mL) stimulation for another 2 h. The concentrations of IL-1β, IL-6, TNF-α in RAW 264.7 cell culture supernatants were measured by ELISA kits and the inhibition rate of compound on the secretion of each pro-inflammatory cytokine was calculated.

Figure 5A:
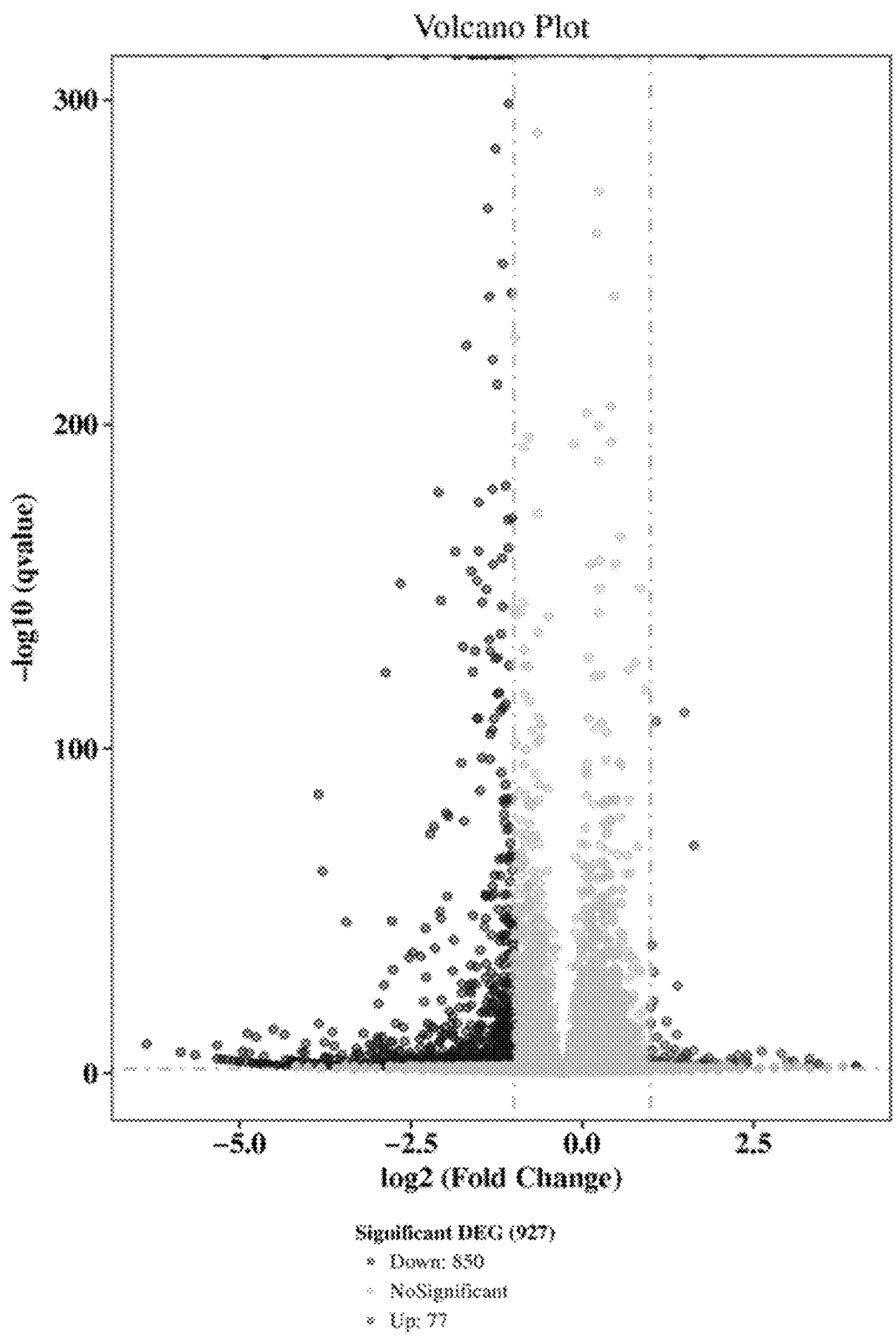
FIG. 5A shows RNA-seq analysis of flavan-3-ol 3ag-modulated genes. A volcano plot illustrating differentially regulated gene expression from RNA-seq analysis between LPS-stimulated group and compound 3ag-treated group. The upregulated and downregulated genes are shown in the orange and blue, respectively. Values are presented as the log 2 of tag counts.
Figure 5B:
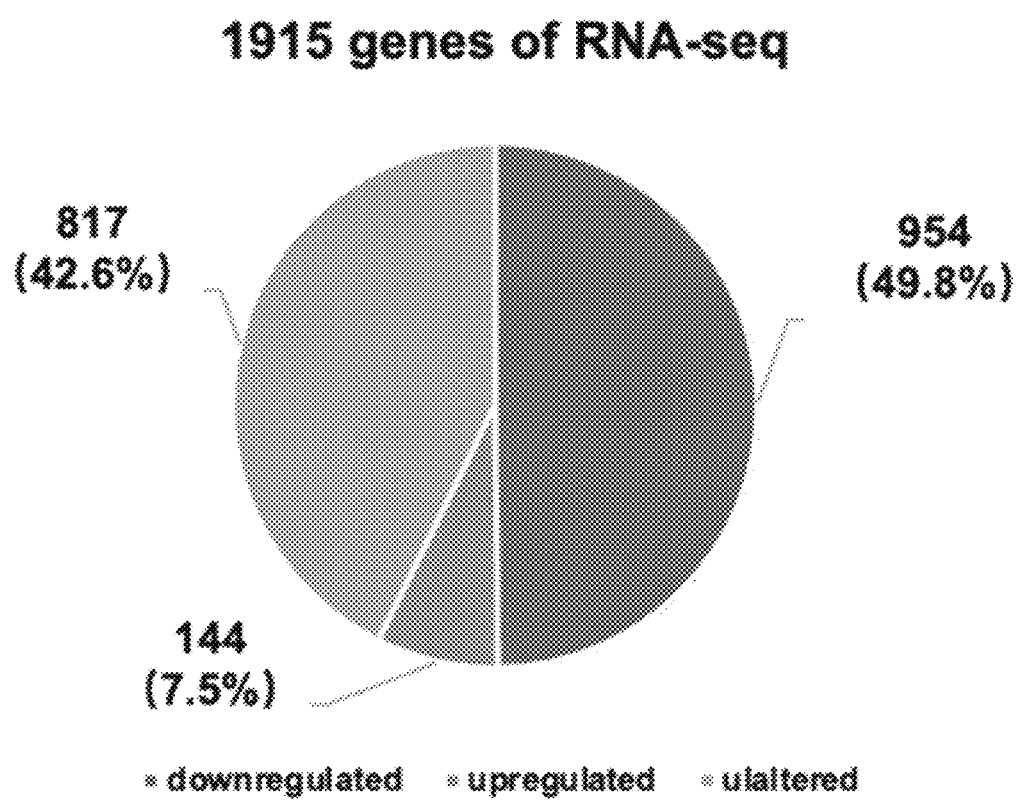
FIG. 5B shows RNA-seq analysis of flavan-3-ol 3ag-modulated genes. RNA-seq comparison revealed a total of 1915 genes expressed, of which 954 genes (49.8%) were downregulated and 144 genes (7.5%) were upregulated.

RNA-seq analysis of downstream genes regulated by flavan-3-ols. Given that compounds 3m, 3o, 3p, 3ae and 3ag exhibited potent anti-inflammatory effects, the inventors next examined flavan-3-ols-mediated transcriptional targets and pathways that could potentially be accounted for the inflammation response. RNA-seq analysis was performed to further study the effects of compounds 3m, 3o, 3p, 3ae and 3ag on gene transcriptional pathways related to inflammation. RAW 264.7 cells were used in the RNA-seq analysis, in which cells were pretreated with each compound (50 μM) for 24 h followed by LPS (1 μg/mL) stimulation for another 2 h. After analyzing the whole genome sequencing results, the inventors found that there were 1098 genes differentially regulated by compound 3ag as compared with the untreated LPS-stimulated group, (FIG. 5a), of which 954 genes (49.8%) were downregulated and 144 genes (7.5%) were upregulated (FIGS. 5a and 5b). Next, the inventors focused on genes related to inflammatory reactions and inflammation-related diseases (inflammation-related genes) based on the gene and pathway classification of Kyoto Encyclopedia of Genes and Genomes (KEGG database). Among all these inflammation-related genes, 75 genes were significantly changed by LPS stimulation as compared with the control group. In addition, as compared with the LPS-stimulated group, 40 genes were downregulated by 50 μM compound 3ag, and the other 4 compounds (3m, 3o, 3p, 3ae) also downregulated parts of inflammation-related genes at 50 μM. However, the other 4 compounds downregulated much fewer inflammation-related genes as compared to that of compound 3ag. Taken together, these results suggested that compound 3ag potentially exerts relatively stronger anti-inflammation effects by regulating a broader range of inflammatory genes and pathways.

Figure 6:
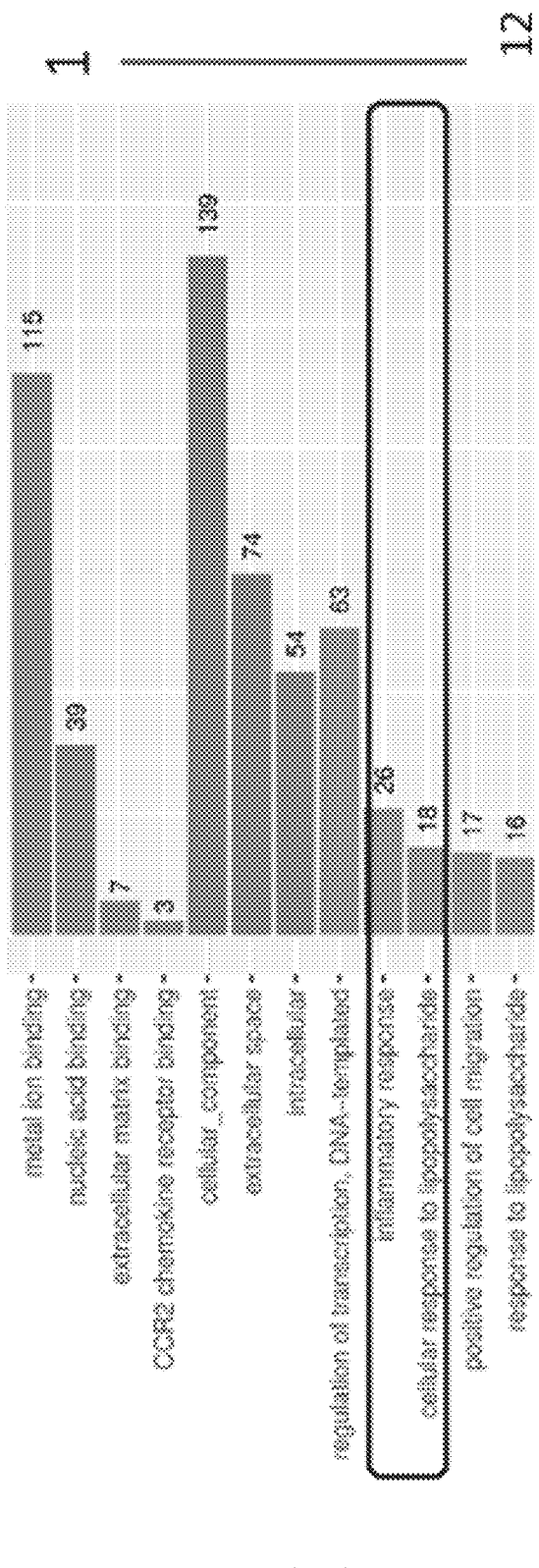
FIG. 6 shows gene ontology (GO) functional clustering of genes that were downregulated or upregulated in different biological processes. GO analysis result illustrates the genes that were significantly affected by compound 3ag treatment clustered in accordance with specific molecular functions (term 1-term 4), cellular components (term 5-term 7) and biological processes (term 8-term 30).
Figure 6:
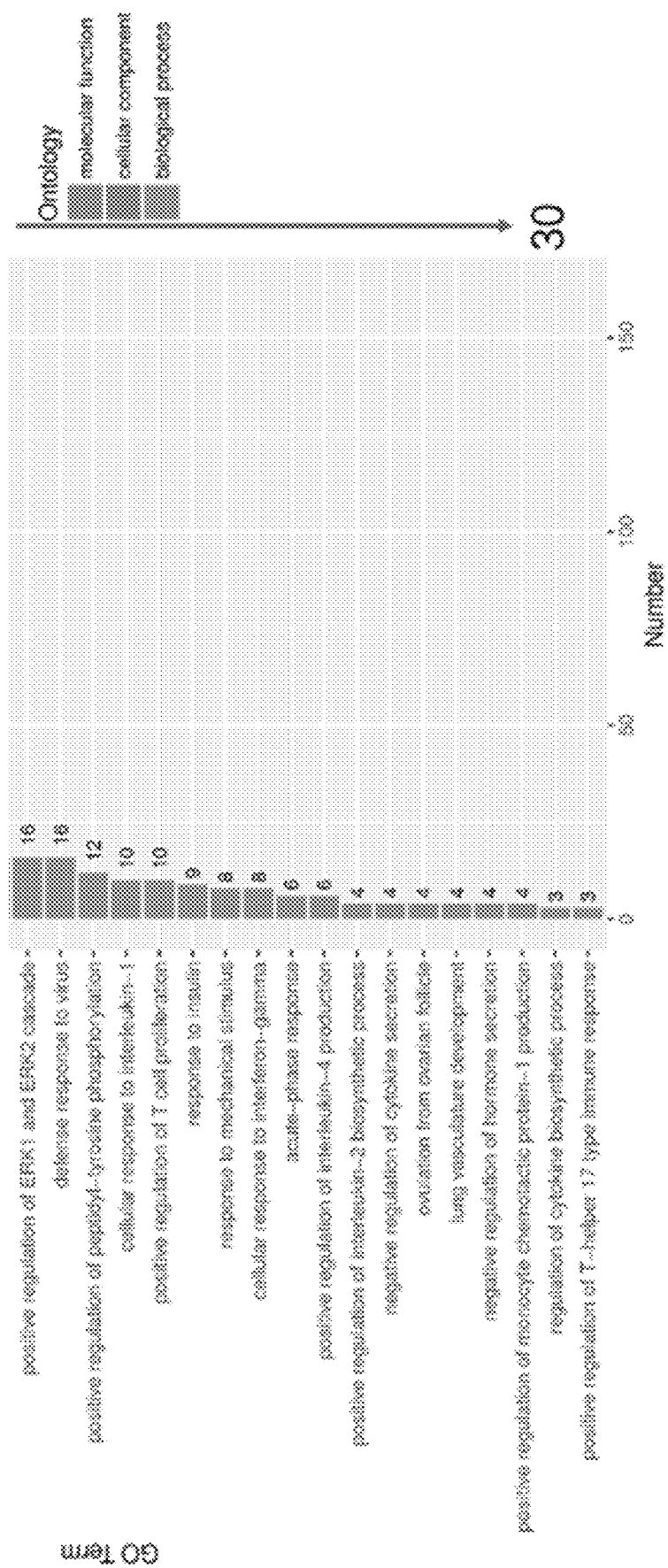

To further analyze the functional distribution of differentially-expressed genes in relation to different biological processes, cellular components and molecular functions, gene ontology (GO) enrichment analysis was performed. The histogram of GO enrichment of differentially-expressed genes was presented. As shown in FIG. 6, gene ontology (GO) enrichment analysis demonstrated different categories of genes that were significantly downregulated or upregulated by the treatment of compound 3ag as compared with the LPS-induced group. In line with the inventors ELISA results that showed reduction in pro-inflammatory cytokines (FIG. 4a-c), the downregulated genes were associated with inflammatory response (GO: 0006954) and cellular response to lipopolysaccharide (GO: 0071222) (FIG. 6). These results suggested that compound 3ag shows strong inhibition effects on inflammation process and is closely involved in inflammation response.

Figure 7A:
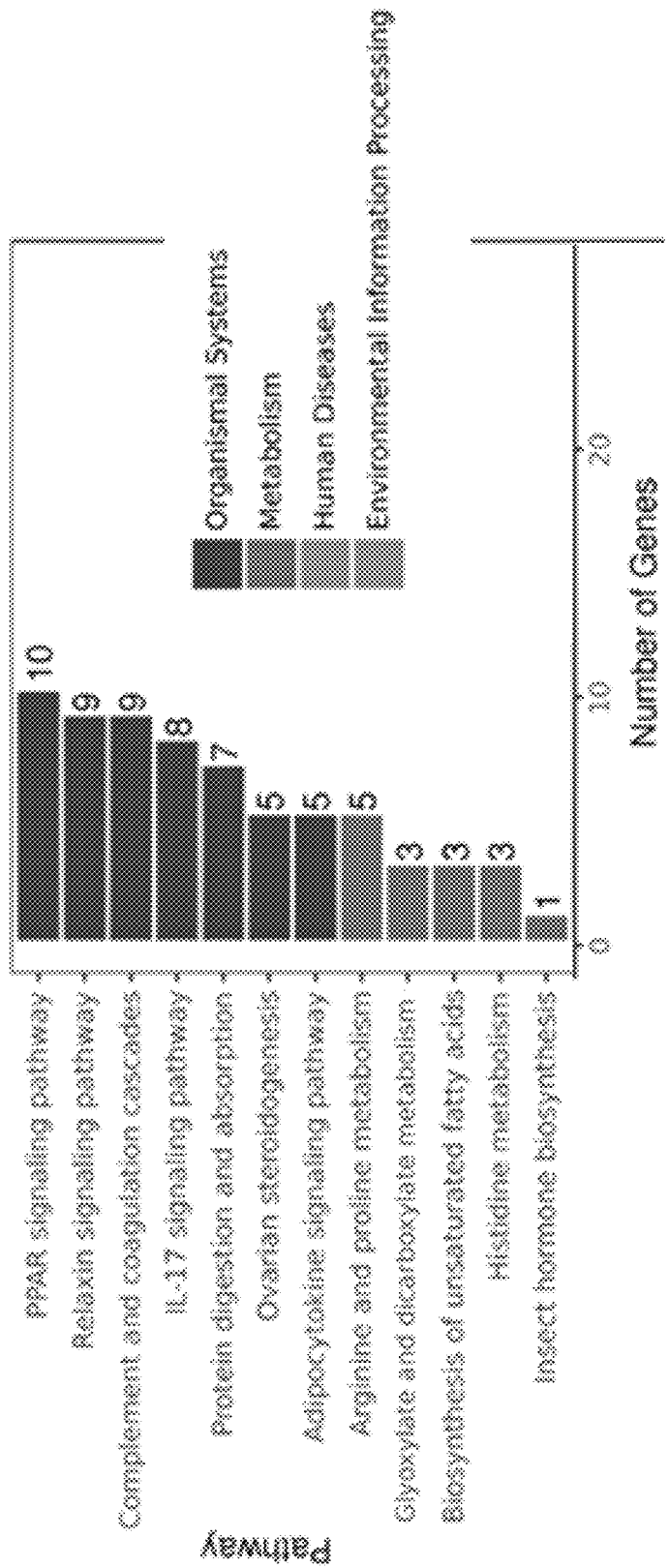
FIG. 7A shows the KEGG pathway analysis of the differentially-expressed genes. KEGG pathway analysis of the distribution of differentially-expressed genes. Compared with the LPS-induced group, the distribution of differentially-expressed genes regulated by compound 3ag distributed in different categories were shown.
Figure 7A:
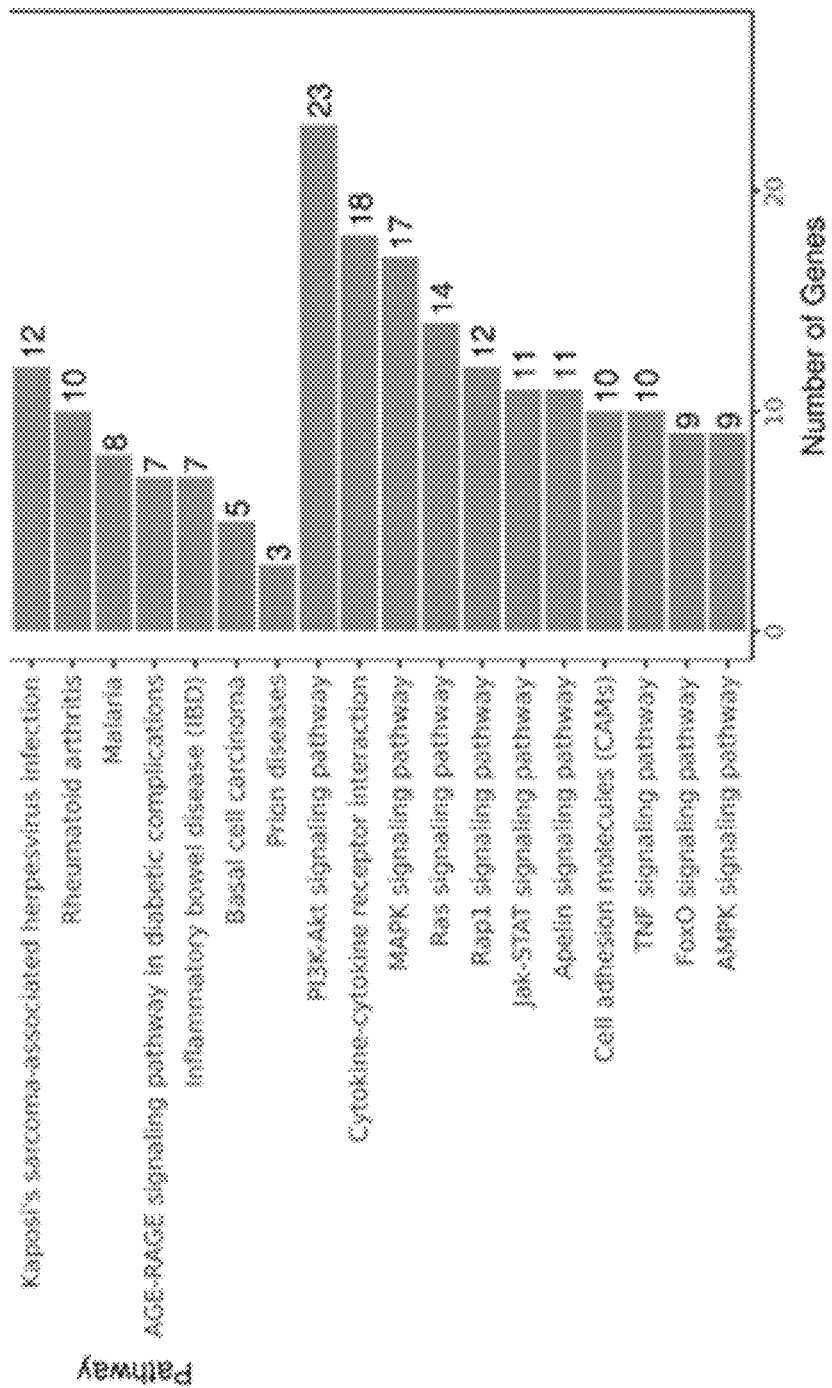
Figure 7B:
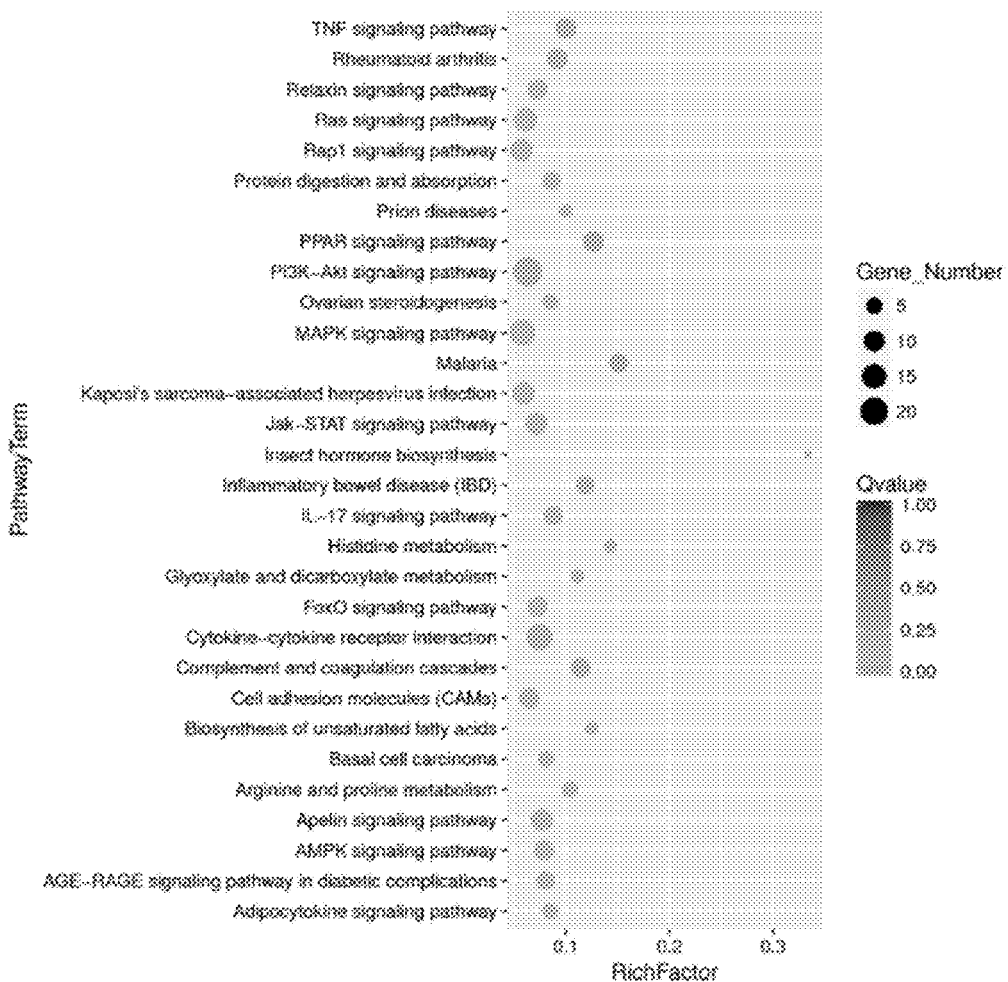
FIG. 7B shows the KEGG pathway analysis of the differentially-expressed genes. The Scatter plot showing KEGG rich distribution of differential genes.

Furthermore, to determine the biochemical metabolic pathways and signal transduction pathways involved in differentially expressed genes regulated by compound 3ag, KEGG pathway analysis was then performed. As shown in FIG. 7a-b, compared with the LPS-induced group, a number of genes that were downregulated in compound 3ag-treated group were distributed in several main pathways closely related to inflammation process including IL-17 signaling pathways, PI3K-Akt signaling pathway and TNF signaling pathway. More importantly, these genes downregulated by compound 3ag were closely related to several inflammatory diseases, such as rheumatoid arthritis and inflammatory bowel disease (IBD). Taken together, these results suggested that flavan-3-ol 3ag inhibited the transcription of genes closely involved in the process of inflammation and inflammation-related diseases, which is in line with the previous findings on the anti-inflammatory function of flavan skeleton compounds.

Figure 8:
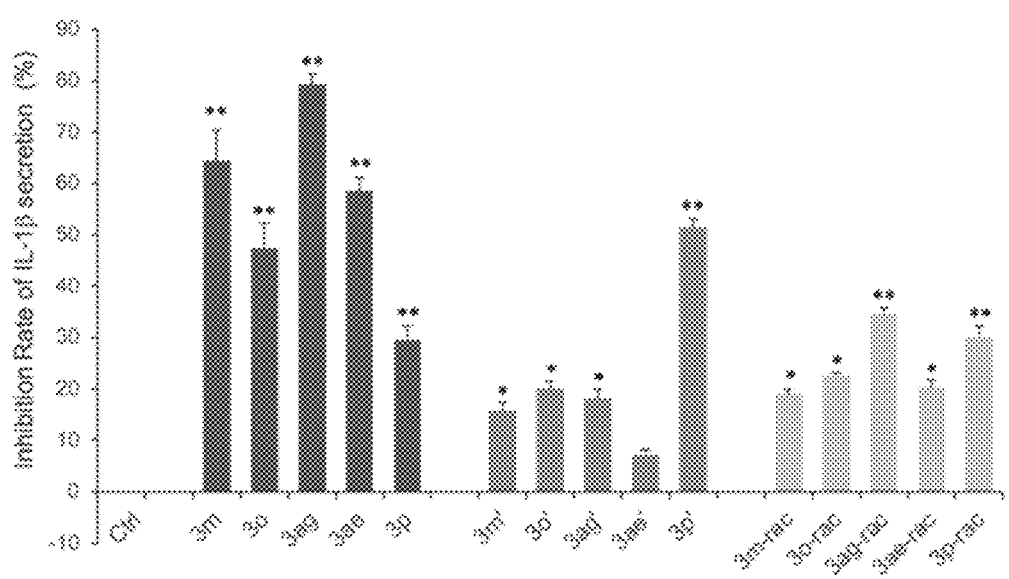
FIG. 8 shows the inhibition rates of compounds on IL-1β secretion. RAW 264.7 cells were pretreated with each compound (50 μM) for 24 h followed by LPS (1 μg/mL) stimulation for another 2 h. The concentrations of IL-1β in RAW 264.7 cell culture supernatants were measured by ELISA kits and the inhibition rate of compound on the secretion of each pro-inflammatory cytokine was calculated. Data from three independent experiments were expressed as means±SD. *P<0.05, **P<0.01 compared with LPS-stimulated group.
Figure 9A:
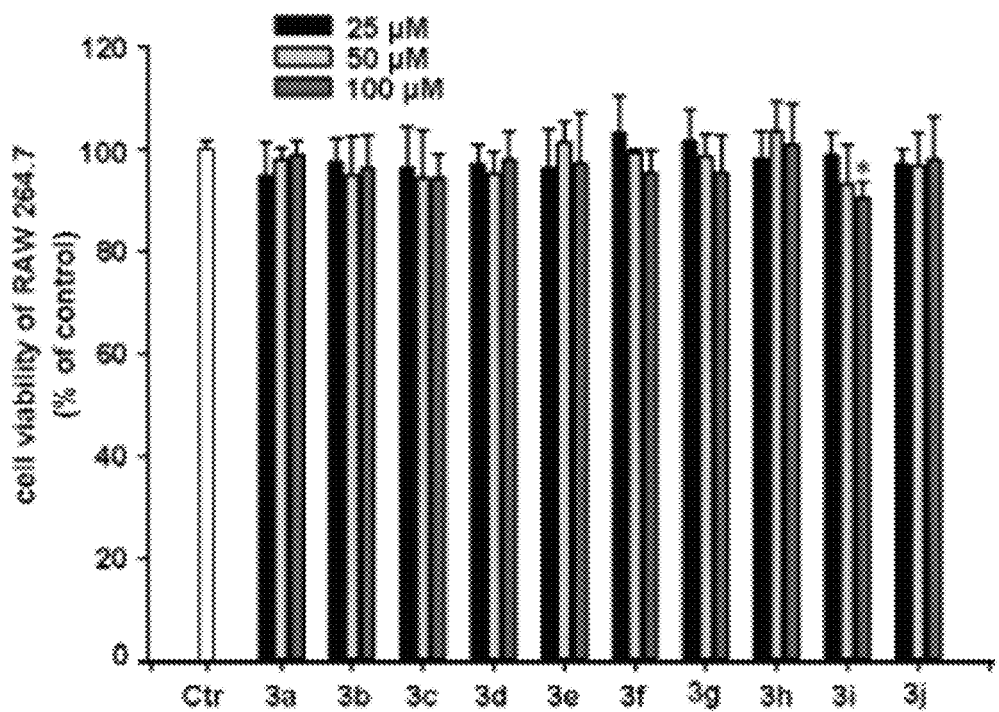
FIG. 9A shows the effect of compounds on the cell viability. RAW 264.7 cells were plated in a 96-well plate and treated with each compound (0, 25 μM, 50 μM and 100 μM) for 24 h. The viability of cells was tested by CCK8 assay. Data from three times independent experiments were expressed as means±SD. *P<0.05 compared with the control group for compound 3a-3j.
Figure 9B:
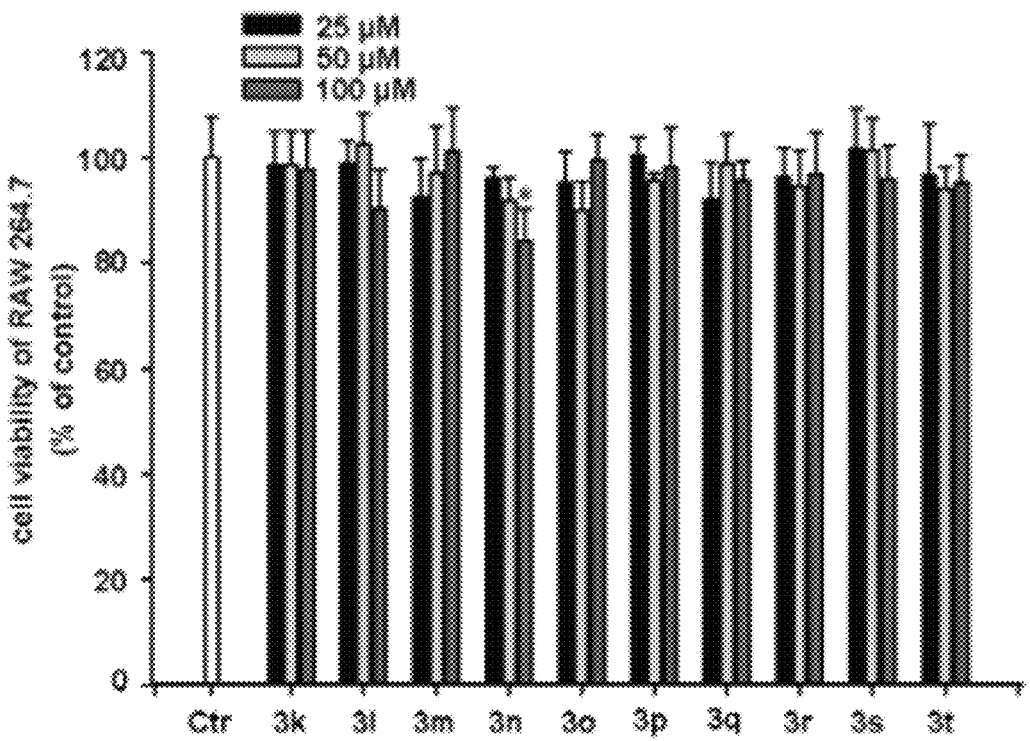
FIG. 9B shows the effect of compounds on the cell viability. RAW 264.7 cells were plated in a 96-well plate and treated with each compound (0, 25 μM, 50 μM and 100 μM) for 24 h. The viability of cells was tested by CCK8 assay. Data from three times independent experiments were expressed as means±SD. *P<0.05 compared with the control group for compound 3k-3t.
Figure 9C:
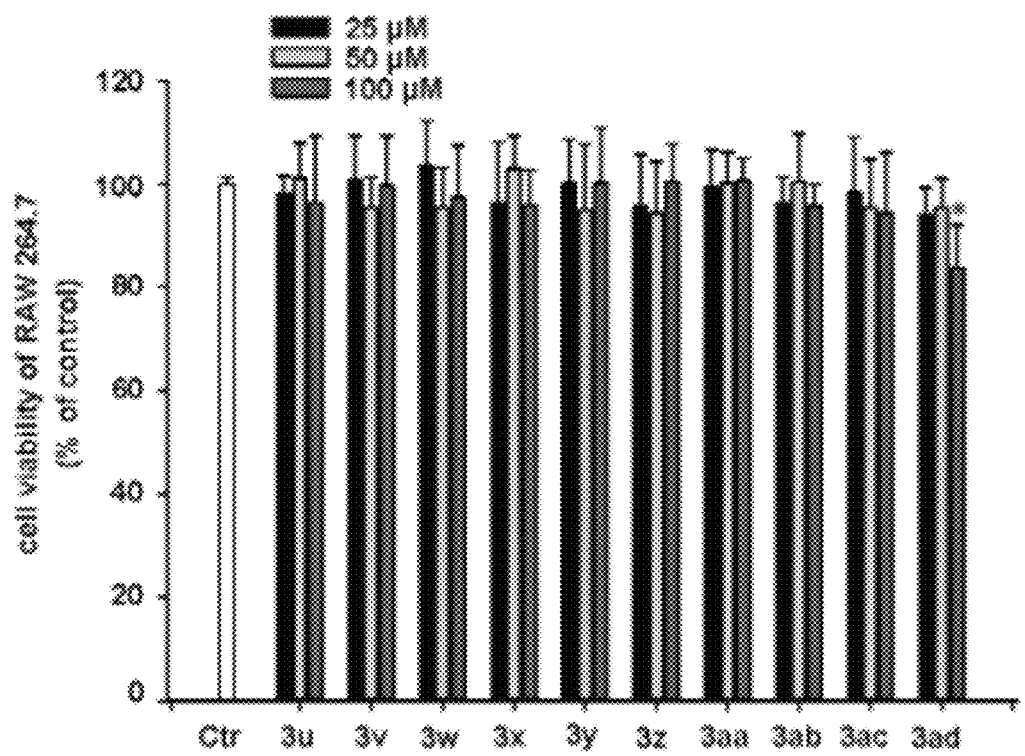
FIG. 9C shows the effect of compounds on the cell viability. RAW 264.7 cells were plated in a 96-well plate and treated with each compound (0, 25 μM, 50 μM and 100 μM) for 24 h. The viability of cells was tested by CCK8 assay. Data from three times independent experiments were expressed as means±SD. *P<0.05 compared with the control group for compound 3u-3ad.
Figure 9D:
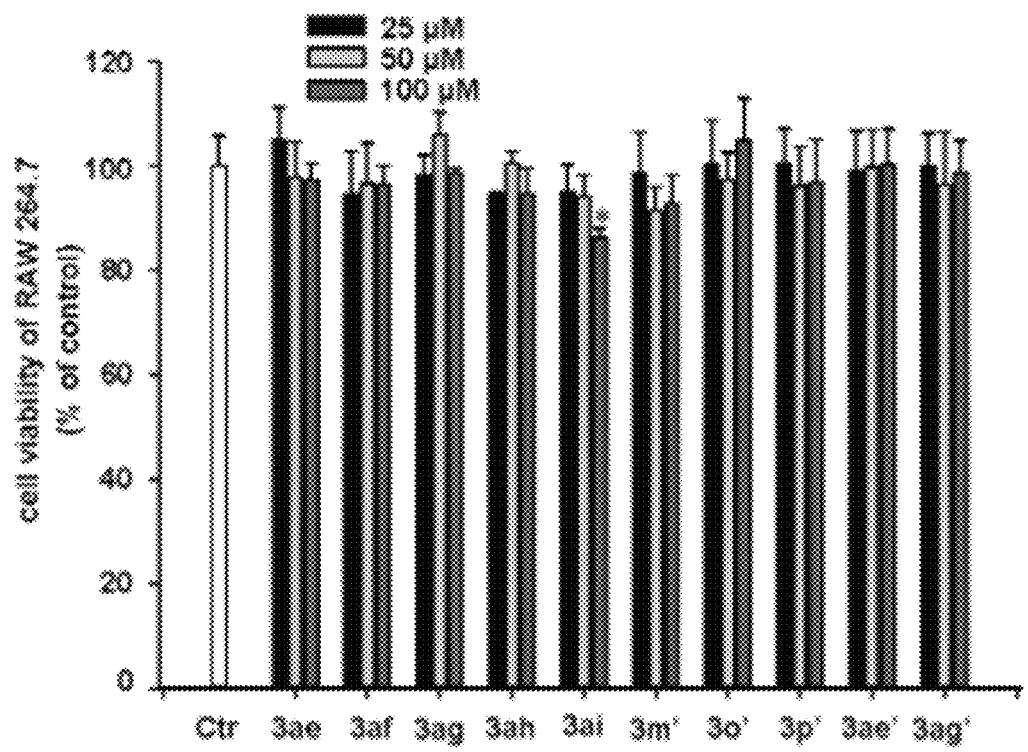
FIG. 9D shows the effect of compounds on the cell viability. RAW 264.7 cells were plated in a 96-well plate and treated with each compound (0, 25 μM, 50 μM and 100 μM) for 24 h. The viability of cells was tested by CCK8 assay. Data from three times independent experiments were expressed as means±SD. *P<0.05 compared with the control group for compound 3ae-3ag'.

To evaluate the influence of different configurations of the flavan-3-ols on the anti-inflammation activity, compounds (2R,3S)-3m, (2R,3S)-3o, (2R,3S)-3p, (2R,3S)-3ae, (2R,3S)-3ag, and their enantiomers (2S,3R)-3m', (2S,3R)-3o', (2S,3R)-3p', (2S,3R)-3ae', (2S,3R)-3ag' were selected. Then these ten compounds were evaluated for their anti-inflammation activity together with their racemic forms (rac-3m, rac-3o, rac-3p, rac-3ae and rac-3ag). The inhibition rate of IL-1β secretion was applied to evaluate the anti-inflammation effect of each compound. The inventor results revealed that compounds 3m, 3o, 3ag, 3ae showed higher inhibition rates than their enantiomers, 3m', 3o', 3ag', 3ae', and racemic mixtures (FIG. 8). Meanwhile, compound (2S,3R)-3p' exhibited higher inhibition rate of IL-1β secretion than its racemic mixture (FIG. 8). These results strongly suggested that the chirality plays an important role in the recognition between the biologically active molecules and their targets, and enantio-enriched flavanols always show higher inhibition rates than their racemic mixtures.

Data availability The X-ray crystallographic coordinates for structures reported in this Article have been deposited at the Cambridge Crystallographic Data Centre (CCDC), under deposition numbers CCDC 2056766. This data can be obtained free of charge from The Cambridge Crystallographic Data Centre via http://www.ccdc.cam.ac.uk/data_request/cif. The complete RNA-seq datasets in this manuscript captioned has been deposited at GEO database (http://www.ncbi.nlm.nih.gov/geo/) under accession ID GSE181052. For the general information and NMR analysis of the compounds in this invention, see the following information.

General Information

All the air or moisture sensitive reactions and manipulations were performed under an atmosphere of argon by using standard Schlenk techniques and Drybox (Mikrouna, Supper 1220/750). $^1$H NMR and $^{13}$C NMR spectra were recorded on Bruker-Avance 400 or 500 MHz spectrometer. CDCl$_3$ was used as solvent. Chemical shifts (δ) were reported in ppm with tetramethylsilane as internal standard, and J values were given in Hz. The following abbreviations were used to explain the multiplicities: s=singlet, d=doublet, dd=double of doublets, t=triplet, q=quartet, m=multiplet. Flash column chromatograph was carried out using 200-300 mesh silica gel at medium pressure. High resolution mass spectra (HRMS) were recorded on a LC-TOF spectrometer. ESI-HRMS data were acquired using a Thermo LTQ Orbitrap XL Instrument equipped with an ESI source. Optical rotation was obtained on a Rudolph Research Analytical (Atopol I). HPLC analysis was performed on Agilent 1260 series, UV detection monitored at 230 or 220 nm. Tetrahydrofuran was distilled over sodium. Melting points were measured on MP-450 (Hanon) melting point apparatus and uncorrected.

General method for Cu-catalyzed kinetic resolution a of chromenes via asymmetric hydroboration In a nitrogen-filled glovebox, a flame-dried screw-cap reaction tube equipped with a magnetic stir bar was charged with CuCl (0.01 mmol, 1.0 mg), (R, R)-Ph-BPE (0.012 mmol, 6.1 mg), NaOtBu (0.02 mmol, 1.9 mg) and anhydrous THF (0.6 mL) was added. Then, the reaction mixture was stirred for 15 min. 2-phenyl-2H-chromene 1a (0.20 mmol, 41.6 mg) and B$_2$(pin)$_2$ 2 (0.24 mmol, 60.9 mg) were added. The Schleck reaction vial was sealed with a rubber plug and taken out glovebox. The tube was allowed to stir at −35° C. for 5 min. Then, MeOH (0.2 mmol, 8 μL) was added. The resulting solution was allowed to stir at −35° C. for 24 h. NaBO$_3$·H$_2$O (0.5 mmol, 50.0 mg) and H$_2$O (0.6 mL) were added. The resulting mixture was allowed to stir at room temperature for 5 h. The reaction mixture was diluted with EtOAc (10 mL) and H$_2$O (3 mL). The aqueous layer was extracted with EtOAc (10×2 mL). The organic layer was dried over anhydrous Na$_2$SO$_4$, filtered, and concentrated under vacuum. The residue was purified by column chromatography on silica gel to get the corresponding hydroboration product 3a and the recovered starting material (R)-1a. The ee values of 3a and 1a were determined by HPLC. Diastereomeric ratio was determined by $^1$H NMR.

Characterization data ($^1$H NMR, $^{13}$C NMR, $^{19}$F NMR, HRMS, and HPLC) of the products (R)-2-Phenyl-2H-chromene (1a)

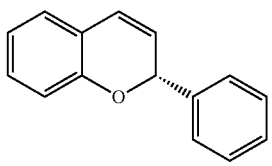 [SMILES: C1=C[C@H](c2ccccc2)Oc2ccccc21]

Light yellow oil, 46% yield; $[\alpha]^{20}_D$=+212 (c=0.4, CHCl$_3$) {(R) $[\alpha]^{20}_D$=+177.1 (c 0.5, CHCl$_3$)}[4]; ee was determined to be 99% by HPLC analysis with a Chiralcel OJ-H column (hexane/2-propanol 99:1, 1.0 mL/min, 230 nm); t$_r$ (major)=24.53 min, t$_r$ (minor)=28.62 min; $^1$H NMR (500 MHz, CDCl$_3$): δ 7.51-7.49 (m, 2H), 7.43-7.35 (m, 3H), 7.15 (td, J=10.0, 1.6 Hz, 1H), 7.05 (dd, J=7.4, 1.5 Hz, 1H), 6.91 (td, J=7.4, 0.8 Hz, 1H), 6.84 (d, J=8.1 Hz, 1H), 6.57 (dd, J=9.8, 1.6 Hz, 1H), 5.93 (t, J=2.9 Hz, 1H), 5.84 (dd, J=9.9, 3.4 Hz, 1H). $^{13}$C NMR (125 MHz, CDCl$_3$): δ 153.2, 140.9, 129.5, 128.7, 128.4, 127.1, 126.7, 124.9, 124.1, 121.4, 121.3, 116.1, 77.2.

(R)-2-(p-tolyl)-2H-chromene (1b)

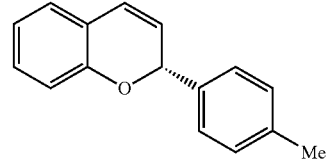 [SMILES: Cc1ccc([C@H]2C=Cc3ccccc3O2)cc1]

White solid, 45% yield; $[\alpha]^{20}_D$=+204 (c=0.23, CHCl$_3$) {(R) $[\alpha]^{20}_D$=+62.2 (c 0.5, CHCl$_3$)}[4]; ee was determined to be 99% by HPLC analysis with a Chiralcel IB column (hexane/2-propanol 99.5:0.5, 0.5 mL/min, 230 nm); t$_r$ (major)=11.18 min, t$_r$ (minor)=11.69 min; $^1$H NMR (500 MHz, CDCl$_3$): δ 7.37-7.34 (d, J=7.9 Hz, 2H), 7.18 (d, J=7.9 Hz, 2H), 7.11 (td, J=9.1, 1.5 Hz, 1H), 7.04 (dd, J=7.4, 1.3 Hz, 1H), 6.86 (td, J=7.4, 1.0 Hz, 1H), 6.79 (d, J=8.1 Hz, 1H), 6.55 (dd, J=9.8, 1.1 Hz, 1H), 5.89 (t, J=1.8 Hz, 1H), 5.81 (dd, J=9.9, 3.4 Hz, 1H), 2.36 (s, 3H). $^{13}$C NMR (125 MHz, CDCl$_3$): δ 153.2, 138.3, 137.9, 129.5, 129.4, 127.1, 126.6, 125.0, 124.0, 121.4, 121.1, 116.1, 77.3, 21.2.

(R)-2-(4-methoxyphenyl)-2H-chromene (1c)

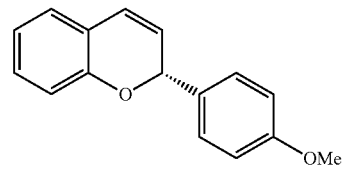 [SMILES: COc1ccc([C@H]2C=Cc3ccccc3O2)cc1]

White solid, 46% yield; $[\alpha]^{20}_D$=+253 (c=0.45, CHCl$_3$) {(R) $[\alpha]^{20}_D$=+64.7 (c 0.5, CHCl$_3$)}[4]; ee was determined to be 97% by HPLC analysis with a Chiralcel OJ-3 column (hexane/2-propanol 90:10, 1.0 mL/min, 230 nm); t$_r$ (major)=21.69 min, t$_r$ (minor)=27.74 min; $^1$H NMR (400 MHz, CDCl$_3$): δ 7.38 (d, J=8.7 Hz, 2H), 7.10 (td, J=7.8, 1.5 Hz, 1H), 7.01 (dd, J=7.4, 1.4 Hz, 1H), 6.91-6.84 (m, 3H), 6.76 (d, J=8.0 Hz, 1H), 6.55 (dd, J=9.8, 1.4 Hz, 1H), 5.87 (t, J=2.4 Hz, 1H), 5.79 (dd, J=9.8, 3.4 Hz, 1H), 3.80 (s, 3H). $^{13}$C NMR (125 MHz, CDCl$_3$): δ 159.8, 153.2, 132.9, 129.5, 128.7, 126.6, 125.0, 124.1, 121.4, 121.1, 116.1, 114.1, 76.8, 55.3.

(R)-2-(4-(benzyloxy)phenyl)-2H-chromene (1d)

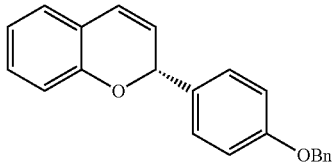 [SMILES: C1=C[C@H](c2ccc(OCc3ccccc3)cc2)Oc2ccccc21]

White solid, 42% yield; m.p. 92-93° C.; $[\alpha]^{20}_D$=+292 (c=0.53, CHCl$_3$); ee was determined to be 98% by HPLC analysis with a Chiralcel OD-H column (hexane/2-propanol 95:5, 1.0 mL/min, 230 nm); $t_r$ (minor)=15.96 min, $t_r$ (major)=17.32 min; $^1$H NMR (400 MHz, CDCl$_3$): δ 7.44-7.37 (m, 6H), 7.33 (m, 1H), 7.11 (m, 1H), 7.03-6.97 (m, 3H), 6.87 (t, J=7.4 Hz, 1H), 6.77 (d, J=10.1 Hz, 1H), 6.55 (dd, J=9.8, 1.5 Hz, 1H), 5.88 (m, 1H), 5.79 (dd, J=9.8, 3.4 Hz, 1H), 5.07 (s, 2H). $^{13}$C NMR (100 MHz, CDCl$_3$): δ 159.0, 153.1, 136.9, 133.2, 129.4, 128.7, 128.6, 128.0, 127.5, 126.6, 124.9, 124.0, 121.4, 121.1, 116.1, 115.0, 76.8, 70.0. HRMS (ESI) m/z: calcd for C$_{22}$H$_{19}$O$_2$[M+H]$^+$ 315.1380, found 315.1375.

(R)-2-(4-(methoxymethoxy)phenyl)-2H-chromene (1e)

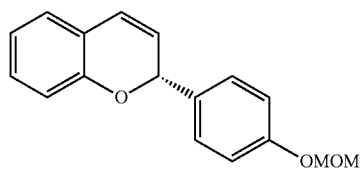

Colorless oil, 37% yield; $[\alpha]^{20}_D$=+102 (c=0.46, CHCl$_3$); ee was determined to be 98% by HPLC analysis with a Chiralcel AS-H column (hexane/2-propanol 90:10, 1.0 mL/min, 230 nm); $t_r$ (major)=8.74 min, $t_r$ (minor)=12.38 min; $^1$H NMR (500 MHz, CDCl$_3$): δ 7.40-7.39 (m, 2H), 7.12 (m, 1H), 7.06-7.01 (m, 3H), 6.87 (t, J=7.4 Hz, 1H), 6.78 (d, J=8.1 Hz, 1H), 6.56 (dd, J=9.8, 1.6 Hz, 1H), 5.89 (m, 1H), 5.80 (dd, J=9.9, 3.5 Hz, 1H), 5.18 (s, 2H), 3.49 (s, 3H). $^{13}$C NMR (125 MHz, CDCl$_3$): δ 157.4, 153.1, 134.1, 129.5, 128.7, 126.6, 124.9, 124.1, 121.4, 121.1, 116.3, 116.1, 94.4, 76.8, 56.0. HRMS (ESI) m/z: calcd for C$_{17}$H$_{17}$O$_3$ [M+H]$^+$ 269.1172, found 269.1167.

(R)-2-(4-fluorophenyl)-2H-chromene (1f)

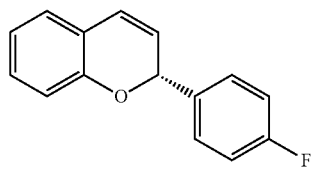 [SMILES: Fc1ccc([C@H]2C=Cc3ccccc3O2)cc1]

Colorless oil, 46% yield; $[\alpha]^{20}_D$=+123 (c=0.38, CHCl$_3$) {(R) $[\alpha]^{20}_D$=+17.4 (c 0.5, CHCl$_3$)}[4]; ee was determined to be >99% by HPLC analysis with a Chiralcel OJ-3 column (hexane/2-propanol 99:1, 1.0 mL/min, 230 nm); $t_r$ (major)=15.47 min; $^1$H NMR (500 MHz, CDCl$_3$): δ 7.45-7.42 (m, 2H), 7.12 (t, J=8.3 Hz, 1H), 7.07-7.01 (m, 3H), 6.88 (t, J=7.4 Hz, 1H), 6.77 (d, J=8.0 Hz, 1H), 6.55 (dd, J=9.8, 1.1 Hz, 1H), 5.90 (s, 1H), 5.80 (dd, J=9.8, 3.4 Hz, 1H). $^{13}$C NMR (125 MHz, CDCl$_3$): δ 163.7 (d, J=245.3 Hz), 136.6 (d, J=3.0 Hz), 129.6, 129.0 (d, J=8.2 Hz), 126.7, 124.5, 124.3, 121.3, 121.2, 116.1, 115.7 (d, J=21.6 Hz), 76.4. $^{19}$F NMR (376 MHz, CDCl$_3$): δ −113.60.

(R)-2-(4-chlorophenyl)-2H-chromene (1g)

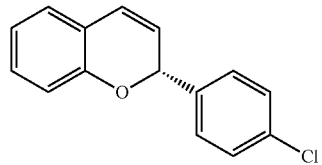 [SMILES: Clc1ccc([C@H]2C=Cc3ccccc3O2)cc1]

Colorless oil, 42% yield; $[\alpha]^{20}_D$=+134 (c=0.42, CHCl$_3$); ee was determined to be >99% by HPLC analysis with a Chiralcel OD-H column (hexane/2-propanol 99:1, 0.5 mL/min, 230 nm); $t_r$ (major)=11.89 min; $^1$H NMR (500 MHz, CDCl$_3$): δ 7.42-7.35 (m, 4H), 7.14 (td, J=7.8, 1.6 Hz, 1H), 7.04 (m, 1H), 6.90 (m, 1H), 6.82 (d, J=8.1 Hz, 1H), 6.56 (dd, J=9.8, 1.6 Hz, 1H), 5.90 (m, 1H), 5.78 (dd, J=9.8, 3.4 Hz, 1H). $^{13}$C NMR (125 MHz, CDCl$_3$): δ 152.9, 139.3, 134.2, 129.7, 128.9, 128.5, 126.7, 124.4, 124.3, 121.4, 121.2, 116.1, 76.3.

(R)-2-(4-bromophenyl)-2H-chromene (1h)

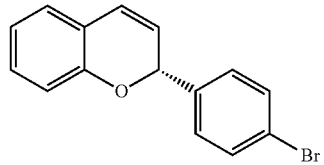

Colorless oil, 44% yield; $[\alpha]^{20}_D$=+62 (c=0.28, CHCl$_3$) {(R) $[\alpha]^{20}_D$=+19.3 (c 0.5, CHCl$_3$)}[4]; ee was determined to be >99% by HPLC analysis with a Chiralcel OJ-H column (hexane/2-propanol 98:2, 1.0 mL/min, 230 nm); $t_r$ (major)=15.37 min; $^1$H NMR (500 MHz, CDCl$_3$): δ 7.51 (d, J=8.4 Hz, 2H), 7.34 (d, J=8.4 Hz, 2H), 7.14 (td, J=7.9, 1.4 Hz, 1H), 7.03 (dd, J=7.4, 1.2 Hz, 1H), 6.90 (t, J=7.4 Hz, 1H), 6.81 (d, J=8.1 Hz, 1H), 6.56 (d, J=9.8 Hz, 1H), 5.90 (m, 1H), 5.78 (dd, J=9.8, 3.5 Hz, 1H). $^{13}$C NMR (125 MHz, CDCl$_3$): δ 152.9, 139.8, 131.8, 129.7, 128.8, 126.7, 124.4, 124.2, 122.4, 121.4, 121.2, 116.1, 76.3.

(R)-2-(4-(trifluoromethyl)phenyl)-2H chromene (i)

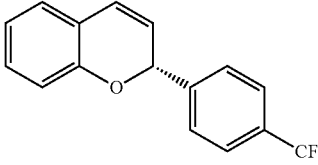

White solid, 39% yield; $[\alpha]^{20}_D$=+101 (c=0.33, CHCl$_3$); ee was determined to be 99.5% by HPLC analysis with a Chiralcel OD-H column (hexane/2-propanol 98:2, 0.5 mL/min, 230 nm); $t_r$ (major)=11.85 min, $t_r$ (minor)=13.15 min; $^1$H NMR (500 MHz, CDCl$_3$): δ 7.61 (dd, J=29.1, 8.2 Hz, 4H), 7.15 (td, J=8.0, 1.5 Hz, 1H), 7.03 (dd, J=7.4, 1.3 Hz, 1H), 6.90 (td, J=7.5, 1.05 Hz, 1H), 6.83 (d, J=8.1 Hz, 1H), 6.56 (dd, J=9.8, 1.1 Hz, 1H), 5.98 (br s, 1H), 5.80 (dd, J=9.8, 3.5 Hz, 1H). $^{13}$C NMR (125 MHz, CDCl$_3$): δ 152.9, 144.7, 130.6 (q, J=128.6 Hz), 130.0, 127.2, 126.8, 125.7 (q, J=3.7 Hz), 125.2 (q, J=270.4 Hz), 124.6, 123.9, 121.6, 121.2, 116.0, 76.2. $^{19}$F NMR (376 MHz, CDCl$_3$): δ −62.57.

(R)-2-(o-tolyl)-2H-chromene (1j)

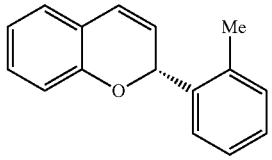 [SMILES: Cc1ccccc1[C@H]1C=Cc2ccccc2O1]

Colorless oil, 41% yield; $[\alpha]^{20}_D$=+137 (c=0.50, CH$_2$Cl$_2$); ee was determined to be 99.7% by HPLC analysis with a Chiralcel OD-H column (hexane/2-propanol 99:1, 0.5 mL/min, 230 nm); $t_r$ (major)=11.96 min, $t_r$ (minor)=12.72 min; $^1$H NMR (500 MHz, CDCl$_3$): δ 7.46 (d, J=6.8 Hz, 1H), 7.21-7.16 (m, 3H), 7.08 (td, J=7.6, 1.5 Hz, 1H), 6.98 (dd, J=7.5, 1.3 Hz, 1H), 6.84 (t, J=7.5 Hz, 1H), 6.77 (d, J=8.1 Hz, 1H), 6.52 (dd, J=9.8, 1.8 Hz, 1H), 6.13 (t, J=2.5 Hz, 1H), 5.73 (dd, J=9.8, 3.1 Hz, 1H), 2.44 (s, 3H). $^{13}$C NMR (125 MHz, CDCl$_3$): δ 153.6, 138.4, 136.1, 130.9, 129.5, 128.4, 127.8, 126.7, 126.3, 124.6, 124.5, 121.5, 121.3, 116.0, 74.8, 19.3.

(R)-2-(m-tolyl)-2H-chromene (1k)

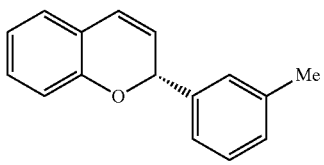 [SMILES: Cc1cccc([C@H]2C=Cc3ccccc3O2)c1]

Colorless oil, 43% yield; $[\alpha]^{20}_D$=+251 (c=0.32, CHCl$_3$); ee was determined to be 99% by HPLC analysis with a Chiralcel AS-H column (hexane/2-propanol 99:1, 0.5 mL/min, 230 nm); $t_r$ (major)=8.10 min, $t_r$ (minor)=9.00 min; $^1$H NMR (400 MHz, CDCl$_3$): δ 7.30-7.28 (m, 3H), 7.17-7.12 (m, 2H), 7.04 (dd, J=7.4, 1.5 Hz, 1H), 6.89 (td, J=7.4, 0.9 Hz, 1H), 6.82 (d, J=8.0 Hz, 1H), 6.55 (dd, J=9.8, 1.7 Hz, 1H), 5.92 (t, J=3.0 Hz, 1H), 5.81 (dd, J=9.8, 3.3 Hz, 1H), 2.39 (s, 3H). $^{13}$C NMR (125 MHz, CDCl$_3$): δ 153.2, 140.8, 138.4, 129.5, 129.2, 128.7, 127.8, 126.6, 125.0, 124.2, 124.0, 121.3, 121.2, 116.0, 77.3, 21.5.

(R)-2-(3,5-dimethylphenyl)-2H-chromene (1l)

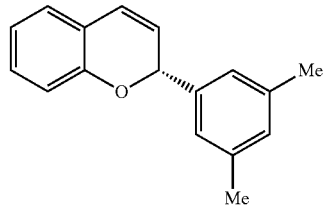 [SMILES: Cc1cc(C)cc([C@H]2C=Cc3ccccc3O2)c1]

White solid, 47% yield; $[\alpha]^{20}_D$=+236 (c=0.45, CHCl$_3$); ee was determined to be >99% by HPLC analysis with a Chiralcel AS-H column (hexane/2-propanol 99:1, 0.5 mL/min, 230 nm); $t_r$ (major)=7.63 min; $^1$H NMR (500 MHz, CDCl$_3$): δ 7.16 (td, J=7.8, 1.7 Hz, 1H), 7.13 (s, 2H), 7.06 (dd, J=7.5, 1.6 Hz, 1H), 7.02 (s, 1H), 6.93 (td, J=7.5, 1.1 Hz, 1H), 6.86 (d, J=8.0 Hz, 1H), 6.57 (dd, J=10.4, 2.3 Hz, 1H), 5.91 (t, J=2.7 Hz, 1H), 5.82 (dd, J=9.8, 3.2 Hz, 1H), 2.38 (s, 6H). $^{13}$C NMR (125 MHz, CDCl$_3$): δ 153.4, 140.9, 138.3, 130.2, 129.5, 126.7, 125.2, 125.0, 123.9, 121.4, 121.2, 116.0, 77.5, 21.4.

(R)-2-(naphthalen-2-yl)-2H-chromene (1m)

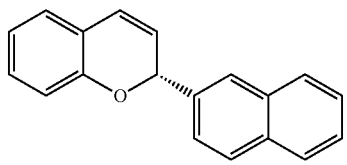 [SMILES: C1=C[C@H](c2ccc3ccccc3c2)Oc2ccccc21]

White solid, 42% yield; $[\alpha]^{20}_D$=+311 (c=0.46, CHCl$_3$); ee was determined to be >99% by HPLC analysis with a Chiralcel OJ-3 column (hexane/2-propanol 98:2, 1.0 mL/min, 230 nm); $t_r$ (major)=30.42 min; $^1$H NMR (500 MHz, CDCl$_3$): δ 7.91-7.86 (m, 4H), 7.64 (d, J=8.4 Hz, 1H), 7.52-7.51 (m, 2H), 7.16 (t, J=7.6 Hz, 1H), 7.07 (d, J=7.3 Hz, 1H), 6.92 (t, J=7.3 Hz, 1H), 6.86 (d, J=7.8 Hz, 1H), 6.61 (d, J=9.8 Hz, 1H), 6.12 (s, 1H), 5.90 (dd, J=9.8, 3.2 Hz, 1H). $^{13}$C NMR (125 MHz, CDCl$_3$): δ 153.2, 138.1, 133.3, 133.2, 129.6, 128.6, 128.2, 127.7, 126.7, 126.3, 126.1, 125.0, 124.7, 124.3, 121.4, 121.3, 116.1, 77.3.

(S)-2-(naphthalen-2-yl)-2H-chromene (1m')

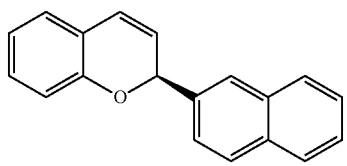 [SMILES: C1=C[C@@H](c2ccc3ccccc3c2)Oc2ccccc21]

White solid, 45% yield; $[\alpha]^{20}_D$=−384 (c=0.58, CHCl$_3$); ee was determined to be 98% by HPLC analysis with a Chiralcel AS-H column (hexane/2-propanol 98:2, 1.0 mL/min, 230 nm); $t_r$ (minor)=5.22 min, $t_r$ (major)=6.12 min;

(R)-2-(thiophen-2-yl)-2H-chromene (1n)

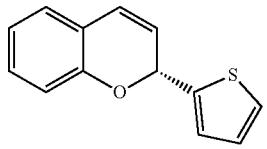 [SMILES: C1=C[C@H](c2cccs2)Oc2ccccc21]

Yellow oil, 40% yield; $[\alpha]^{20}_D=+92$ (c=0.3, CHCl$_3$);ee was determined to be 96% by HPLC analysis with a Chiralcel AD-H column (hexane/2-propanol 99:1, 0.5 mL/min, 230 nm); t$_r$ (major)=10.33 min, t$_r$ (minor)=10.69 min; $^1$H NMR (500 MHz, CDCl$_3$): δ 7.31 (dd, J=5.1, 1.2 Hz, 1H), 7.17-7.13 (m, 2H), 7.07 (dd, J=7.5, 1.6 Hz, 1H), 7.00 (dd, J=5.5, 3.6 Hz, 1H), 6.92 (td, J=7.4, 1.1 Hz, 1H), 6.84 (d, J=8.1 Hz, 1H), 6.62 (dd, J=9.8, 0.5 Hz, 1H), 6.16 (m, 1H), 5.95 (dd, J=9.8, 3.9 Hz, 1H). $^{13}$C NMR (125 MHz, CDCl$_3$): δ 152.5, 143.7, 129.6, 126.8, 126.7, 126.4, 126.2, 124.7, 123.9, 121.5, 121.4, 116.5, 71.7. HRMS (ESI) m/z: calcd for C$_{13}$H$_{11}$OS [M+H]$^+$ 215.0531, found 215.0524.

(R)-2-(furan-2-yl)-2H-chromene (1o)

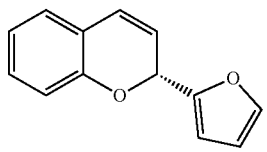 [SMILES: C1=C[C@H](c2ccco2)Oc2ccccc21]

Yellow oil, 41% yield; $[\alpha]^{20}_D$+11.5 (c=0.27, CHCl$_3$); ee was determined to be 92% by HPLC analysis with a Chiralcel D-H column (hexane/2-propanol 99:1, 1.0 mL/min, 230 nm); t$_r$ (major)=6.71 min, t$_r$ (minor)=7.19 min; $^1$H NMR (500 MHz, CDCl$_3$): δ 7.45 (m, 1H), 7.12 (td, J=7.9, 1.6 Hz, 1H), 7.05 (dd, J=7.5, 1.6 Hz, 1H), 6.89 (td, J=7.5, 1.1 Hz, 1H), 6.82 (d, J=8.1 Hz, 1H), 6.63 (dd, J=9.8, 0.8 Hz, 1H), 6.38 (d, J=3.3 Hz, 1H), 6.34 (m, 1H), 5.95 (dd, J=3.9, 1.4 Hz, 1H), 5.85 (dd, J=9.8, 4.0 Hz, 1H). $^{13}$C NMR (125 MHz, CDCl$_3$): δ 152.7, 152.6, 143.3, 129.5, 126.7, 125.5, 121.5, 121.4, 121.2, 116.3, 110.4, 109.5, 69.6. HRMS (ESI) m/z: calcd for C$_{13}$H$_{11}$O$_2$[M+H]$^+$ 199.0754, found 199.0755.

(S)-2-(furan-2-yl)-2H-chromene (1o')

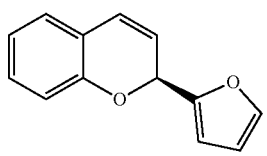 [SMILES: C1=C[C@@H](c2ccco2)Oc2ccccc21]

Yellow oil, 45% yield; $[\alpha]^{20}_D=-59$ (c=0.42, CHCl$_3$); ee was determined to be 86% by HPLC analysis with a Chiralcel OD-H column (hexane/2-propanol 99:1, 1.0 mL/min, 230 nm); t$_r$ (minor)=6.73 min, t$_r$ (major)=7.28 min.

(S)-2-propyl-2H-chromene (1p)

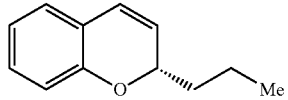 [SMILES: CCC[C@H]1C=Cc2ccccc2O1]

Yellow oil, 35% yield; $[\alpha]^{20}_D=+62$ (c=0.37, CH$_2$Cl$_2$); ee was determined to be >99% by HPLC analysis with a Chiralcel OJ-H column (hexane/2-propanol 99:1, 1.0 mL/min, 230 nm); t$_r$ (major)=5.78 min; $^1$H NMR (500 MHz, CDCl$_3$): δ 7.10 (m, 1H), 6.95 (dd, J=7.4, 1.6 Hz, 1H), 6.85 (m, 1H), 6.79 (d, J=8.1 Hz, 1H), 6.40 (m, 1H), 5.68 (dd, J=9.9, 3.4 Hz, 1H), 4.87 (m, 1H), 1.81 (m, 1H), 1.64 (m, 1H), 1.58 (m, 1H), 1.51 (m, 1H), 0.97 (t, J=7.4 Hz, 3H). 13C NMR (125 MHz, CDCl$_3$): δ 153.5, 129.1, 126.4, 126.0, 123.9, 122.1, 116.0, 74.9, 37.5, 18.1, 14.0.

(R)-2-propyl-2H-chromene (1p')

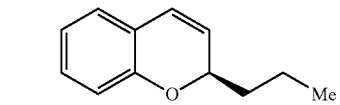 [SMILES: CCC[C@@H]1C=Cc2ccccc2O1]

Yellow oil, 32% yield; $[\alpha]^{20}_D=-47$ (c=0.31, CH$_2$Cl$_2$); ee was determined to be >99% by HPLC analysis with a Chiralcel OJ-H column (hexane/2-propanol 99:1, 1.0 mL/min, 230 nm); t$_r$ (minor)=6.38 min, t$_r$ (major)=7.05 min.

(R)-5-methyl-2-phenyl-2H-chromene (1q)

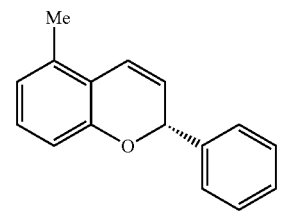 [SMILES: Cc1cccc2c1C=C[C@H](c1ccccc1)O2]

Yellow oil, 47% yield; $[\alpha]^{20}_D=+206$ (c=0.52, CHCl$_3$); ee was determined to be 97% by HPLC analysis with a Chiralcel OJ-H column (hexane/2-propanol 97:3, 1.0 mL/min, 230 nm); t$_r$ (major)=16.39 min, t$_r$ (minor)=19.52 min; $^1$H NMR (500 MHz, CDCl$_3$): δ 7.47-7.45 (m, 2H), 7.39-7.36 (m, 2H), 7.32 (m, 1H), 7.01 (t, J=7.8 Hz, 1H), 6.74-6.71 (m, 2H), 6.67 (d, J=8.1 Hz, 1H), 5.86-5.83 (m, 2H), 2.32 (s, 3H). $^{13}$C NMR (125 MHz, CDCl$_3$): δ 153.4, 140.9, 134.3, 128.9, 128.7, 128.3, 127.0, 124.8, 123.0, 121.3, 120.0, 114.1, 76.5, 18.5. HRMS (ESI) m/z: calcd for C$_{16}$H$_{15}$O [M+H]$^+$ 223.1117, found 223.1114.

(R)-6-methyl-2-phenyl-2H-chromene (1r)

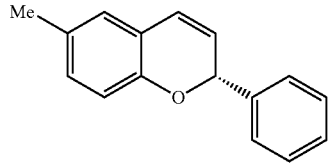 [SMILES: Cc1ccc2c(c1)C=C[C@H](c1ccccc1)O2]

Yellow oil, 47% yield; $[\alpha]^{20}_D$=+26 (c=0.41, CHCl$_3$); ee was determined to be >99% by HPLC analysis with a Chiralcel OJ-H column (hexane/2-propanol 98:2, 1.0 mL/min, 230 nm); t$_r$ (major)=17.12 min; $^1$H NMR (500 MHz, CDCl$_3$): δ 7.52-7.51 (m, 2H), 7.44-7.36 (m, 3H), 6.99 (dd, J=8.0, 1.8 Hz, 1H), 6.89 (d, J=1.8 Hz, 1H), 6.79 (d, J=8.4 Hz, 1H), 6.57 (dd, J=9.8, 1.8 Hz, 1H), 5.94 (m, 1H), 5.86 (dd, J=9.8, 3.4 Hz, 1H), 2.32 (s, 3H). $^{13}$C NMR (125 MHz, CDCl$_3$): δ 159.8, 153.2, 132.9, 129.5, 128.7, 126.6, 124.9, 124.1, 121.4, 121.1, 116.1, 114.1, 76.8, 55.3.

(R)-7-methyl-2-phenyl-2H-chromene (1s)

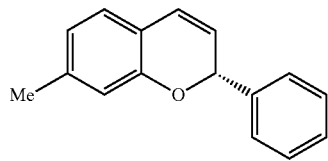 [SMILES: Cc1ccc2c(c1)O[C@@H](c1ccccc1)C=C2]

White solid, 43% yield; $[\alpha]^{20}_D$=+48 (c=0.72, CHCl$_3$); ee was determined to be 99% by HPLC analysis with a Chiralcel OD-H column (hexane/2-propanol 99:1, 0.5 mL/min, 230 nm); t$_r$ (minor)=9.47 min, t$_r$ (major)=10.17 min; $^1$H NMR (500 MHz, CDCl$_3$): δ 7.50-7.48 (m, 2H), 7.42-7.39 (m, 3H), 7.35 (m, 1H), 6.94 (d, J=7.5 Hz, 1H), 6.72 (d, J=7.5 Hz, 1H), 6.55 (d, J=9.9 Hz, 1H), 5.93 (s, 1H), 5.78 (dd, J=9.9, 1.1 Hz, 1H), 2.30 (s, 3H). $^{13}$C NMR (125 MHz, CDCl$_3$): δ 153.1, 141.0, 139.9, 128.7, 128.4, 127.1, 126.4, 123.9, 123.8, 121.9, 118.8, 116.7, 77.2, 21.5.

(R)-8-methyl-2-phenyl-2H-chromene (1t)

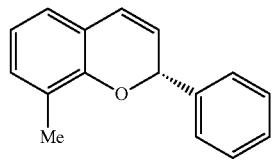 [SMILES: Cc1cccc2c1O[C@@H](c1ccccc1)C=C2]

Yellow oil, 42% yield; $[\alpha]^{20}_D$=+118 (c=0.45, CHCl$_3$); ee was determined to be 99% by HPLC analysis with a Chiralcel OJ-3 column (hexane/2-propanol 95:5, 1.0 mL/min, 230 nm); t$_r$ (major)=8.27 min, t$_r$ (minor)=11.12 min; $^1$H NMR (500 MHz, CDCl$_3$): δ 7.48-7.46 (m, 2H), 7.40-7.36 (m, 2H), 7.33 (m, 1H), 7.00 (d, J=6.8 Hz, 1H), 6.88 (m, 1H), 6.79 (m, 1H), 6.54 (dt, J=9.8, 2.0 Hz, 1H), 5.96 (m, 1H), 5.84 (m, 1H), 2.18 (s, 3H). $^{13}$C NMR (125 MHz, CDCl$_3$): δ 151.2, 141.3, 131.0, 128.6 (2C), 128.1, 126.7 (2C), 125.2, 124.5, 124.3 (2C), 120.9, 120.6, 76.7, 15.6.

(R)-5,7-dimethyl-2-phenyl-2H-chromene (1u)

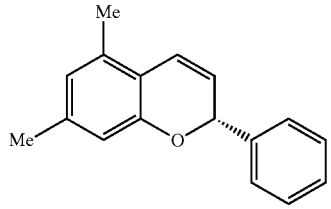 [SMILES: Cc1cc(C)c2c(c1)O[C@@H](c1ccccc1)C=C2]

Colorless oil, 41% yield; $[\alpha]^{20}_D$=+83 (c=0.47, CHCl$_3$); ee was determined to be 96% by HPLC analysis with a Chiralcel OD-H column (hexane/2-propanol 95:5, 1.0 mL/min, 230 nm); t$_r$ (minor)=8.97 min, t$_r$ (major)=9.78 min; $^1$H NMR (500 MHz, CDCl$_3$): δ 7.48-7.47 (m, 2H), 7.40-7.37 (m, 2H), 7.34 (m, 1H), 6.72 (dd, J=9.9, 1.2 Hz, 1H), 6.57 (s, 1H), 6.54 (s, 1H), 5.85 (m, 1H), 5.81 (dd, J=9.9, 3.4 Hz, 1H), 2.31 (s, 3H), 2.25 (s, 3H). $^{13}$C NMR (125 MHz, CDCl$_3$): δ 153.3, 141.1, 139.1, 134.0, 128.6, 128.2, 127.0, 123.8, 123.6, 121.2, 117.4, 114.6, 76.5, 21.4, 18.3.

(R)-6,7-dimethyl-2-phenyl-2H-chromene (1v)

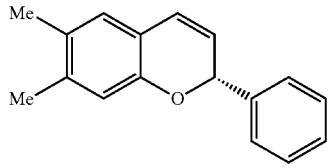 [SMILES: Cc1cc2c(cc1C)O[C@@H](c1ccccc1)C=C2]

White solid, 39% yield; $[\alpha]^{20}_D$=+358 (c=0.44, CHCl$_3$); ee was determined to be >99% by HPLC analysis with a Chiralcel OJ-H column (hexane/2-propanol 97:3, 1.0 mL/min, 230 nm); t$_r$ (major)=21.93 min; $^1$H NMR (500 MHz, CDCl$_3$): δ 7.46-7.45 (m, 2H), 7.38-7.35 (m, 2H), 7.32 (m, 1H), 6.79 (s, 1H), 6.62 (s, 1H), 6.50 (d, J=9.8 Hz, 1H), 5.87 (m, 1H), 5.74 (dd, J=9.8, 3.4 Hz, 1H), 2.18 (s, 3H), 2.17 (s, 3H). $^{13}$C NMR (125 MHz, CDCl$_3$): δ 151.1, 141.1, 138.1, 128.9, 128.6, 128.2, 127.5, 127.0, 123.9, 123.8, 118.9, 117.1, 77.0, 19.9, 18.8. HRMS (ESI) m/z: calcd for C$_{17}$H$_{17}$O [M+H]$^+$ 237.1274, found 237.1272.

(R)-5-methoxy-2-phenyl-2H-chromene (1w)

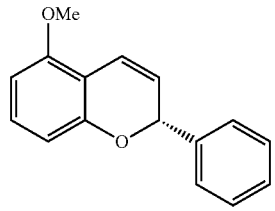 [SMILES: COc1cccc2c1C=C[C@H](c1ccccc1)O2]

White solid, 48% yield; $[\alpha]^{20}_D$=+72 (c=0.60, CHCl$_3$); ee was determined to be 96% by HPLC analysis with a Chiralcel OJ-3 column (hexane/2-propanol 95:5, 1.0 mL/min, 230 nm); t$_r$ (major)=20.27 min, t$_r$ (minor)=25.03 min; $^1$H NMR (500 MHz, CDCl$_3$): δ 7.48-7.46 (m, 2H), 7.39-7.36 (m, 2H), 7.33 (m, 1H), 7.06 (t, J=9.9 Hz, 1H), 6.90 (dd, J=8.9, 1.3 Hz, 1H), 6.46 (dd, J=14.3, 8.1 Hz, 2H), 5.87 (m, 1H), 5.77 (dd, J=10.0, 3.5 Hz, 1H), 3.84 (s, 3H). 13C NMR (125 MHz, CDCl$_3$): δ 155.3, 153.9, 140.8, 129.3, 128.6, 128.3, 127.1, 122.9, 118.8, 110.8, 109.1, 103.4, 76.7, 55.6.

(R)-6-methoxy-2-phenyl-2H-chromene (1x)

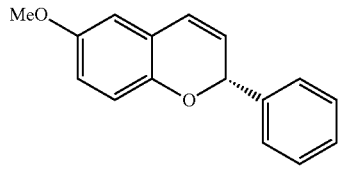 [SMILES: COc1ccc2c(c1)C=C[C@H](c1ccccc1)O2]

White solid, 42% yield; $[\alpha]^{20}_D$=+110 (c=0.36, CHCl$_3$); ee was determined to be 99% by HPLC analysis with a Chiralcel OD-H column (hexane/2-propanol 95:5, 1.0 mL/min, 230 nm); t$_r$ (major)=6.54 min, t$_r$ (minor)=7.33 min; $^1$H NMR (500 MHz, CDCl$_3$): δ 7.48-7.46 (m, 2H), 7.40-7.32 (m, 3H), 6.76 (d, J=8.9 Hz, 1H), 6.70 (dd, J=8.7, 3.0 Hz, 1H), 6.61 (d, J=3.0 Hz, 1H), 6.53 (m, 1H), 5.88-5.85 (m, 2H), 3.77 (s, 3H). $^{13}$C NMR (125 MHz, CDCl$_3$): δ 154.1, 147.1, 140.7, 128.7, 128.4, 127.1, 125.9, 124.2, 122.1, 116.6, 114.5, 111.8, 77.0, 55.8.

(R)-7-methoxy-2-phenyl-2H-chromene (1y)

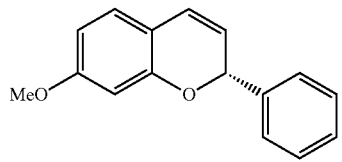 [SMILES: COc1ccc2c(c1)O[C@@H](c1ccccc1)C=C2]

Colorless oil, 40% yield; $[\alpha]^{20}_D$=+124 (c=0.45, CHCl$_3$); ee was determined to be 88% by HPLC analysis with a Chiralcel OD-H column (hexane/2-propanol 99:1, 1.0 mL/min, 230 nm); t$_r$ (major)=8.12 min, t$_r$ (minor)=8.86 min; $^1$H NMR (500 MHz, CDCl$_3$): δ 7.49-7.47 (m, 2H), 7.41-7.38 (m, 2H), 7.35 (m, 1H), 6.95 (d, J=8.3 Hz, 1H), 6.52 (dd, J=9.8, 1.5 Hz, 1H), 6.46 (dd, J=8.3, 2.5 Hz, 1H), 6.42 (d, J=2.2 Hz, 1H), 5.91 (m, 1H), 5.68 (dd, J=9.8, 3.4 Hz, 1H), 3.76 (s, 3H). $^{13}$C NMR (125 MHz, CDCl$_3$): δ 160.9, 154.4, 140.9, 128.7, 128.4, 127.3, 127.1, 123.7, 121.9, 114.7, 107.1, 101.8, 77.3, 55.3.

(R)-8-methoxy-2-phenyl-2H-chromene (1z)

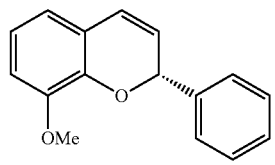 [SMILES: COc1cccc2c1O[C@@H](c1ccccc1)C=C2]

Colorless oil, 38% yield; $[\alpha]^{20}_D$=+198 (c=0.46, CHCl$_3$); ee was determined to be 97% by HPLC analysis with a Chiralcel OJ-H column (hexane/2-propanol 80:20, 1.0 mL/min, 220 nm); t$_r$ (minor)=13.22 min, t$_r$ (major)=21.39 min; $^1$H NMR (500 MHz, CDCl$_3$): δ 7.49-7.46 (m, 2H), 7.37-7.34 (m, 2H), 7.31 (m, 1H), 6.84-6.78 (m, 2H), 6.67 (m, 1H), 6.53 (m, 1H), 5.99 (m, 1H), 5.86 (dd, J=9.8, 3.7 Hz, 1H), 3.82 (s, 3H). $^{13}$C NMR (125 MHz, CDCl$_3$): δ 147.9, 142.1, 140.8, 128.6, 128.3, 126.9, 125.0, 123.8, 122.0, 120.8, 119.0, 112.7, 77.0, 56.2.

(R)-6,7-dimethoxy-2-phenyl-2H-chromene (1aa)

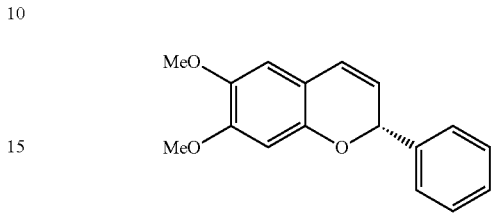

Red solid, 40% yield; $[\alpha]^{20}_D$=+175 (c=0.51, CHCl$_3$); ee was determined to be 83% by HPLC analysis with a Chiralcel OD-H column (hexane/2-propanol 95:5, 1.0 mL/min, 230 nm); t$_r$ (major)=9.71 min, t$_r$ (minor)=11.85 min; $^1$H NMR (500 MHz, CDCl$_3$): δ 7.47-7.46 (m, 2H), 7.39-7.36 (m, 2H), 7.33 (m, 1H), 6.57 (s, 1H), 6.47 (m, 1H), 6.44 (s, 1H), 5.85 (m, 1H), 5.69 (dd, J=9.7, 3.4 Hz, 1H), 3.84 (s, 3H), 3.81 (s, 3H). $^{13}$C NMR (125 MHz, CDCl$_3$): δ 149.9, 147.6, 143.4, 140.8, 128.7, 128.4, 127.1, 123.9, 122.3, 113.3, 109.8, 100.8, 77.1, 56.5, 55.9.

(R)-6-(methoxymethoxy)-2-phenyl-2H-chromene (1ab)

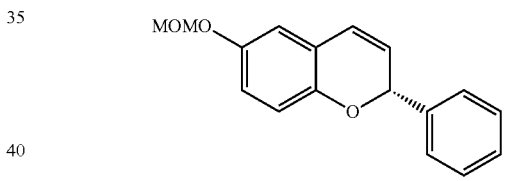

White solid, 34% yield; m.p. 69-70° C.; $[\alpha]^{20}_D$=+84 (c=0.42, CHCl$_3$); ee was determined to be 96% by HPLC analysis with a Chiralcel OD-H column (hexane/2-propanol 98:2, 1.0 mL/min, 230 nm); t$_r$ (major) 11.17 min, t$_r$ (minor) 11.71 min; $^1$H NMR (500 MHz, CDCl$_3$): δ 7.46-7.44 (m, 2H), 7.38 (m, 2H), 7.33 (m, 1H), 6.81 (dd, J=8.7, 2.9 Hz, 1H), 6.76-6.72 (m, 2H), 6.51 (d, J=9.4 Hz, 1H), 5.87-5.83 (m, 2H), 5.12 (s, 2H), 3.49 (s, 3H). $^{13}$C NMR (125 MHz, CDCl$_3$): δ 151.6, 148.1, 140.7, 128.7, 128.4, 127.1, 125.8, 124.1, 122.0, 117.5, 116.6, 114.5, 95.3, 76.8, 55.9. HRMS (ESI) m/z: calcd for C$_{17}$H$_{17}$O$_3$[M+H]$^+$ 269.1172, found 269.1168.

(R)-2-phenyl-2H-chromen-6-ol (1ac)

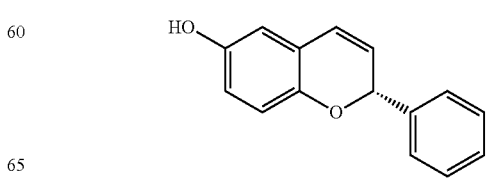

White solid, 42% yield; m.p. 81-82° C.; $[\alpha]^{20}_D$=+200 (c=0.48, CHCl$_3$); ee was determined to be 95% by HPLC analysis with a Chiralcel OD-H column (hexane/2-propanol 90:10, 1.0 mL/min, 230 nm); $t_r$ (minor)=13.09 min, $t_r$ (major)=14.25 min; $^1$H NMR (500 MHz, CDCl$_3$): δ 7.46-7.45 (m, 2H), 7.39-7.32 (m, 3H), 6.69 (d, J=8.6 Hz, 1H), 6.58 (dd, J=8.6, 3.0 Hz, 1H), 6.53 (d, J=3.0 Hz, 1H), 6.47 (dd, J=10.8, 3.0 Hz, 1H), 5.87-5.84 (m, 2H), 4.98 (s, 1H). $^{13}$C NMR (125 MHz, CDCl$_3$): δ 149.7, 147.0, 140.5, 128.7, 128.4, 127.1, 126.1, 124.0, 122.3, 116.7, 115.9, 113.2, 77.0. HRMS (ESI) m/z: calcd for C$_{15}$H$_{13}$O$_2$[M+H]+ 225.0910, found 225.0908.

(R)-6-fluoro-2-phenyl-2H-chromene (1ad)

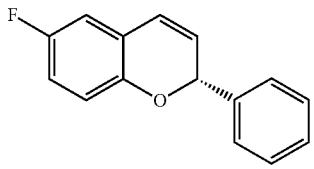 [SMILES: Fc1ccc2c(c1)C=C[C@H](c1ccccc1)O2]

Yellow solid, 44% yield; $[\alpha]^{20}_D$=+323 (c=0.47, CH$_2$Cl$_2$); ee was determined to be >99 by HPLC analysis with a Chiralcel OJ-H column (hexane/2-propanol 95:5, 1.0 mL/min, 230 nm); $t_r$ (major)=15.32 min; $^1$H NMR (500 MHz, CDCl$_3$): δ 7.50-7.49 (m, 2H), 7.44-7.37 (m, 3H), 6.86 (td, J=8.6, 3.2 Hz, 1H), 6.79-6.76 (m, 2H), 6.54 (dd, J=7.5, 1.1 Hz, 1H), 5.94-5.91 (m, 2H). $^{13}$C NMR (125 MHz, CDCl$_3$): δ 157.4 (d, J=237.1 Hz), 149.0 (d, J=2.3 Hz), 140.3, 128.7, 128.6, 127.1, 126.4, 123.5 (d, J=1.7 Hz), 122.3 (d, J=8.4 Hz), 116.9 (d, J=8.0 Hz), 115.5 (d, J=23.0 Hz), 112.8 (d, J=23.6 Hz), 77.2. $^{19}$F NMR (376 MHz, CDCl$_3$): δ −123.17.

(R)-6-chloro-2-phenyl-2H-chromene (1ae)

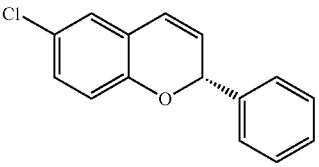 [SMILES: Clc1ccc2c(c1)C=C[C@H](c1ccccc1)O2]

Yellow solid, 43% yield; $[\alpha]^{20}_D$=+52 (c=0.34, CHCl$_3$); ee was determined to be 99% by HPLC analysis with a Chiralcel OJ-H column (hexane/2-propanol 95:5, 1.0 mL/min, 230 nm); $t_r$ (major)=12.68 min, $t_r$ (minor)=15.32 min; $^1$H NMR (500 MHz, CDCl$_3$): δ 7.50-7.48 (m, 2H), 7.45-7.38 (m, 3H), 7.10 (dd, J=8.6, 2.6 Hz, 1H), 7.04 (d, J=2.6 Hz, 1H), 6.77 (d, J=8.6 Hz, 1H), 6.51 (dd, J=9.9, 1.7 Hz, 1H), 5.96 (m, 1H), 5.89 (dd, J=9.9, 3.5 Hz, 1H). 13C NMR (125 MHz, CDCl$_3$): δ 151.7, 140.3, 129.1, 128.8, 128.7, 127.1, 126.3, 126.2, 125.9, 123.2, 122.7, 117.4, 77.4.

(S)-6-chloro-2-phenyl-2H-chromene (1ae')

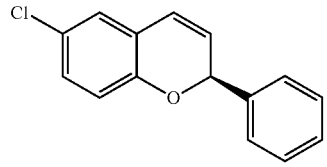 [SMILES: Clc1ccc2c(c1)C=C[C@@H](c1ccccc1)O2]

Yellow solid, 42% yield; $[\alpha]^{20}_D$=−87 (c=0.60, CHCl$_3$); ee was determined to be 96% by HPLC analysis with a Chiralcel OJ-H column (hexane/2-propanol 95:5, 1.0 mL/min, 230 nm); $t_r$ (minor)=15.29 min, $t_r$ (major)=17.06 min.

(R)-6-chloro-7-methyl-2-phenyl-2H-chromene (1af)

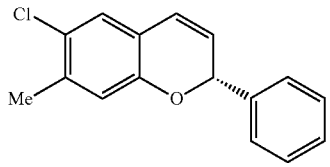

White solid, 40% yield; $[\alpha]^{20}_D$=+140 (c=0.32, CHCl$_3$); ee was determined to be 99% by HPLC analysis with a Chiralcel OD-H column (hexane/2-propanol 98:2, 0.5 mL/min, 230 nm); $t_r$ (major)=10.86 min, $t_r$ (minor)=12.00 min; $^1$H NMR (500 MHz, CDCl$_3$): δ 7.45-7.43 (m, 2H), 7.40-7.35 (m, 3H), 7.00 (s, 1H), 6.68 (s, 1H), 6.49 (d, J=9.4 Hz, 1H), 5.89 (s, 1H), 5.83 (dd, J=9.6, 3.2 Hz, 1H), 2.29 (s, 3H). $^{13}$C NMR (125 MHz, CDCl$_3$): δ 151.5, 140.4, 137.1, 128.7, 128.5, 127.1, 126.4, 126.0, 125.0, 123.0, 120.5, 118.4, 77.2, 20.2.

(R)-6,8-dichloro-2-phenyl-2H-chromene (1ag)

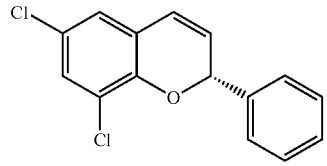 [SMILES: Clc1cc(Cl)c2c(c1)C=C[C@H](c1ccccc1)O2]

White solid, 41% yield; $[\alpha]^{20}_D$=+304 (c=0.5, CHCl$_3$); ee was determined to be 94% by HPLC analysis with a Chiralcel OD-H column (hexane/2-propanol 98:2, 0.5 mL/min, 230 nm); $t_r$ (minor)=12.11 min, $t_r$ (major)=13.48 min; $^1$H NMR (500 MHz, CDCl$_3$): δ 7.45-7.43 (m, 2H), 7.41-7.34 (m, 3H), 7.19 (m, 1H), 6.91 (d, J=2.4 Hz, 1H), 6.48 (dd, J=9.9, 1.7 Hz, 1H), 6.05 (m, 1H), 5.98 (dd, J=9.9, 3.8 Hz, 1H). $^{13}$C NMR (125 MHz, CDCl$_3$): δ 147.6, 139.8, 129.3, 128.8, 128.7, 126.7, 125.7, 124.8, 123.6, 122.7, 121.8, 77.4. HRMS (ESI) m/z: calcd for C$_{15}$H$_9$Cl$_2$O [M−H]$^−$ 275.0030, found 275.0028 calcd for C$_{15}$H$_9{}^{37}$Cl$_2$O [M−H]$^−$ 277.0001, found 276.9996.

(S)-6,8-dichloro-2-phenyl-2H-chromene (3ag')

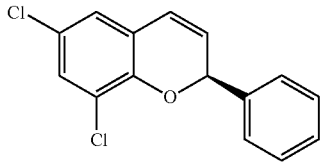 [SMILES: Clc1cc(Cl)c2c(c1)C=C[C@@H](c1ccccc1)O2]

White solid, 45% yield; $[\alpha]^{20}_D = -272$ (c=0.4, CHCl$_3$); ee was determined to be 96% by HPLC analysis with a Chiralcel OD-H column (hexane/2-propanol 98:2, 0.5 mL/min, 230 nm); $t_r$ (major)=11.22 min, $t_r$ (minor)=12.46 min.

(R)-6-chloro-2-(4-chlorophenyl)-2H-chromene (1ah)

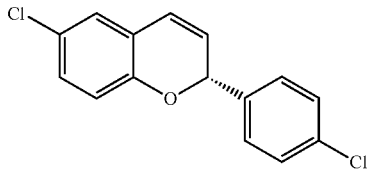 [SMILES: Clc1ccc([C@H]2C=Cc3cc(Cl)ccc3O2)cc1]

Colorless oil, 43% yield; $[\alpha]^{20}_D = +244$ (c=0.8, CH$_2$Cl$_2$); ee was determined to be 99% by HPLC analysis with a Chiralcel OJ-H column (hexane/2-propanol 70:30, 1.0 mL/min, 230 nm); $t_r$ (major)=7.47 min, $t_r$ (minor)=9.92 min; $^1$H NMR (400 MHz, CDCl$_3$): δ 7.38-7.33 (m, 4H), 7.06 (dd, J=8.6, 1.4 Hz, 1H), 6.99 (d, J=2.5 Hz, 1H), 6.70 (d, J=8.6 Hz, 1H), 6.50 (dd, J=9.8, 1.5 Hz, 1H), 5.88 (m, 1H), 5.83 (dd, J=9.8, 3.5 Hz, 1H); $^{13}$C NMR (100 MHz, CDCl$_3$): δ 151.4, 138.6, 134.5, 129.2, 128.9, 128.5, 126.3, 126.1, 125.5, 123.5, 122.5, 117.4, 76.4.

(R)-2-(3,4-difluorophenyl)-5,7-difluoro-2H-chromene (1ai)

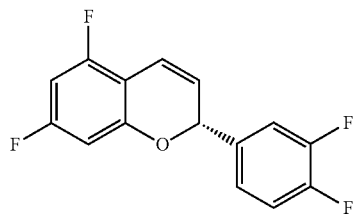 [SMILES: Fc1cc(F)c2c(c1)O[C@@H](c1ccc(F)c(F)c1)C=C2]

Yellow oil, 42% yield; $[\alpha]^{20}_D = -7.6$ (c=0.5, CHCl$_3$); ee was determined to be 96% by HPLC analysis with a Chiralcel AD-H column (hexane/2-propanol 99:1, 0.5 mL/min, 230 nm); $t_r$ (major)=9.16 min, $t_r$ (minor)=9.56 min; $^1$H NMR (500 MHz, CDCl$_3$): δ 7.29 (m, 1H), 7.21-7.18 (m, 2H), 6.79 (dd, J=10.0, 1.4 Hz, 1H), 6.43-6.37 (m, 2H), 5.90 (m, 1H), 5.79 (dd, J=10.1, 3.6 Hz, 1H). $^{13}$C NMR (125 MHz, CDCl$_3$): δ 164.0 (d, J=15.3 Hz), 162.0 (d, J=15.3 Hz), 159.7 (d, J=14.8 Hz), 157.7 (d, J=15.2 Hz), 154.3 (dd, J=15.0, 9.3 Hz), 151.5 (dd, J=12.5, 4.4 Hz), 149.5 (dd, J=12.6, 4.3 Hz), 136.7 (t, J=4.1 Hz), 123.3 (q, J=3.3 Hz), 122.4 (t, J=1.8 Hz), 117.5 (d, J=17.3 Hz), 117.0 (dd, J=3.8, 1.6 Hz), 116.4 (d, J=17.8 Hz), 106.4 (dd, J=18.5, 3.7 Hz), 100.2 (dd, J=25.3, 3.6 Hz), 86.9 (t, J=25.9 Hz), 76.1. $^{19}$F NMR (376 MHz, CDCl$_3$): δ −108.31-108.33 (m, 1F), −119.71-119.73 (m, 1F), −136.53-136.59 (m, 1F), −137.40-137.46 (m, 1F). HRMS (ESI) m/z: calcd for C$_{15}$H$_7$F$_4$O [M−H]$^-$ 279.0433, found 279.0440; calcd for C$_{15}$H$_7$$^{19}$F$_4$O [M−H]$^+$ 280.0467, found 280.0464.

(2R,3S)-2-phenylchroman-3-ol (3a)

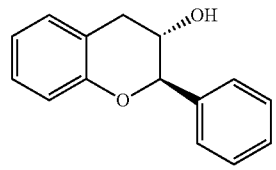 [SMILES: O[C@H]1Cc2ccccc2O[C@@H]1c1ccccc1]

White solid, 45% yield; m.p. 104-105° C.; $[\alpha]^{20}_D = -8$ (c=0.48, CH$_2$Cl$_2$) {$[\alpha]^{20}_D$ 7.9 (c 1.0, CH$_2$Cl$_2$)}[8]; ee was determined to be >99% by HPLC analysis with a Chiralcel AD-H column (hexane/2-propanol 80:20, 0.5 mL/min, 220 nm); $t_r$ (major)=11.66 min; $^1$H NMR (500 MHz, CDCl$_3$): δ 7.46-7.41 (m, 4H), 7.38 (m, 1H), 7.18 (t, J=7.6 Hz, 1H), 7.13 (d, J=7.6 Hz, 1H), 6.96-6.93 (m, 2H), 4.81 (d, J=7.9 Hz, 1H), 4.11 (dd, J=13.8, 8.3 Hz, 1H), 3.09 (dd, J=16.1, 5.3 Hz, 1H), 2.92 (dd, J=16.1, 8.9 Hz, 1H), 1.92 (s, 1H). $^{13}$C NMR (125 MHz, CDCl$_3$): δ 154.1, 138.2, 130.1, 128.8, 128.7, 127.8, 127.2, 121.1, 120.1, 116.5, 81.9, 68.2, 32.8. HRMS (ESI) m/z: calcd for C$_{15}$H$_{13}$O [M−H]$^-$ 225.0921, found 225.0917.

(2R,3S)-2-(p-tolyl)chroman-3-ol (3b)

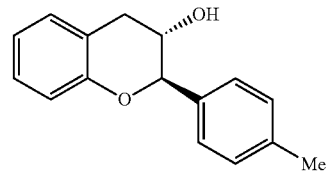 [SMILES: Cc1ccc([C@H]2Oc3ccccc3C[C@@H]2O)cc1]

White solid, 48% yield; m.p. 68-69° C.; $[\alpha]^{20}_D = +3$ (c=0.73, CH$_2$Cl$_2$); ee was determined to be 99% by HPLC analysis with a Chiralcel AD-H column (hexane/2-propanol 85:15, 1.0 mL/min, 220 nm); $t_r$ (major)=7.04 min, $t_r$ (minor)=8.06 min; $^1$H NMR (500 MHz, CDCl$_3$): δ 7.34 (d, J=8.0 Hz, 2H), 7.23 (d, J=7.9 Hz, 2H), 7.16 (t, J=6.6 Hz, 1H), 7.12 (d, J=6.3 Hz, 1H), 6.94-6.92 (m, 2H), 4.77 (d, J=8.0 Hz, 1H), 4.12 (m, 1H), 3.10 (dd, J=16.1, 5.4 Hz, 1H), 2.92 (dd, J=16.1, 9.0 Hz, 1H), 2.38 (s, 3H), 1.82 (s, 1H). $^{13}$C NMR (125 MHz, CDCl$_3$): δ 154.2, 138.6, 135.0, 130.0, 129.6, 127.7, 127.2, 121.0, 120.2, 116.5, 81.8, 68.2, 33.0, 21.2. HRMS (ESI) m/z: calcd for C$_{16}$H$_{15}$O$_2$ [M−H]$^-$ 239.1078, found 239.1075.

(2R,3S)-2-(4-methoxyphenyl)chroman-3-ol (3c)

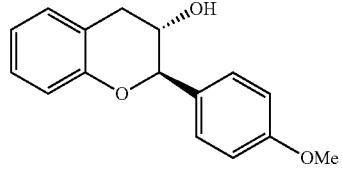 [SMILES: COc1ccc([C@H]2Oc3ccccc3C[C@@H]2O)cc1]

White solid, 42% yield; m.p. 89-90° C.; $[\alpha]^{20}_D$=+8 (c=0.61, CH$_2$Cl$_2$); ee was determined to be >99% by HPLC analysis with a Chiralcel OD-H column (hexane/2-propanol 85:15, 0.5 mL/min, 220 nm); $t_r$ (major)=15.90 min; $^1$H NMR (500 MHz, CDCl$_3$): δ 7.40-7.37 (m, 2H), 7.17-7.11 (m, 2H), 6.97-6.91 (m, 4H), 4.74 (d, J=8.2 Hz, 1H), 4.10 (m, 1H), 3.83 (s, 3H), 3.09 (dd, J=16.1, 5.4 Hz, 1H), 2.93 (dd, J=16.1, 7.1 Hz, 1H), 1.82 (s, 1H). $^{13}$C NMR (125 MHz, CDCl$_3$): δ 160.0, 154.2, 130.0, 129.9, 128.6, 127.7, 121.0, 120.3, 116.5, 114.3, 81.7, 68.2, 55.4, 33.1. HRMS (ESI) m/z: calcd for C$_{16}$H$_{15}$O$_3$[M−H]$^−$ 255.1027, found 255.1026.

(2R,3S)-2-(4-(benzyloxy)phenyl)chroman-3-ol (3d)

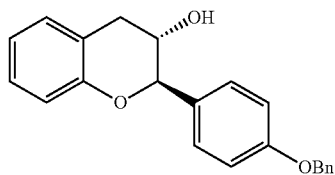 [SMILES: O[C@H]1Cc2ccccc2O[C@@H]1c1ccc(OCc2ccccc2)cc1]

White solid, 42% yield; m.p. 113-114° C.; $[\alpha]^{20}_D$=+10 (c=0.35, CHCl$_3$); ee was determined to be 99% by HPLC analysis with a Chiralcel OD-H column (hexane/2-propanol 80:20, 1.0 mL/min, 220 nm); $t_r$ (minor)=12.71 min, $t_r$ (major)=13.95 min; $^1$H NMR (500 MHz, CDCl$_3$): δ 7.45-7.33 (m, 7H), 7.17-7.12 (m, 2H), 7.05-7.02 (m, 2H), 6.94-6.91 (m, 2H), 5.09 (s, 2H), 4.74 (d, J=8.2 Hz, 1H), 4.11 (m, 1H), 3.12 (dd, J=16.1, 5.4 Hz, 1H), 2.92 (dd, J=16.1, 9.2 Hz, 1H), 1.74 (s, 1H). $^{13}$C NMR (125 MHz, CDCl$_3$): δ 159.2, 154.2, 136.8, 130.2, 130.0, 128.7, 128.6, 128.1, 127.7, 127.5, 121.0, 120.3, 116.5, 115.2, 81.7, 70.1, 68.2, 33.1. HRMS (ESI) m/z: calcd for C$_{22}$H$_{20}$NaO$_3$ [M+Na]$^+$ 355.1305, found 355.1301.

(2R,3S)-2-(4-(methoxymethoxy)phenyl)chroman-3-ol (3e)

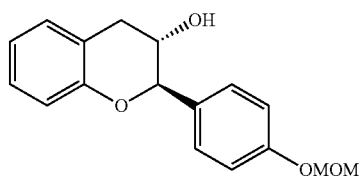

White solid, 45% yield; m.p. 97-98° C.; $[\alpha]^{20}_D$=−4 (c=0.28, CHCl$_3$); ee was determined to be 99% by HPLC analysis with a Chiralcel OD-H column (hexane/2-propanol 90:10, 1.0 mL/min, 220 nm); $t_r$ (minor)=8.19 min, $t_r$ (major)=9.19 min; $^1$H NMR (500 MHz, CDCl$_3$): δ 7.38 (d, J=8.7 Hz, 2H), 7.16-7.08 (m, 4H), 6.92 (t, J=7.6 Hz, 2H), 5.19 (s, 2H), 4.74 (d, J=8.2 Hz, 1H), 4.10 (m, 1H), 3.48 (s, 3H), 3.11 (dd, J=16.1, 5.4 Hz, 1H), 2.92 (dd, J=16.1, 9.2 Hz, 1H), 1.84 (s, 1H). $^{13}$C NMR (125 MHz, CDCl$_3$): δ 157.6, 154.1, 131.3, 130.0, 128.6, 127.7, 121.0, 120.2, 116.6, 116.5, 94.3, 81.6, 68.1, 56.1, 33.1. HRMS (ESI) m/z: calcd for C$_{17}$H$_{18}$NaO$_4$ [M+Na]$^+$ 309.1097, found 309.1094.

(2R,3S)-2-(4-fluorophenyl)chroman-3-ol (3f)

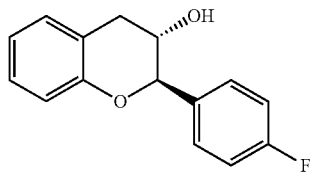 [SMILES: O[C@H]1Cc2ccccc2O[C@@H]1c1ccc(F)cc1]

White solid, 47% yield; m.p. 99-100° C.; $[\alpha]^{20}_D$=−11 (c=0.58, CH$_2$Cl$_2$); ee was determined to be 99% by HPLC analysis with a Chiralcel AD-H column (hexane/2-propanol 90:10, 1.0 mL/min, 220 nm); $t_r$ (major)=8.21 min, $t_r$ (minor)=9.76 min; $^1$H NMR (500 MHz, CDCl$_3$): δ 7.45-7.41 (m, 2H), 7.17 (t, J=7.5 Hz, 1H), 7.13-7.09 (m, 3H), 6.96-6.93 (m, 2H), 4.79 (d, J=8.0 Hz, 1H), 4.08 (m, 1H), 3.09 (dd, J=16.1, 5.4 Hz, 1H), 2.92 (dd, J=16.1, 9.0 Hz, 1H), 1.87 (s, 1H). $^{13}$C NMR (125 MHz, CDCl$_3$): δ 162.9 (d, J=245.9 Hz), 153.9, 134.0 (d, J=2.8 Hz), 130.0, 128.9 (d, J=8.1 Hz), 127.8, 121.2, 120.0, 116.5, 115.9, 118.7, 81.3, 68.2, 33.0. HRMS (ESI) m/z: calcd for C$_{15}$H$_{12}$FO$_2$ [M−H]$^−$ 243.0827, found 243.0825; calcd for C$_{15}$H$_{12}$$^{19}$FO$_2$ [M−H]$^−$ 244.0855, found 244.0858. $^{19}$F NMR (376 MHz, CDCl$_3$): δ −113.08.

(2R,3S)-2-(4-chlorophenyl)chroman-3-ol (3g)

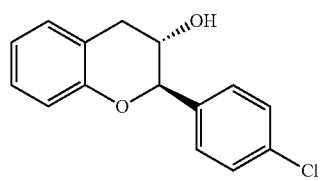 [SMILES: O[C@H]1Cc2ccccc2O[C@@H]1c1ccc(Cl)cc1]

White solid, 41% yield; m.p. 109-110° C.; $[\alpha]^{20}_D$=+12 (c=0.48, CH$_2$Cl$_2$); ee was determined to be >99% by HPLC analysis with a Chiralcel AD-H column (hexane/2-propanol 85:15, 1.0 mL/min, 220 nm); $t_r$ (major)=6.74 min; $^1$H NMR (500 MHz, CDCl$_3$): δ 7.39 (s, 4H), 7.17 (t, J=7.8 Hz, 1H), 7.12 (m, 1H), 6.94 (t, J=7.7 Hz, 2H), 4.81 (d, J=7.8 Hz, 1H), 4.09 (m, 1H), 3.08 (dd, J=16.2, 5.3 Hz, 1H), 2.92 (dd, J=16.1, 8.8 Hz, 1H), 1.81 (s, 1H). $^{13}$C NMR (125 MHz, CDCl$_3$): δ 153.8, 136.8, 134.5, 130.0, 129.0, 128.5, 127.9, 121.3, 119.9, 116.5, 81.2, 68.2, 32.9. HRMS (ESI) m/z: calcd for C$_{15}$H$_{12}$ClO$_2$ [M−H]$^−$ 259.0531, found 259.0529; calcd for C$_{15}$H$_{12}$$^{37}$ClO$_2$ [M−H]$^−$ 261.0496, found 261.0496.

(2R,3S)-2-(4-bromophenyl)chroman-3-ol (3h)

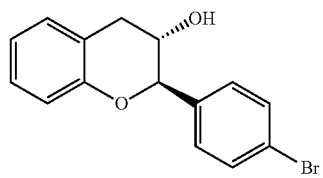 [SMILES: O[C@H]1Cc2ccccc2O[C@@H]1c1ccc(Br)cc1]

White solid, 42% yield; m.p. 109-110° C.; $[\alpha]^{20}_D$=−11 (c=0.82, CH$_2$Cl$_2$); ee was determined to be >99% by HPLC analysis with a Chiralcel AD-H column (hexane/2-propanol 85:15, 1.0 mL/min, 220 nm); $t_r$ (major)=6.74 min; $^1$H NMR (500 MHz, CDCl$_3$): δ 7.56-7.53 (m, 2H), 7.33-7.32 (m, 2H), 7.17 (m, 1H), 7.11 (m, 1H), 6.95-6.92 (m, 2H), 4.79 (d, J=7.8 Hz, 1H), 4.09 (m, 1H), 3.07 (dd, J=16.1, 5.3 Hz, 1H), 2.92 (dd, J=16.1, 8.8 Hz, 1H), 1.80 (s, 1H). 13C NMR (125 MHz, CDCl$_3$): δ 153.7, 137.3, 131.9, 130.0, 128.8, 127.9, 122.6, 121.3, 119.9, 116.5, 81.2, 68.1, 32.9. HRMS (ESI) m/z: calcd for C$_{15}$H$_{12}$BrO$_2$ [M−H]$^-$ 303.0026, found 303.0027; calcd for C$_{15}$H$_{12}$$^{81}$BrO$_2$ [M−H]$^-$ 305.0000, found 3305.0007.

(2R,3S)-2-(4-(trifluoromethyl)phenyl)chroman-3-ol (3i)

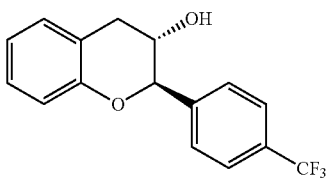 [SMILES: O[C@H]1Cc2ccccc2O[C@@H]1c1ccc(C(F)(F)F)cc1]

White solid, 35% yield; m.p. 114-115° C.; [α]$^{20}_D$=−27 (c=0.71, CH$_2$Cl$_2$); ee was determined to be 99.8% by HPLC analysis with a Chiralcel AD-H column (hexane/2-propanol 85:15, 1.0 mL/min, 220 nm); $t_r$ (major)=5.36 min, $t_r$ (minor)=6.38 min; $^1$H NMR (500 MHz, CDCl$_3$): δ 7.68 (d, J=8.2 Hz, 2H), 7.57 (d, J=8.3 Hz, 2H), 7.19 (m, 1H), 7.13 (m, 1H), 6.97-6.95 (m, 2H), 4.91 (d, J=7.6 Hz, 1H), 4.13 (m, 1H), 3.06 (dd, J=16.2, 5.2 Hz, 1H), 2.92 (dd, J=16.2, 8.5 Hz, 1H), 1.96 (s, 1H). $^{13}$C NMR (125 MHz, CDCl$_3$): δ 153.6, 142.3, 130.7 (q, J=32.4, Hz), 130.1, 128.0, 127.4, 125.7 (q, J=3.69 Hz), 124.0 (q, J=270.6 Hz), 121.4, 119.8, 116.5, 81.1, 68.1, 32.8. HRMS (ESI) m/z: calcd for C$_{16}$H$_{12}$F$_3$O$_2$ [M−H]$^-$ 293.0789, found 293.0796; calcd for C$_{16}$H$_{12}$$^{19}$F$_3$O$_2$ [M−H1]$^-$ 294.0823, found 294.0829. $^{19}$F NMR (376 MHz, CDCl$_3$): δ −62.57.

(2R,3S)-2-(o-tolyl)chroman-3-ol (3j)

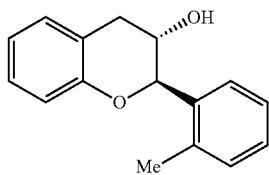 [SMILES: Cc1ccccc1[C@H]1Oc2ccccc2C[C@@H]1O]

White solid, 45% yield; m.p. 91-92° C.; [α]$^{20}_D$=+29 (c=0.59, CH$_2$Cl$_2$); ee was determined to be >99% by HPLC analysis with a Chiralcel AD-H column (hexane/2-propanol 85:15, 1.0 mL/min, 220 nm); $t_r$ (major)=5.49 min; $^1$H NMR (500 MHz, CDCl$_3$): δ 7.44 (m, 1H), 7.27-7.23 (m, 2H), 7.21 (m, 1H), 7.16-7.12 (m, 2H), 6.94-6.89 (m, 2H), 5.06 (d, J=8.3 Hz, 1H), 4.16 (m, 1H), 3.12 (dd, J=16.1, 5.4 Hz, 1H), 2.95 (dd, J=16.0, 9.3 Hz, 1H), 2.43 (s, 3H), 1.82 (d, J=3.4 Hz, 1H). $^{13}$C NMR (125 MHz, CDCl$_3$): δ 154.4, 137.0, 136.3, 130.7, 130.0, 128.5, 127.7, 126.7, 126.6, 121.0, 120.3, 116.5, 78.5, 68.3, 33.4, 19.7. HRMS (ESI) m/z: calcd for C$_{16}$H$_{15}$O$_2$ [M−H]$^-$ 239.1078, found 239.1076.

(2R,3S)-2-(m-tolyl)chroman-3-ol (3k)

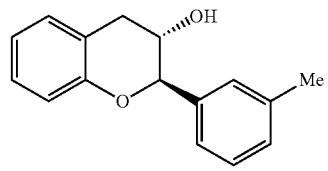 [SMILES: Cc1cccc([C@H]2Oc3ccccc3C[C@@H]2O)c1]

White solid, 43% yield; m.p. 88-89° C.; [α]$^{20}_D$=−3 (c=0.59, CH$_2$Cl$_2$); ee was determined to be 99% by HPLC analysis with a Chiralcel AD-H column (hexane/2-propanol 85:15, 1.0 mL/min, 220 nm); $t_r$ (major)=6.16 min, $t_r$ (minor)=7.08 min; $^1$H NMR (500 MHz, CDCl$_3$): δ 7.31 (t, J=7.6 Hz, 1H), 7.28-7.24 (m, 2H), 7.20-7.12 (m, 3H), 6.95-6.92 (m, 2H), 4.75 (d, J=8.1 Hz, 1H), 4.12 (m, 1H), 3.11 (dd, J=16.1, 5.4 Hz, 1H), 2.93 (dd, J=16.1, 9.2 Hz, 1H), 2.39 (s, 3H), 1.84 (s, 1H). $^{13}$C NMR (125 MHz, CDCl$_3$): δ 154.1, 138.6, 137.9, 130.0, 129.6, 128.8, 127.9, 127.7, 124.4, 121.1, 120.2, 116.5, 82.1, 68.2, 33.0, 21.5. HRMS (ESI) m/z: calcd for C$_{16}$H$_{15}$O$_2$[M−H]$^-$ 239.1078, found 239.1075.

(2R,3S)-2-(3,5-dimethylphenyl)chroman-3-ol (3l)

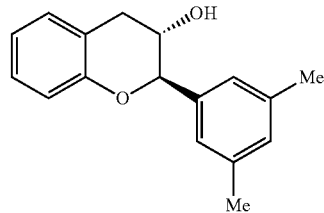 [SMILES: Cc1cc(C)cc([C@H]2Oc3ccccc3C[C@@H]2O)c1]

White solid, 48% yield; m.p. 135-136° C.; [α]$^{20}_D$=−9 (c=0.33, CH$_3$Cl$_3$); ee was determined to be >99% by HPLC analysis with a Chiralcel AD-H column (hexane/2-propanol 85:15, 1.0 mL/min, 220 nm); $t_r$ (major)=5.47 min; $^1$H NMR (500 MHz, CDCl$_3$): δ 7.17-7.13 (m, 2H), 7.08 (s, 2H), 7.02 (s, 1H), 6.95-6.92 (m, 2H), 4.69 (d, J=8.3 Hz, 1H), 4.12 (m, 1H), 3.13 (dd, J=16.0, 5.4 Hz, 1H), 2.93 (dd, J=16.0, 9.4 Hz, 1H), 2.35 (s, 6H), 1.82 (d, J=3.0 Hz, 1H). $^{13}$C NMR (125 MHz, CDCl$_3$): δ 154.2, 138.5, 137.8, 130.5, 130.0, 127.7, 125.1, 121.0, 120.3, 116.5, 82.2, 68.1, 33.2, 21.4. HRMS (ESI) m/z: calcd for C$_{17}$H$_{17}$O$_2$[M−H]$^-$ 253.1234, found 253.1233.

(2R,3S)-2-(naphthalen-2-yl)chroman-3-ol (3m)

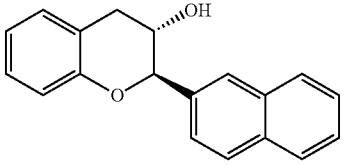 [SMILES: O[C@H]1Cc2ccccc2O[C@@H]1c1ccc2ccccc2c1]

White solid, 40% yield; m.p. 141-142° C.; [α]$^{20}_D$=−12 (c=0.66, CH$_2$Cl$_2$); ee was determined to be 99.5% by HPLC analysis with a Chiralcel AD-H column (hexane/2-propanol 90:10, 1.0 mL/min, 220 nm); $t_r$ (major)=12.29 min, $t_r$ (major)=15.31 min; ¹H NMR (500 MHz, CDCl₃): δ 7.92-7.86 (m, 4H), 7.57-7.52 (m, 3H), 7.20 (d, J=7.6 Hz, 1H), 7.14 (d, J=7.4 Hz, 1H), 7.00-6.95 (m, 2H), 4.96 (d, J=8.0 Hz, 1H), 4.20 (m, 1H), 3.11 (dd, J=16.1, 5.3 Hz, 1H), 2.95 (dd, J=16.1, 9.0 Hz, 1H), 1.90 (s, 1H). ¹³C NMR (125 MHz, CDCl₃): δ 154.1, 135.5, 133.5, 133.2, 130.1, 128.8, 128.1, 127.8, 127.8, 126.9, 126.5, 126.4, 124.3, 121.2, 120.2, 116.6, 82.1, 68.1, 33.0. HRMS (ESI) m/z: calcd for C₁₉H₁₅O₂[M−H]⁻ 275.1078, found 275.1079.

(2S,3R)-2-(naphthalen-2-yl)chroman-3-ol (3m')

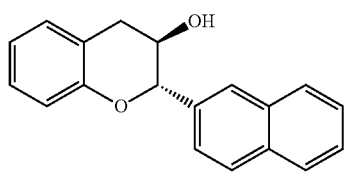 [SMILES: O[C@@H]1Cc2ccccc2O[C@H]1c1ccc2ccccc2c1]

White solid, 48% yield; [α]²⁰_D=+12 (c=0.35, CH₂Cl₂); ee was determined to be >99% by HPLC analysis with a Chiralcel AD-H column (hexane/2-propanol 90:10, 1.0 mL/min, 220 nm); t_r (major)=15.12 min.

(2S,3S)-2-(thiophen-2-yl)chroman-3-ol (3n)

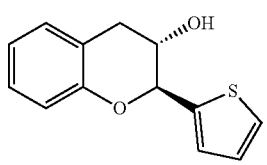 [SMILES: O[C@H]1Cc2ccccc2O[C@@H]1c1cccs1]

White solid, 38% yield; m.p. 94-95° C.; [α]²⁰_D=+20 (c=0.54, CH₂Cl₂); ee was determined to be 98% by HPLC analysis with a Chiralcel AD-H column (hexane/2-propanol 85:15, 1.0 mL/min, 220 nm); t_r (major)=7.41 min, t_r (major)=8.79 min; ¹H NMR (500 MHz, CDCl₃): δ 7.38 (m, 1H), 7.18-7.11 (m, 3H), 7.05 (m, 1H), 6.96-6.93 (m, 2H), 5.08 (d, J=8.0 Hz, 1H), 4.13 (m, 1H), 3.16 (dd, J=16.2, 5.4 Hz, 1H), 2.93 (dd, J=16.2, 8.9 Hz, 1H), 2.08 (s, 1H). ¹³C NMR (125 MHz, CDCl₃): δ 153.6, 141.0, 130.0, 127.8, 127.0, 126.6, 126.3, 121.4, 120.0, 116.7, 78.2, 68.5, 32.8. HRMS (ESI) m/z: calcd for C₁₃H₁₁SO₂ [M−H]⁻ 231.0485, found 231.0482.

(2S,3S)-2-(furan-2-yl)chroman-3-ol (3o)

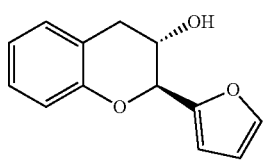 [SMILES: O[C@H]1Cc2ccccc2O[C@@H]1c1ccco1]

White solid, 38% yield; m.p. 80-81° C.; [α]²⁰_D=+76 (c=0.63, CH₂Cl₂); ee was determined to be 98% by HPLC analysis with a Chiralcel AD-H column (hexane/2-propanol 85:15, 1.0 mL/min, 220 nm); t_r (major)=7.41 min, t_r (minor)=8.79 min; ¹H NMR (500 MHz, CDCl₃): δ 7.47 (m, 1H), 7.15-7.09 (m, 2H), 6.94-6.89 (m, 2H), 6.47 (d, J=3.3 Hz, 1H), 6.42 (m, 1H), 4.92 (d, J=7.8 Hz, 1H), 4.43 (m, 1H), 3.16 (dd, J=16.2, 5.4 Hz, 1H), 2.90 (dd, J=16.2, 8.5 Hz, 1H), 2.07 (s, 1H). ¹³C NMR (125 MHz, CDCl₃): δ 153.3, 150.9, 143.2, 130.0, 127.8, 121.3, 119.7, 116.6, 110.7, 109.9, 75.3, 65.6, 32.8. HRMS (ESI) m/z: calcd for C₁₃H₁₁O₃ [M−H]⁻ 215.0714, found 215.0709.

(2R,3R)-2-(furan-2-yl)chroman-3-ol (3o')

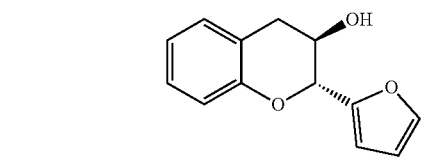 [SMILES: O[C@@H]1Cc2ccccc2O[C@H]1c1ccco1]

White solid, 35% yield; [α]²⁰_D=−64 (c=0.50, CH₂Cl₂); ee was determined to be 99% by HPLC analysis with a Chiralcel OD-H column (hexane/2-propanol 90:10, 1.0 mL/min, 220 nm); t_r (major)=8.16 min, t_r (minor)=8.76 min.

(2R,3S)-2-propylchroman-3-ol (3p)

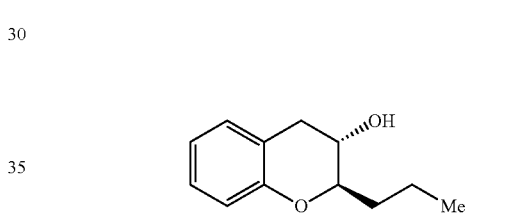

Colorless oil, 34% yield; [α]²⁰_D=−8 (c=0.21, CHCl₃); ee was determined to be >99% by HPLC analysis with a Chiralcel OJ-H column (hexane/2-propanol 95:5, 1.0 mL/min, 220 nm); t_r (major)=6.97 min; ¹H NMR (400 MHz, CDCl₃): δ 7.14 (m, 1H), 7.08 (d, J=7.4 Hz, 1H), 6.92-6.85 (m, 2H), 4.03-3.95 (m, 2H), 3.08 (dd, J=15.1, 4.9 Hz, 1H), 2.80 (dd, J=16.5, 6.0 Hz, 1H), 2.00 (s, 1H), 1.68-1.62 (m, 3H), 1.51 (m, 1H), 0.99 (t, J=7.2 Hz, 3H). ¹³C NMR (125 MHz, CDCl₃): δ 153.1, 130.1, 127.7, 120.7, 119.5, 116.9, 78.9, 66.5, 33.5, 32.1, 14.0. HRMS (ESI) m/z: calcd for C₁₂H₁₅O₂[M−H]⁻ 191.1078, found 191.1072.

(2S,3R)-2-propylchroman-3-ol (3p')

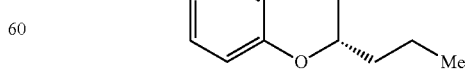

Colorless oil, 45% yield; [α]²⁰_D=−61 (c=0.44, CHCl₃); ee was determined to be 99% by HPLC analysis with a Chiralcel OJ-H column (hexane/2-propanol 95:5, 1.0 mL/min, 220 nm); t_r (minor)=12.98 min, t_r (major)=13.87 min.

(2R,3S)-5-methyl-2-phenylchroman-3-ol (3q)

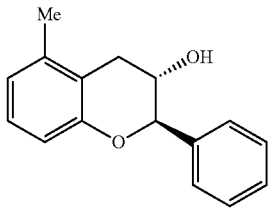 [SMILES: Cc1cccc2c1C[C@H](O)[C@@H](c1ccccc1)O2]

White solid, 42% yield; m.p. 116-117° C.; $[\alpha]^{20}_D = -27$ (c=0.50, CHCl$_3$); ee was determined to be 98% by HPLC analysis with a Chiralcel OD-H column (hexane/2-propanol 95:5, 1.0 mL/min, 220 nm); t$_r$ (major)=9.23 min, t$_r$ (minor)=9.86 min; $^1$H NMR (500 MHz, CDCl$_3$): δ 7.48-7.41 (m, 4H), 7.38 (m, 1H), 7.09 (t, J=7.8 Hz, 1H), 6.84-6.82 (m, 2H), 4.73 (d, J=8.2 Hz, 1H), 4.13 (m, 1H), 3.04 (dd, J=16.4, 5.7 Hz, 1H), 2.74 (dd, J=16.4, 8.9 Hz, 1H), 2.27 (s, 3H), 1.88 (s, 1H). $^{13}$C NMR (125 MHz, CDCl$_3$): δ 154.2, 138.1, 137.9, 128.8, 128.7, 127.3, 127.1, 122.5, 119.3, 114.3, 81.3, 68.6, 31.1, 19.2. HRMS (ESI) m/z: calcd for C$_{16}$H$_{17}$O$_2$[M+H]$^+$ 241.1223, found 241.1221.

(2R,3S)-6-methyl-2-phenylchroman-3-ol (3r)

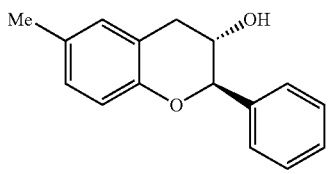 [SMILES: Cc1ccc2c(c1)C[C@H](O)[C@@H](c1ccccc1)O2]

White solid, 47% yield; m.p. 109-110° C.; $[\alpha]^{20}_D = -4$ (c=0.52, CH$_2$Cl$_2$); ee was determined to be 99% by HPLC analysis with a Chiralcel OJ-H column (hexane/2-propanol 85:15, 1.0 mL/min, 220 nm); t$_r$ (major)=12.94 min, t$_r$ (minor)=15.08 min; $^1$H NMR (500 MHz, CDCl$_3$): δ 7.46-7.40 (m, 4H), 7.38 (m, 1H), 6.97 (m, 1H), 6.93 (s, 1H), 6.84 (d, J=8.3 Hz, 1H), 4.79 (d, J=7.8 Hz, 1H), 4.11 (m, 1H), 3.05 (dd, J=16.1, 5.3 Hz, 1H), 2.88 (dd, J=16.1, 8.8 Hz, 1H), 2.29 (s, 3H), 1.84 (s, 1H). $^{13}$C NMR (125 MHz, CDCl$_3$): δ 151.8, 138.3, 130.3, 128.8, 128.7, 128.4, 127.1, 119.8, 116.2, 81.9, 68.3, 32.8, 20.5. HRMS (ESI) m/z: calcd for C$_{16}$H$_{15}$O$_2$[M−H]$^-$ 239.1078, found 239.1075.

(2R,3S)-7-methyl-2-phenylchroman-3-ol (3s)

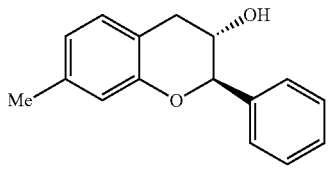 [SMILES: Cc1ccc2c(c1)O[C@H](c1ccccc1)[C@@H](O)C2]

White solid, 43% yield; m.p. 95-96° C.; $[\alpha]^{20}_D = -25$ (c=0.72, CH$_2$Cl$_2$); ee was determined to be 98% by HPLC analysis with a Chiralcel AD-H column (hexane/2-propanol 90:10, 1.0 mL/min, 220 nm); t$_r$ (major)=7.63 min, t$_r$ (minor)=9.61 min; $^1$H NMR (500 MHz, CDCl$_3$): δ 7.45-7.40 (m, 4H), 7.37 (m, 1H), 7.00 (d, J=7.6 Hz, 1H), 6.77-6.76 (m, 2H), 4.81 (d, J=7.8 Hz, 1H), 4.11 (m, 1H), 3.05 (dd, J=15.9, 5.3 Hz, 1H), 2.87 (dd, J=16.0, 8.8 Hz, 1H), 2.32 (s, 3H), 1.82 (s, 1H). $^{13}$C NMR (125 MHz, CDCl$_3$): δ 153.8, 138.3, 137.8, 129.8, 128.8, 128.7, 127.1, 122.0, 116.9, 81.8, 68.4, 32.4, 21.1. HRMS (ESI) m/z: calcd for C$_{16}$H$_{15}$O$_2$ [M−H]$^-$ 239.1078, found 239.1074.

(2R,3S)-8-methyl-2-phenylchroman-3-ol (3t)

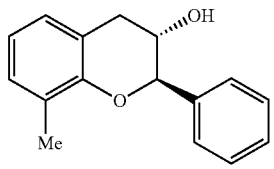 [SMILES: Cc1cccc2c1O[C@H](c1ccccc1)[C@@H](O)C2]

White solid, 46% yield; m.p. 68-69° C.; $[\alpha]^{20}_D = -46$ (c=0.35, CHCl$_3$); ee was determined to be >99% by HPLC analysis with a Chiralcel AS-H column (hexane/2-propanol 99:1, 1.0 mL/min, 220 nm); t$_r$ (major)=15.61 min; $^1$H NMR (500 MHz, CDCl$_3$): δ 7.46-7.40 (m, 4H), 7.37 (m, 1H), 7.04 (d, J=7.3 Hz, 1H), 6.96 (d, J=7.5 Hz, 1H), 6.84 (t, J=7.4 Hz, 1H), 4.87 (d, J=7.6 Hz, 1H), 4.09 (m, 1H), 3.06 (dd, J=16.1, 5.2 Hz, 1H), 2.92 (dd, J=16.1, 8.6 Hz, 1H), 2.24 (s, 3H), 1.80 (s, 1H). $^{13}$C NMR (125 MHz, CDCl$_3$): δ 152.1, 138.6, 128.9, 128.7, 128.5, 127.6, 126.9, 125.8, 120.5, 119.4, 81.7, 68.4, 32.8, 16.2. HRMS (ESI) m/z: calcd for C$_{16}$H$_{17}$O$_2$[M+H]$^+$ 241.1223, found 241.1220.

(2R,3S)-5,7-dimethyl-2-phenylchroman-3-ol (3u)

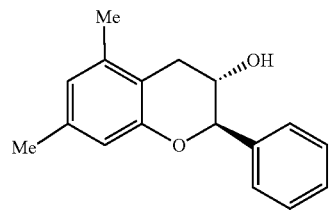 [SMILES: Cc1cc(C)c2c(c1)O[C@H](c1ccccc1)[C@@H](O)C2]

White solid, 43% yield; m.p. 149-150° C.; $[\alpha]^{20}_D = -21$ (c=0.16, CHCl$_3$); ee was determined to be >99% by HPLC analysis with a Chiralcel AS-H column (hexane/2-propanol 98:2, 0.5 mL/min, 220 nm); t$_r$ (major)=24.60 min; $^1$H NMR (500 MHz, CDCl$_3$): δ 7.46-7.41 (m, 4H), 7.38 (m, 1H), 6.66 (s, 1H), 6.65 (s, 1H), 4.73 (d, J=8.2 Hz, 1H), 4.12 (m, 1H), 3.00 (dd, J=16.2, 5.6 Hz, 1H), 2.70 (dd, J=16.2, 8.8 Hz, 1H), 2.28 (s, 3H), 2.22 (s, 3H), 1.80 (s, 1H). $^{13}$C NMR (125 MHz, CDCl$_3$): δ 154.0, 138.2, 137.6, 137.1, 128.8, 128.7, 127.2, 123.6, 116.0, 114.7, 81.3, 68.7, 30.7, 21.0, 19.1. HRMS (ESI) m/z: calcd for C$_{17}$H$_{19}$O$_2$[M+H]+ 255.1380, found 255.1377.

(2R,3S)-6,7-dimethyl-2-phenylchroman-3-ol (3v)

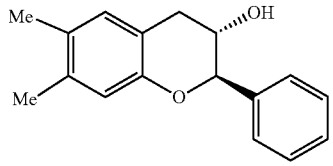 [SMILES: Cc1cc2c(cc1C)O[C@H](c1ccccc1)[C@@H](O)C2]

White solid, 45% yield; m.p. 151-152° C.; $[\alpha]^{20}_D = -24$ (c=0.33, CHCl$_3$); ee was determined to be >99% by HPLC analysis with a Chiralcel AD-H column (hexane/2-propanol 95:5, 1.0 mL/min, 210 nm); $t_r$ (major)=11.91 min; $^1$H NMR (500 MHz, CDCl$_3$): δ 7.45-7.40 (m, 4H), 7.37 (m, 1H), 6.88 (s, 1H), 6.76 (s, 1H), 4.79 (d, J=7.7 Hz, 1H), 4.10 (m, 1H), 3.01 (dd, J=15.9, 5.2 Hz, 1H), 2.85 (dd, J=15.9, 8.6 Hz, 1H), 2.23 (s, 3H), 2.21 (s, 3H), 1.84 (s, 1H). $^{13}$C NMR (125 MHz, CDCl$_3$): δ 151.9, 138.4, 136.2, 130.7, 129.2, 128.8, 128.6, 127.1, 117.3, 116.9, 81.8, 68.5, 32.3, 19.6, 18.8. HRMS (ESI) m/z: calcd for C$_{17}$H$_{19}$O$_2$[M+H]+ 255.1380, found 255.1376.

(2R,3S)-5-methoxy-2-phenylchroman-3-ol (3w)

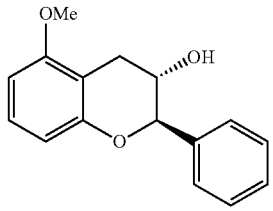 [SMILES: COc1cccc2c1C[C@H](O)[C@@H](c1ccccc1)O2]

White solid, 41% yield; m.p. 116-117° C.; $[\alpha]^{20}_D = -3$ (c=0.32, CHCl$_3$); ee was determined to be >99% by HPLC analysis with a Chiralcel OD-H column (hexane/2-propanol 95:5, 1.0 mL/min, 220 nm); $t_r$ (major)=11.08 min; $^1$H NMR (500 MHz, CDCl$_3$): δ 7.45-7.39 (m, 4H), 7.37 (m, 1H), 7.13 (t, J=8.2 Hz, 1H), 6.61 (d, J=8.2 Hz, 1H), 6.49 (d, J=8.2 Hz, 1H), 4.77 (d, J=7.9 Hz, 1H), 4.10 (m, 1H), 3.84 (s, 3H), 3.08 (dd, J=16.9, 7.1 Hz, 1H), 2.69 (dd, J=16.9, 8.6 Hz, 1H), 1.85 (s, 1H). $^{13}$C NMR (125 MHz, CDCl$_3$): δ 158.2, 154.8, 138.2, 128.8, 128.6, 127.5, 127.2, 109.3, 109.2, 102.5, 81.4, 68.1, 55.5, 27.7. HRMS (ESI) m/z: calcd for C$_{16}$H$_{17}$O$_3$[M+H]$^+$ 257.1172, found 257.1169.

(2R,3S)-6-methoxy-2-phenylchroman-3-ol (3x)

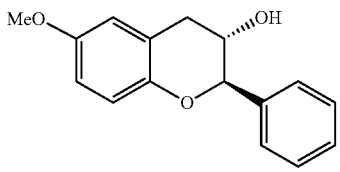 [SMILES: COc1ccc2c(c1)C[C@H](O)[C@@H](c1ccccc1)O2]

White solid, 45% yield; m.p. 118-119° C.; $[\alpha]^{20}_D = -4$ (c=0.52, CH$_2$Cl$_2$); ee was determined to be >99% by HPLC analysis with a Chiralcel OJ-H column (hexane/2-propanol 95:5, 1.0 mL/min, 220 nm); $t_r$ (major)=11.94 min; $^1$H NMR (500 MHz, CDCl$_3$): δ 7.45-7.40 (m, 4H), 7.36 (m, 1H), 6.87 (d, J=8.9 Hz, 1H), 6.74 (dd, J=8.9, 3.0 Hz, 1H), 6.65 (d, J=3.0 Hz, 1H), 4.76 (d, J=7.9 Hz, 1H), 4.11 (m, 1H), 3.77 (s, 3H), 3.05 (dd, J=16.3, 5.4 Hz, 1H), 2.89 (dd, J=16.2, 8.7 Hz, 1H), 1.90 (s, 1H). $^{13}$C NMR (125 MHz, CDCl$_3$): δ 153.9, 148.1, 138.3, 128.8, 128.7, 127.2, 120.8, 117.2, 114.2, 113.9, 81.8, 68.2, 55.8, 33.1. HRMS (ESI) m/z: calcd for C$_{16}$H$_{15}$O$_3$ [M−H]$^-$ 255.1027, found 255.1026.

(2R,3S)-7-methoxy-2-phenylchroman-3-ol (3y)

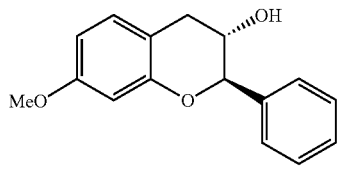 [SMILES: COc1ccc2c(c1)O[C@H](c1ccccc1)[C@@H](O)C2]

White solid, 39% yield; m.p. 158-159° C.; $[\alpha]^{20}_D = -35$ (c=0.24, CHCl$_3$); ee was determined to be >99% by HPLC analysis with a Chiralcel AD-H column (hexane/2-propanol 90:10, 1.0 mL/min, 220 nm); $t_r$ (major)=11.55 min; $^1$H NMR (500 MHz, CDCl$_3$): δ 7.45-7.40 (m, 4H), 7.38 (m, 1H), 7.00 (d, J=8.3 Hz, 1H), 6.54-6.50 (m, 2H), 4.82 (d, J=7.8 Hz, 1H), 4.13 (m, 1H), 3.77 (s, 3H), 3.02 (dd, J=15.8, 5.3 Hz, 1H), 2.85 (dd, J=15.7, 8.7 Hz, 1H), 1.75 (s, 1H). $^{13}$C NMR (125 MHz, CDCl$_3$): δ 159.4, 154.7, 138.1, 130.5, 128.9, 128.7, 127.1, 111.9, 108.2, 101.2, 81.9, 68.4, 55.4, 32.1. HRMS (ESI) m/z: calcd for C$_{16}$H$_{17}$O$_3$[M+H]+ 257.1172, found 257.1169.

(2R,3S)-8-methoxy-2-phenylchroman-3-ol (3z)

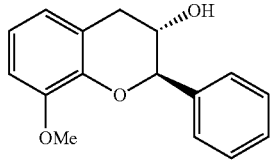 [SMILES: COc1cccc2c1O[C@H](c1ccccc1)[C@@H](O)C2]

White solid, 46% yield; m.p. 151-152° C.; $[\alpha]^{20}_D = -52$ (c=0.42, CHCl$_3$); ee was determined to be >99% by HPLC analysis with a Chiralcel OD-H column (hexane/2-propanol 90:10, 1.0 mL/min, 220 nm); $t_r$ (major)=18.62 min; $^1$H NMR (500 MHz, CDCl$_3$): δ 7.42-7.36 (m, 4H), 7.33 (m, 1H), 6.88 (t, J=7.9 Hz, 1H), 6.78 (d, J=7.9 Hz, 1H), 6.71 (d, J=7.6 Hz, 1H), 4.95 (d, J=7.1 Hz, 1H), 4.15 (m, 1H), 3.86 (s, 3H), 3.03 (dd, J=16.3, 5.1 Hz, 1H), 2.88 (dd, J=16.3, 7.9 Hz, 1H), 1.94 (s, 1H). $^{13}$C NMR (125 MHz, CDCl$_3$): δ 148.3, 143.3, 138.2, 128.8, 128.5, 126.9, 121.8, 120.8, 109.8, 81.8, 68.0, 56.0, 32.1. HRMS (ESI) m/z: calcd for C$_{16}$H$_{17}$O$_3$[M+H]$^+$ 257.1172, found 257.1168.

(2R,3S)-6,7-dimethoxy-2-phenylchroman-3-ol (3aa)

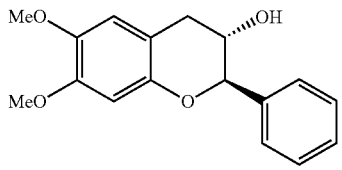 [SMILES: COc1cc2c(cc1OC)O[C@H](c1ccccc1)[C@@H](O)C2]

Yellow oil, 39% yield; $[\alpha]^{20}_D$=−16 (c=0.47, CHCl$_3$); ee was determined to be 97% by HPLC analysis with a Chiralcel OD-H column (hexane/2-propanol 95:5, 1.0 mL/min, 210 nm); t$_r$ (minor)=20.44 min; t$_r$ (major)=21.39 min; $^1$H NMR (500 MHz, CDCl$_3$): δ 7.44-7.40 (m, 4H), 7.36 (m, 1H), 6.58 (s, 1H), 6.52 (s, 1H), 4.76 (d, J=7.8 Hz, 1H), 4.12 (m, 1H), 3.84 (s, 3H), 3.82 (s, 3H), 3.00 (dd, J=15.9, 5.4 Hz, 1H), 2.84 (dd, J=15.9, 8.6 Hz, 1H), 1.82 (s, 1H). $^{13}$C NMR (125 MHz, CDCl$_3$): δ 148.6, 147.8, 143.7, 138.2, 128.8, 128.7, 127.2, 112.3, 110.4, 100.6, 81.9, 68.3, 56.4, 55.9, 32.4. HRMS (ESI) m/z: calcd for C$_{17}$H$_{19}$O$_4$[M+H]+ 287.1278, found 287.1275.

(2R,3S)-6-(methoxymethoxy)-2-phenylchroman-3-ol (3ab)

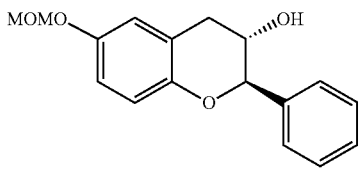

White solid, 48% yield; m.p. 65-66° C.; $[\alpha]^{20}_D$=−6 (c=0.31, CHCl$_3$); ee was determined to be 96% by HPLC analysis with a Chiralcel OD-H column (hexane/2-propanol 95:5, 1.0 mL/min, 220 nm); t$_r$ (major)=21.05 min, t$_r$ (minor)=24.02 min; $^1$H NMR (500 MHz, CDCl$_3$): δ 7.44-7.39 (m, 4H), 7.37 (m, 1H), 6.86 (d, J=1.5 Hz, 2H), 6.81 (s, 1H), 5.11 (s, 2H), 4.77 (d, J=7.8 Hz, 1H), 4.12 (m, 1H), 3.49 (s, 3H), 3.06 (dd, J=16.3, 5.4 Hz, 1H), 2.89 (dd, J=16.3, 8.8 Hz, 1H), 1.81 (s, 1H). $^{13}$C NMR (125 MHz, CDCl$_3$): δ 151.4, 149.1, 138.1, 128.8, 128.7, 127.1, 120.9, 117.3, 117.2, 116.6, 95.2, 81.8, 68.2, 55.9, 33.0. HRMS (ESI) m/z: calcd for C$_{17}$H$_{18}$NaO$_4$ [M+Na]$^+$ 309.1097, found 309.1094.

(2R,3S)-2-phenylchromane-3,6-diol (3ac)

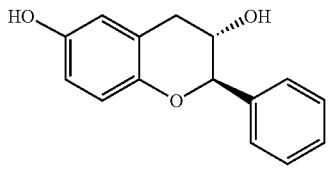 [SMILES: Oc1ccc2c(c1)C[C@H](O)[C@@H](c1ccccc1)O2]

White solid, 95% yield; m.p. 187-188° C.; $[\alpha]^{20}_D$=−2 (c=0.41, MeOH); ee was determined to be 97% by HPLC analysis with a Chiralcel AD-H column (hexane/2-propanol 80:20, 1.0 mL/min, 220 nm); t$_r$ (major)=19.23 min, t$_r$ (minor)=22.39 min; $^1$H NMR (500 MHz, MeOD): δ 7.42-7.36 (m, 4H), 7.33 (m, 1H), 6.86 (d, J=8.7 Hz, 1H), 6.59 (dd, J=8.7, 2.9 Hz, 1H), 6.54 (d, J=2.8 Hz, 1H), 4.75 (d, J=7.5 Hz, 1H), 4.08 (m, 1H), 2.93 (dd, J 16.3, 5.2 Hz, 1H), 2.79 (dd, J=16.2, 8.2 Hz, 1H). $^{13}$C NMR (125 MHz, MeOD): δ 150.8, 147.3, 139.5, 127.9, 127.6, 126.8, 121.0, 116.3, 115.1, 114.2, 81.7, 67.4, 32.8. HRMS (ESI) m/z: calcd for C$_{15}$H$_{14}$NaO$_3$ [M+Na]$^+$ 265.0835, found 265.0833.

(2R,3S)-6-fluoro-2-phenylchroman-3-ol (3ad)

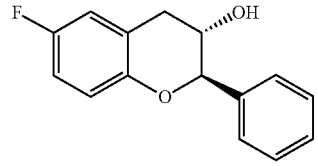 [SMILES: O[C@H]1Cc2cc(F)ccc2O[C@@H]1c1ccccc1]

White solid, 44% yield; m.p. 110-111° C.; $[\alpha]^{20}_D$=−11 (c=0.55, CH$_2$Cl$_2$); ee was determined to be 94% by HPLC analysis with a Chiralcel OD-H column (hexane/2-propanol 95:5, 1.0 mL/min, 210 nm); t$_r$ (major)=10.36 min, t$_r$ (minor)=11.32 min; $^1$H NMR (500 MHz, CDCl$_3$): δ 7.43-7.41 (m, 4H), 7.38 (m, 1H), 6.88-6.80 (m, 3H), 4.77 (d, J=7.9 Hz, 1H), 4.11 (m, 1H), 3.05 (dd, J=16.4, 5.4 Hz, 1H), 2.89 (dd, J=16.4, 8.8 Hz, 1H), 1.81 (s, 1H). $^{13}$C NMR (125 MHz, CDCl$_3$): δ 157.3 (d, J=237.3 Hz), 150.7 (d, J=1.7 Hz), 137.9, 128.9, 128.8, 127.1, 121.5 (d, J=7.9 Hz), 117.5 (d, J=8.2 Hz), 115.8 (d, J=22.9 Hz), 114.6 (d, J=23.2 Hz), 81.9, 67.9, 32.9. HRMS (ESI) m/z: calcd for C$_{15}$H$_{12}$FO$_2$ [M−H]$^-$ 243.0827, found 243.0825; calcd for C$_{15}$H$_{12}$$^{19}$FO$_2$ [M−H]$^-$ 244.0855, found 244.0858. $^{19}$F NMR (376 MHz, CDCl$_3$): δ −123.47.

(2R,3S)-6-chloro-2-phenylchroman-3-ol (3ae)

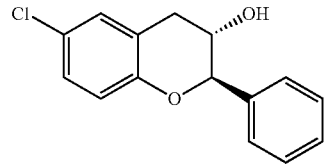 [SMILES: O[C@H]1Cc2cc(Cl)ccc2O[C@@H]1c1ccccc1]

White solid, 42% yield; m.p. 130-131° C.; $[\alpha]^{20}_D$=+9 (c=0.68, CH$_2$Cl$_2$); ee was determined to be 99% by HPLC analysis with a Chiralcel OD-H column (hexane/2-propanol 95:5, 1.0 mL/min, 210 nm); t$_r$ (major) 11.04 min, t$_r$ (minor) 12.32 min; $^1$H NMR (500 MHz, CDCl$_3$): δ 7.42-7.36 (m, 5H), 7.12-7.09 (m, 2H), 6.86 (d, J=8.5 Hz, 1H), 4.80 (d, J=7.8 Hz, 1H), 4.10 (m, 1H), 3.03 (dd, J=16.3, 5.3 Hz, 1H), 2.87 (dd, J=16.4, 8.7 Hz, 1H), 1.87 (s, 1H). $^{13}$C NMR (125 MHz, CDCl$_3$): δ 153.7, 137.7, 129.5, 128.9, 128.8, 127.8, 127.0, 125.8, 121.8, 117.8, 81.9, 67.8, 32.6. HRMS (ESI) m/z: calcd for C$_{15}$H$_{12}$ClO$_2$ [M−H]$^-$ 259.0531, found 259.0530; calcd for C$_{15}$H$_{12}$$^{37}$ClO$_2$ [M−H]$^-$ 261.0496, found 261.0501.

(2S,3R)-6-chloro-2-phenylchroman-3-ol (3ae')

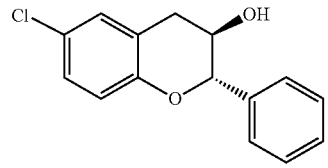 [SMILES: O[C@@H]1Cc2cc(Cl)ccc2O[C@H]1c1ccccc1]

White solid, 41% yield; $[\alpha]^{20}_D$=−7 (c=0.20, CH$_2$Cl$_2$); ee was determined to be 99% by HPLC analysis with a Chi-

(2R,3S)-6-chloro-7-methyl-2-phenylchroman-3-ol (3af)

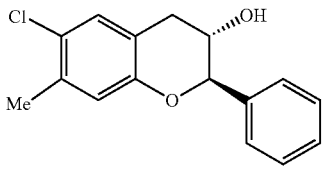 [SMILES: Cc1cc2c(cc1Cl)C[C@H](O)[C@@H](c1ccccc1)O2]

White solid, 41% yield; m.p. 129-130° C.; $[\alpha]^{20}_D=-9$ (c=0.54, $CH_2Cl_2$); ee was determined to be 98% by HPLC analysis with a Chiralcel AD-H column (hexane/2-propanol 90:10, 1.0 mL/min, 210 nm); $t_r$ (major)=8.47 min, $t_r$ (minor)=9.83 min; $^1$H NMR (500 MHz, $CDCl_3$): δ 7.41-7.36 (m, 5H), 7.08 (s, 1H), 6.81 (s, 1H), 4.80 (d, J=7.6 Hz, 1H), 4.10 (m, 1H), 3.00 (dd, J=16.2, 5.2 Hz, 1H), 2.84 (dd, J=16.1, 8.5 Hz, 1H), 2.31 (s, 3H), 1.82 (s, 1H). $^{13}$C NMR (125 MHz, $CDCl_3$): δ 152.4, 137.9, 135.4, 129.7, 128.9, 128.8, 127.0, 126.1, 119.0, 118.6, 81.8, 67.9, 32.1, 19.9. HRMS (ESI) m/z: calcd for $C_{16}H_{16}ClO_2$ [M-H]$^-$ 273.0688, found 273.0688; calcd for $C_{16}H_{16}{}^{37}ClO_2$ [M-H]$^-$ 275.0653, found 275.0659.

(2R,3S)-6,8-dichloro-2-phenylchroman-3-ol (3ag)

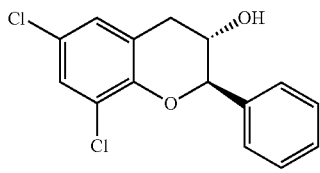 [SMILES: O[C@H]1Cc2cc(Cl)cc(Cl)c2O[C@@H]1c1ccccc1]

White solid, 44% yield; m.p. 126-127° C.; $[\alpha]^{20}_D=-48$ (c=0.50, $CH_2Cl_2$); ee was determined to be 98% by HPLC analysis with a Chiralcel OD-H column (hexane/2-propanol 95:5, 1.0 mL/min, 210 nm); $t_r$ (major)=12.76 min, $t_r$ (minor)=13.69 min; $^1$H NMR (500 MHz, $CDCl_3$): δ 7.42-7.34 (m, 5H), 7.25 (m, 1H), 6.98 (m, 1H), 4.94 (d, J=7.2 Hz, 1H), 4.10 (m, 1H), 2.99 (dd, J=16.5, 5.1 Hz, 1H), 2.86 (dd, J=16.5, 8.2 Hz, 1H), 1.92 (s, 1H). $^{13}$C NMR (125 MHz, $CDCl_3$): δ 148.5, 137.3, 128.9, 128.8, 128.1, 128.0, 126.6, 125.5, 122.9, 122.3, 82.2, 67.5, 32.3. HRMS (ESI) m/z: calcd for $C_{15}H_{11}Cl_2O_2$ [M-H]$^-$ 293.0136, found 293.0142; calcd for $C_{15}H_{11}{}^{37}Cl_2O_2$[M-H]$^-$ 295.0107, found 295.0113.

(2S,3R)-6,8-dichloro-2-phenylchroman-3-ol (3ag')

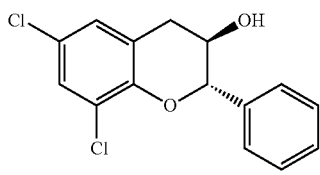

White solid, 40% yield; $[\alpha]^{20}_D=+67$ (c=0.24, $CH_2Cl_3$); ee was determined to be 98% by HPLC analysis with a Chiralcel OD-H column (hexane/2-propanol 95:5, 1.0 mL/min, 210 nm); $t_r$ (minor)=11.33 min, $t_r$ (major)=12.19 min.

(2R,3S)-6-chloro-2-(4-chlorophenyl)chroman-3-ol (3ah)

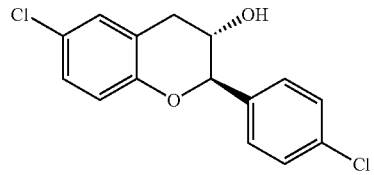 [SMILES: O[C@H]1Cc2cc(Cl)ccc2O[C@@H]1c1ccc(Cl)cc1]

White solid, 45% yield; m.p. 138-139° C.; $[\alpha]^{20}_D=+69$ (c=0.40, $CH_2Cl_2$); ee was determined to be 97% by HPLC analysis with a Chiralcel AD-H column (hexane/2-propanol 90:10, 1.0 mL/min, 210 nm); $t_r$ (major)=10.38 min, $t_r$ (minor)=11.23 min; $^1$H NMR (500 MHz, $CDCl_3$): δ 7.39-7.34 (m, 4H), 7.11-7.08 (m, 2H), 6.84 (d, J=8.6 Hz, 1H), 4.78 (d, J=7.8 Hz, 1H), 4.06 (m, 1H), 3.02 (dd, J=16.4, 5.3 Hz, 1H), 2.86 (dd, J=16.4, 8.7 Hz, 1H), 1.87 (s, 1H). $^{13}$C NMR (125 MHz, $CDCl_3$): δ 152.4, 136.4, 134.6, 129.5, 129.0, 128.4, 127.9, 126.0, 121.6, 117.8, 81.2, 67.7, 32.6. HRMS (ESI) m/z: calcd for $C_{15}H_{11}Cl_2O_2$ [M-H]$^-$ 293.0136, found 293.0143; calcd for $C_{15}H_{11}{}^{37}Cl_2O_2$[M-H]$^-$ 295.0107, found 295.0112.

(2R,3S)-2-(3,4-difluorophenyl)-5,7-difluorochroman-3-ol (3ai)

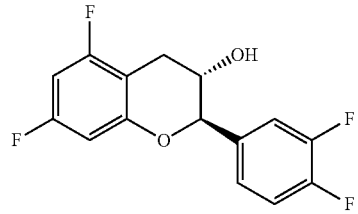 [SMILES: O[C@H]1Cc2c(F)cc(F)cc2O[C@@H]1c1ccc(F)c(F)c1]

White solid, 40% yield, colorless oil; $[\alpha]^{20}_D=-46$ (c=0.29, $CH_2Cl_3$); ee was determined to be 99% by HPLC analysis with a Chiralcel AD-H column (hexane/2-propanol 90:10, 1.0 mL/min, 220 nm); $t_r$ (major)=6.81 min; $^1$H NMR (500 MHz, $CDCl_3$): δ 7.29-7.16 (m, 3H), 6.52-6.47 (m, 2H), 4.80 (d, J=7.9 Hz, 1H), 4.06 (m, 1H), 3.08 (dd, J=16.5, 5.5 Hz, 1H), 2.74 (dd, J=16.4, 8.5 Hz, 1H), 1.97 (s, 1H). $^{13}$C NMR (125 MHz, $CDCl_3$): δ 163.4 (d, J=15.8 Hz), 162.1 (d, J=14.9 Hz), 160.9 (d, J=15.4 Hz), 160.1 (d, J=15.1 Hz), 155.1 (dd, J=14.4, 10.0 Hz), 151.5 (dd, J=12.5, 4.8 Hz), 149.5 (dd, J=12.4, 5.3 Hz), 134.5 (t, J=4.4 Hz), 123.2 (q, J=3.3 Hz), 117.6 (d, J=17.3 Hz), 116.1 (d, J=18.0 Hz), 104.5 (dd, J=21.8, 3.7 Hz), 99.7 (dd, J=26.7, 3.7 Hz), 96.9 (t, J=26.0 Hz), 80.8, 67.2, 26.4 (d, J=2.8 Hz). HRMS (ESI) m/z: calcd for $C_{15}H_9ClF_4O_2$[M-H]$^-$ 297.0539, found 297.0544; calcd for $C_{15}H_9{}^{19}F_4O_2$ [M-H]$^-$ 298.0572, found 298.0577. $^{19}$F NMR (376 MHz, $CDCl_3$): δ -119.98-119.99 (m, 1F), -113.85-113.87 (m, 1F), -136.18-136.24 (m, 1F), -137.12-137.18 (m, 1F).

(2R,3S)-2-phenylchroman-3-yl 3,4,5-trihydroxybenzoate (4)

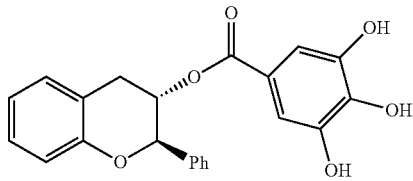 [SMILES: O=C(O[C@H]1Cc2ccccc2O[C@@H]1c1ccccc1)c1cc(O)c(O)c(O)c1]

White solid, 70% yield; ¹H NMR (500 MHz, CDCl₃): δ 7.38-7.36 (m, 2H), 7.32-7.24 (m, 3H), 7.19 (t, J=7.6 Hz, 1H), 7.05-7.00 (m, 4H), 6.92 (t, J=7.4 Hz, 1H), 5.53 (dd, J=10.6, 5.4 Hz, 1H), 5.36 (d, J=5.5 Hz, 1H), 3.06 (dd, J=16.8, 4.5 Hz, 1H), 2.94 (dd, J=16.7, 5.7 Hz, 1H). ¹³C NMR (125 MHz, CDCl₃): δ 166.2, 153.4, 143.5, 138.1, 137.0, 129.9, 128.7, 128.3, 128.0, 126.1, 121.1, 120.9, 119.0, 116.5, 109.9, 78.2, 70.2, 28.3.

(2R,3S)-2-(4-hydroxyphenyl)chroman-3-ol (5)

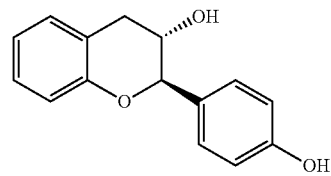 [SMILES: Oc1ccc([C@H]2Oc3ccccc3C[C@@H]2O)cc1]

White solid, 94% yield; m.p. 106-107° C.; $[\alpha]^{20}_D$=+13.8 (c=0.33, MeOH); ee was determined to be >99% by HPLC analysis with a Chiralcel AD-H column (hexane/2-propanol 80:20, 1.0 mL/min, 220 nm); $t_r$ (major)=12.50 min; ¹H NMR (500 MHz, MeOD): δ 7.25-7.23 (m, 2H), 7.12-7.07 (m, 2H), 6.87 (t, J=7.4 Hz, 1H), 6.82-6.80 (m, 3H), 4.73 (d, J=7.6 Hz, 1H), 4.07 (m, 1H), 3.00 (dd, J=16.1, 5.1 Hz, 1H), 2.83 (dd, J=16.1, 8.4 Hz, 1H). ¹³C NMR (125 MHz, MeOD): δ 157.1, 154.2, 130.0, 129.5, 128.1, 127.1, 120.4, 120.3, 115.7, 114.7, 81.7, 67.1, 32.7. HRMS (ESI) m/z: calcd for C₁₅H₁₄NaO₃ [M+Na]⁺265.0835, found 265.0833.

(2R,3S)-2-phenylchroman-4-d-3-ol (3a')

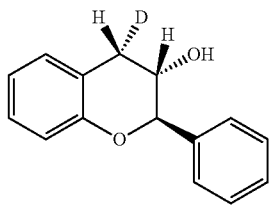 [SMILES: [2H][C@H]1c2ccccc2O[C@H](c2ccccc2)[C@H]1O]

White solid, 44% yield; ee was determined to be >99% by HPLC analysis with a Chiralcel AD-H column (hexane/2-propanol 90:10, 1.0 mL/min, 220 nm); $t_r$ (major)=9.82 min; ¹H NMR (400 MHz, CDCl₃): δ 7.46-7.41 (m, 4H), 7.37 (m, 1H), 7.17 (m, 1H), 7.12 (d, J=5.8 Hz, 1H), 6.95-6.92 (m, 2H), 4.82 (d, J=6.3 Hz, 1H), 4.13 (t, J=5.7 Hz, 1H), 3.07 (d, J=3.6 Hz, 1H), 2.33 (dd, J=12.8, 7.1 Hz, 0.1H).

INDUSTRIAL APPLICABILITY

The present invention relates to a highly efficient kinetic resolution of chromenes for the first time via Cu-catalyzed asymmetric hydroboration. This novel approach features a simple one-pot synthesis of chiral flavan-3-ols containing two vicinal stereogenic centers via a highly efficient kinetic resolution pathway (s factor up to 1060, >99% ee for most substrates and products, exclusively trans products). In addition, the anti-inflammation effects of these diversified flavan-3-ols were further studied by the in vitro experiments and RNA-sequencing (RNA-seq) analysis. The synthesized flavan-3-ols showed inhibitory effects on the expression and secretion of pro-inflammation cytokines including IL-1β, IL-6 and TNF-α, as well as inhibiting the inflammation responses through downregulating the gene transcriptions closely related to IL-17 signaling pathway, PI3K-Akt signaling pathway and TNF signaling pathway. The results suggested these newly synthesized flavan-3-ols have the potential to be potent lead compounds for developing anti-inflammatory drugs.

What is claimed is:
1. A compound of Formula 1:

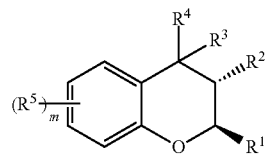

or a pharmaceutically acceptable salt thereof, wherein
m is a whole number selected from 1-3;
n is a whole number selected from 1-3;
p is a whole number selected from 1-2;
q is a whole number selected from 2-6;
$R^1$ is

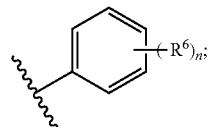

$R^2$ is —OR, —O(C=O)$R^7$, —O(C=O)O$R^7$, —O(C=O)N($R^7$)₂, or —O(P=O)(OH)₂;
each of $R^3$ and $R^4$ is hydrogen;
$R^5$ for each instance is independently selected from the group consisting of halide, methyl, chloride, fluoride, and —OCH₂OMe;
$R^6$ for each instance is independently selected from the group consisting of hydrogen, halide, nitrile, nitro, —OR, —SR, —NR₂, —(C=O)R, —C(C=O)OR, —(C=O)NR₂, —N(R)(C=O)R, —O(C=O)R, —N(R)(C=O)OR, —O(C=O)NR₂, —SO₂R, —SO₂NR₂, haloalkyl, perhaloalkyl, alkyl, cycloalkyl, alkenyl, alkynyl, aryl, heterocycloalkyl, heteroaryl, —OCH₂OMe, and —(CR₂)$_q$$R^8$;
$R^7$ for each instance is independently selected from the group consisting of hydrogen, alkyl, cycloalkyl, alkenyl, alkynyl, aryl, heterocycloalkyl, heteroaryl, and —(CR$_2$)$_q$R$^8$; or two instances of R$^7$ taken together form a 5-6 membered cycloalkyl, heterocycloalkyl, or heteroaryl;

R$^8$ for each instance is independently selected from the group consisting of —OR, —SR, —NR$_2$, —(C=O)R, —(C=O)OR, —(C=O)NR$_2$, —N(R)(C=O)R, —O(C=O)R, —N(R)(C=O)OR, —O(C=O)NR$_2$, —SO$_2$R, and —SO$_2$NR$_2$; and R for each instance is independently selected from the group consisting of hydrogen, alkyl, cycloalkyl, alkenyl, alkynyl, aryl, heterocycloalkyl, and heteroaryl; or two instances of R taken together form a 5-6 membered heterocycloalkyl or heteroaryl; or a compound of Formula 2:

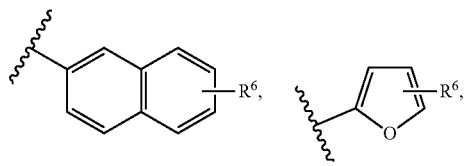

or a pharmaceutically acceptable salt thereof, wherein
m is a whole number selected from 1-2;
q is a whole number selected from 2-6;
R$^1$ is

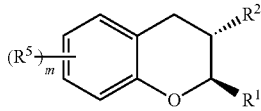

or propyl;

R$^2$ is —OR, —O(C=O)R$^7$, —O(C=O)OR$^7$, —O(C=O)N(R$^7$)$_2$, or —O(P=O)(OH)$_2$;

R$^5$ for each instance is independently selected from the group consisting of hydrogen, halide, nitrile, nitro, —OR, —NR$_2$, haloalkyl, perhaloalkyl, alkyl, cycloalkyl, aryl, heterocycloalkyl, heteroaryl, —OCH$_2$OMe, and —(CR$_2$)$_q$R$^8$;

R$^6$ for each instance is independently selected from the group consisting of hydrogen, halide, nitrile, nitro, —OR, —NR$_2$, haloalkyl, perhaloalkyl, alkyl, cycloalkyl, aryl, heterocycloalkyl, heteroaryl, —OCH$_2$OMe, and —(CR$_2$)$_q$R$^8$;

R$^7$ for each instance is independently selected from the group consisting of hydrogen, alkyl, cycloalkyl, alkenyl, alkynyl, aryl, heterocycloalkyl, heteroaryl, and —(CR$_2$)$_q$R$^8$; or two instances of R$^7$ taken together form a 5-6 membered cycloalkyl, heterocycloalkyl, or heteroaryl;

R$^8$ for each instance is independently selected from the group consisting of —OR, —SR, —NR$_2$, —(C=O)R, —(C=O)OR, —(C=O)NR$_2$, —N(R)(C=O)R, —O(C=O)R, —N(R)(C=O)OR, —O(C=O)NR$_2$, —SO$_2$R, and —SO$_2$NR$_2$; and R for each instance is independently selected from the group consisting of hydrogen, alkyl, cycloalkyl, alkenyl, alkynyl, aryl, heterocycloalkyl, and heteroaryl; or two instances of R taken together form a 5-6 membered heterocyloalkyl or heteroaryl.

2. The compound of claim 1, wherein m is 1 or 2.

3. The compound of claim 1, wherein R$^2$ is —OH, —O(C=O)R$^7$, or —O(P=O)(OH)$_2$.

4. The compound of claim 1, wherein each of n and p is 1 and R$^6$ is hydrogen.

5. The compound of claim 2, wherein R$^5$ for each instance is independently selected from the group consisting of halide, methyl, chloride, fluoride, and —OCH$_2$OMe.

6. The compound of claim 1, wherein R$^2$ is —OH and R$^6$ is hydrogen, halide, trifluoromethyl, —OCH$_2$OMe, or —OCH$_2$Ph.

7. The compound of claim 6, wherein R$^5$ for each instance is independently selected from the group consisting of hydrogen, methyl, —OCH$_2$OMe, halide, and —OMe.

8. The compound of claim 1, wherein the compound has Formula 2 and R$^5$ for each instance is independently selected from the group consisting of hydrogen and chloride and R$^2$ is —OH.

9. The compound of claim 8, wherein R$^6$ is hydrogen.

10. The compound of claim 1, wherein the compound is selected from the group consisting of:

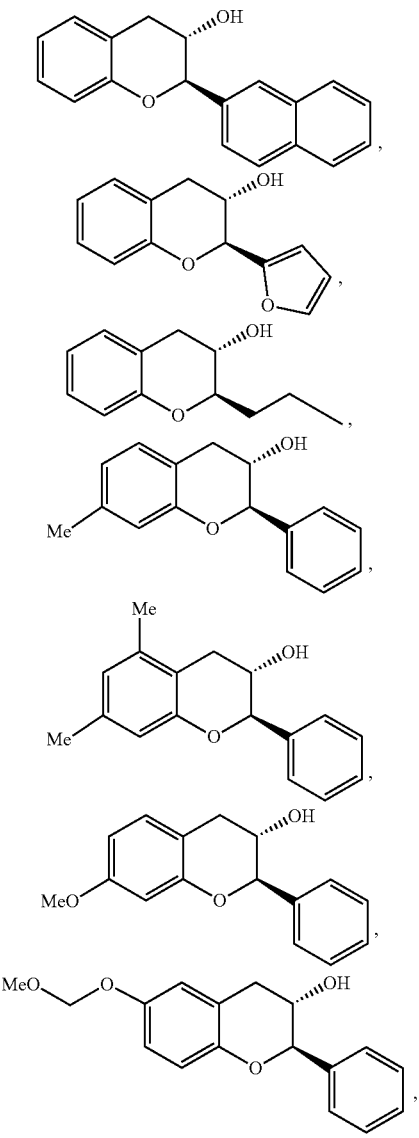

-continued
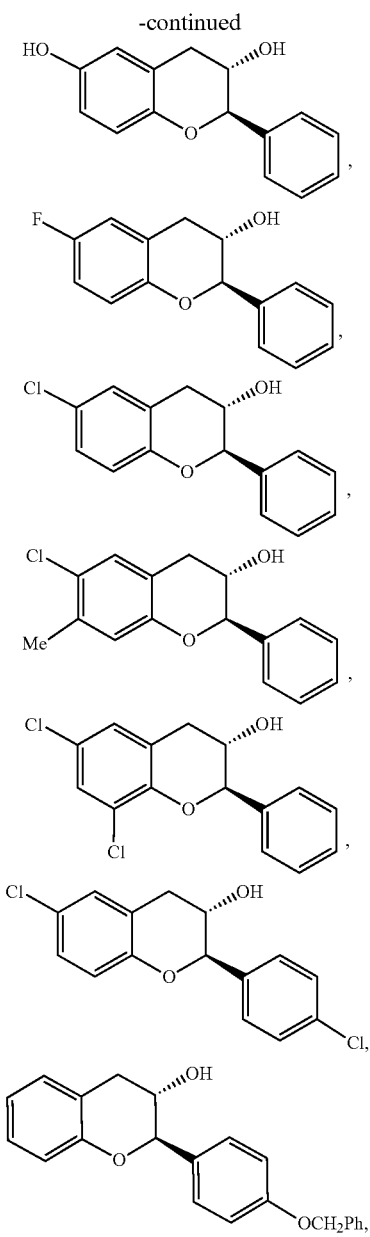
11. The compound of claim 1, wherein the compound is selected from the group consisting of:
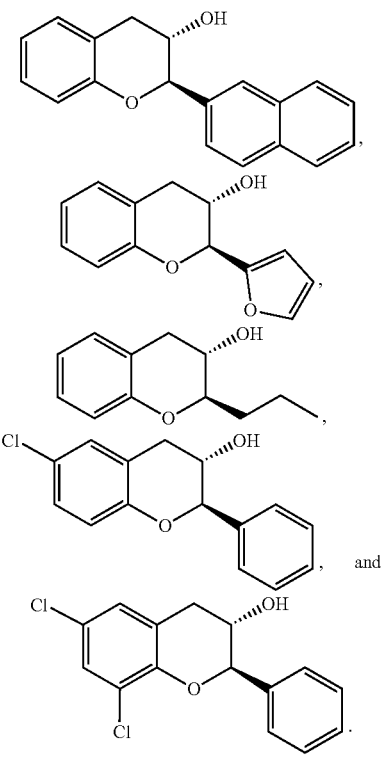
12. The compound of claim 1, wherein the compound is:
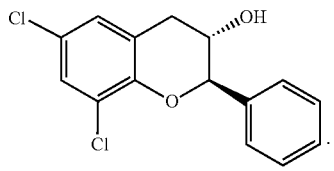 [SMILES: O[C@H]1Cc2cc(Cl)cc(Cl)c2O[C@@H]1c1ccccc1]
13. A pharmaceutical composition comprising the compound of claim 1 and at least one pharmaceutically acceptable excipient or pharmaceutically acceptable carrier.
* * * * *